(12) United States Patent
Clem et al.

(10) Patent No.: US 9,381,172 B2
(45) Date of Patent: Jul. 5, 2016

(54) SMALL MOLECULE CHOLINE KINASE INHIBITORS, SCREENING ASSAYS, AND METHODS FOR TREATMENT OF NEOPLASTIC DISORDERS

(75) Inventors: Brian Clem, Louisville, KY (US); Sucheta Telang, Louisville, KY (US); John Trent, Louisville, KY (US); Jason Chesney, Louisville, KY (US); Pooran Chand, Birmingham, AL (US); Gilles Tapolsky, Louisville, KY (US)

(73) Assignee: UNIVERSITY OF LOUISVILLE RESEARCH FOUNDATION, INC., Louisville, KY (US)

( * ) Notice: Subject to any disclaimer, the term of this patent is extended or adjusted under 35 U.S.C. 154(b) by 0 days.

(21) Appl. No.: 13/470,274

(22) Filed: May 12, 2012

(65) Prior Publication Data

US 2013/0012557 A1    Jan. 10, 2013

Related U.S. Application Data

(63) Continuation of application No. 12/824,680, filed on Jun. 28, 2010, now abandoned.

(60) Provisional application No. 61/220,620, filed on Jun. 26, 2009.

(51) Int. Cl.

| | |
|---|---|
| *A61K 31/4196* | (2006.01) |
| *A61K 31/165* | (2006.01) |
| *A61K 31/216* | (2006.01) |
| *A61K 31/24* | (2006.01) |
| *A61K 31/4166* | (2006.01) |
| *A61K 31/426* | (2006.01) |
| *A61K 31/427* | (2006.01) |
| *A61K 31/428* | (2006.01) |
| *A61K 31/4709* | (2006.01) |
| *C07D 233/74* | (2006.01) |
| *C07D 249/12* | (2006.01) |
| *C07D 277/24* | (2006.01) |
| *C07D 401/12* | (2006.01) |
| *C07D 403/12* | (2006.01) |
| *C07D 413/12* | (2006.01) |
| *C07D 417/12* | (2006.01) |

(52) U.S. Cl.
CPC .............. *A61K 31/165* (2013.01); *A61K 31/216* (2013.01); *A61K 31/24* (2013.01); *A61K 31/4166* (2013.01); *A61K 31/4196* (2013.01); *A61K 31/426* (2013.01); *A61K 31/427* (2013.01); *A61K 31/428* (2013.01); *A61K 31/4709* (2013.01); *C07D 233/74* (2013.01); *C07D 249/12* (2013.01); *C07D 277/24* (2013.01); *C07D 401/12* (2013.01); *C07D 403/12* (2013.01); *C07D 413/12* (2013.01); *C07D 417/12* (2013.01)

(58) Field of Classification Search
None
See application file for complete search history.

(56) References Cited

U.S. PATENT DOCUMENTS

| | | | |
|---|---|---|---|
| 6,962,936 B2 * | 11/2005 | Hale et al. ................. | 514/381 |
| 2005/0085531 A1 | 4/2005 | Hodge et al. | |
| 2007/0185170 A1 * | 8/2007 | Lacal Sanjuan et al. ..... | 514/343 |

FOREIGN PATENT DOCUMENTS

| | | |
|---|---|---|
| WO | 98/05644 | 2/1998 |
| WO | 2008/005644 A1 | 1/2008 |

OTHER PUBLICATIONS

Sausville et al. (Cancer Research, 2006, vol. 66, pp. 3351-3354).*
Johnson et al. (British J. of Cancer, 2001, 84(10):1424-1431).*
Cuadrado et al. "Phosphorylcholine: A Novel Second Messenger Essential for Mitogenic Activity of Growth Factors" (1993) Oncogene, vol. 8, pp. 2959-2968.
Fan et al., "Rhabdomyosarcoma cells show an energy producing anabolic metabolic phenotype compared with primary myocytes," Molecular Cancer (Oct. 21, 2008) vol. 7, Article No. 79.
Hernandez-Alcoceba et al., "Choline kinase inhibitors as a novel approach for antiproliferative drug design" Oncogene (1997) vol. 15, pp. 2289-2301.
Johnson et al., "Relationships between drug activity in NCI preclinical in vitro and in vivo models and early clinical trials" British Journal of Cancer (2001) vol. 84, No. 10, pp. 1424-1431.
Lane et al., "Isotopomer-based metabolomic analysis by NMR and mass spectrometry," Methods in Cell Biol. (2008) vol. 84, pp. 541-588.
Mori et al., "Choline Kinase Down-regulation Increases the Effect of 5-Fluorouracil in Breast Cancer Cells" Cancer Res (Dec. 1, 2007) vol. 67, No. 23, pp. 11284-11290.
Sausville et al., "Contributions of Human Tumor Xenografts to Anticancer Drug Development" Cancer Res (Apr. 1, 2006) vol. 66, No. 7, pp. 3351-3354.
Telang et al., "Ras transformation requires metabolic control by 6-phosphofructo-2-kinase" Oncogene (2006) vol. 25, pp. 7225-7234.

\* cited by examiner

*Primary Examiner* — Bong-Sook Baek
(74) *Attorney, Agent, or Firm* — Calfee, Halter & Griswold LLP; Harry J. Guttman

(57) ABSTRACT

Small molecule choline kinase inhibitors, pharmaceutical compositions thereof, and screening methods for identifying and evaluating choline kinase inhibitors are provided. Safe and effective methods for treating subjects suffering from a disorder or disease characterized by neoplastic cell proliferation employing the choline kinase inhibitors are also provided.

15 Claims, 18 Drawing Sheets

1A.

1B.

1C.

1D.

2B.

*SIGNIFICANT DIFFERENCE: P<0.05

*SIGNIFICANT DIFFERENCE: P<0.05

*SIGNIFICANT DIFFERENCE: P<0.05

4A.
4B.
FIGURES 4A AND 4B

4C.

*SIGNIFICANT DIFFERENCE: P<0.05

FIGURE 10

Table 5

| Compounds | K562 | MDA-MB231 | U937 | NCI-H82 | Calu-6 |
|---|---|---|---|---|---|
| ACT-CK-001 | 44.83 | 44.7 | | | |
| ACT-CK-004 | 31 | >100 | | | |
| ACT-CK-005 | 17.5 | 42.4 | | | |
| ACT-CK-006 | 16.4 | >100 | | | |
| ACT-CK-010 | 91.5 | >100 | | | |
| ACT-CK-014 | 38.2 | 48.1 | | | |
| ACT-CK-015 | 18.9 | 52.2 | | | |
| ACT-CK-017 | 21 | 34.3 | | | |
| ACT-CK-018 | 17.9 | 38.2 | | | |
| ACT-CK-019 | 10.2 | 39 | | | |
| ACT-CK-020 | 4 | 66.3 | | | |
| ACT-CK-021 | 6.3 | 28.2 | | | |
| ACT-CK-022 | 35.11 | >100 | | | |
| ACT-CK-023 | 44.32 | >100 | | | |
| ACT-CK-025 | 3 | 12 | | | |
| ACT-CK-027 | 32.3 | > 100 | | | |
| ACT-CK-029 | 13.7 | > 100 | | | |
| ACT-CK-030 | 21.2 | 56 | | | |
| ACT-CK-031 | 43.5 | 55.7 | | | |
| ACT-CK-032 | 32.1 | 45.2 | | | |
| ACT-CK-033 | 17.9 | 16.1 | | | |
| ACT-CK-034 | 13.8 | >100 | | | |
| ACT-CK-035 | 32.1 | >100 | | | |
| ACT-CK-037 | 16.3 | > 100 | | | |
| ACT-CK-039 | 21.5 | 43.1 | | | |
| ACT-CK-040 | 9.2 | 43 | | | |
| ACT-CK-041 | 26.4 | 89.9 | | | |
| ACT-CK-042 | >100 | >100 | | | |
| ACT-CK-043 | 0.9 | 22 | | | |
| ACT-CK-044 | 21.2 | 45.5 | | | |
| ACT-CK-045 | 11 | 78 | | | |
| ACT-CK-046 | 19.7 | 43.6 | | | |
| ACT-CK-047 | 7.9 | 31.2 | | | |
| ACT-CK-048 | 10 | 30.6 | | | |
| ACT-CK-049 | 2.3 | 27.1 | | | |
| ACT-CK-061 | 28.10 | >100 | | | |

| | | | | | |
|---|---|---|---|---|---|
| ACT-CK-063 | 37.00 | 78.70 | | | |
| ACT-CK-066 | 11.40 | 76.20 | | | |
| ACT-CK-070 | 32.10 | 68.20 | | | |
| ACT-CK-079 | 40.61 | 45.04 | | | |
| ACT-CK-082 | >100 | >100 | | | |
| ACT-CK-085 | 4.40 | 16.28 | | | |
| ACT-CK-089 | 76.40 | >100 | | | |
| ACT-CK-092 | 33.40 | 56.23 | | | |
| ACT-CK-096 | 34.00 | 149.00 | | | |
| ACT-CK-099 | >100 | >100 | | | |
| ACT-CK-102 | >100 | >100 | | | |
| ACT-CK-104 | >100 | >100 | | | |
| ACT-CK-105 | 59.00 | 64.00 | | | |
| ACT-CK-110 | 46.00 | 14.00 | | | |
| ACT-CK-111 | 95.00 | 26.00 | | | |
| ACT-CK-112 | >100 | 24.00 | | | |
| ACT-CK-121 | 39.00 | 10.00 | | | |
| ACT-CK-124 | 23.00 | 16.00 | | | |
| ACT-CK-131 | 88.00 | 34.70 | 33.00 | 28.00 | 8.00 |
| ACT-CK-132 | 45.00 | 14.00 | 49.00 | 33.00 | 35.00 |
| ACT-CK-133 | 46.00 | 16.00 | 33.00 | 32.00 | 35.00 |
| ACT-CK-134 | 72.00 | 43.50 | 72.00 | 45.00 | 40.00 |
| ACT-CK-135 | 51.00 | 17.80 | 33.00 | 33.00 | 42.00 |
| ACT-CK-137 | 40.00 | 21.30 | 50.00 | 18.00 | 38.00 |
| ACT-CK-138 | >100 | 41.50 | 39.00 | 41.00 | 37.00 |
| ACT-CK-139 | 75.00 | 6.80 | 35.00 | 32.00 | 39.00 |
| ACT-CK-140 | 41.00 | 79.00 | 20.40 | | 41.60 |
| ACT-CK-144 | 34.00 | 47.00 | 46.00 | | 37.80 |
| ACT-CK-145 | 1.20 | 16.80 | 0.56 | | 0.64 |
| ACT-CK-146 | 31.70 | 91.00 | 34.10 | | 54.00 |
| ACT-CK-166 | 54.00 | >100 | 30.80 | >100 | 100.00 |
| ACT-CK-167 | 54.00 | >100 | 40.50 | >100 | 65.50 |
| ACT-CK-168 | 10.50 | 7.00 | 1.36 | 11.05 | 3.80 |

FIGURE 10 cont.

SMALL MOLECULE CHOLINE KINASE INHIBITORS, SCREENING ASSAYS, AND METHODS FOR TREATMENT OF NEOPLASTIC DISORDERS

PRIORITY CLAIM

This application is a continuation of U.S. application Ser. No. 12/824,680 now abandoned, filed Jun. 28, 2010, which is incorporated by reference in its entirety, which claims the benefit of U.S. Provisional Application No. 61/220,620 filed Jun. 26, 2009, which is incorporated by reference in its entirety.

FIELD OF THE INVENTION

The invention generally relates to pharmaceutical therapeutics. More specifically screening methods for direct inhibitors of choline kinase, small molecule choline kinase inhibitors, and methods for treating neoplastic disorders and diseases employing them are provided.

BACKGROUND

Choline Kinase (ChoK) is a phosphotransferase which acts by phosphorylating choline to phosphocholine (PCho) as the first enzyme of the phosphatidylcholine (PC) synthetic pathway (also known as the Kennedy pathway). Adenosine-triphosphate (ATP) is the phosphate group donor.

As early as the 1980s empirical evidence began emerging implicating choline kinase in tumor development and progression. Phosphocholine, which is produced by choline kinase, was discovered to be a signal unique to lung tumors. In 2002, researchers examined 43 lung tumor tissues and adjacent normal lung tissues and appeared to confirm that choline kinase expression was increased in some neoplastic lung tissues. A global analysis of 167 non small cell lung cancer patients' tumors then appeared to establish an association between choline kinase over-expression and poor clinical outcome. In addition to lung cancer, various researchers have confirmed choline kinase over-expression and increased activity in tumors of the colon, breast, prostate and ovaries. Choline kinase expression and activity also have been reported to be associated with poor prognosis in other cancer types such as breast cancer. Choline-based radiopharmaceuticals, including $^{11}$C-choline and $^{18}$F-choline, are actively being studied in clinical trials for diagnostic utility in cancer patients using positron emission tomography. Based on these studies, choline kinase has been proposed as a prognostic marker for cancer progression and a potential target for the development of novel cancer chemotherapeutic agents. Other research has pointed to a role for activated choline kinase as a metabolic requirement for neoplastic growth and survival. Insulin, platelet-derived growth factor, fibroblast growth factor, epidermal growth factor, prolactin, estrogens and hypoxia-inducible factor-1α appear to be needed for the survival, growth and invasiveness of human cancers, and have all been typically found to stimulate choline kinase activity and increase intracellular phosphocholine. Growth factors can engage receptor-tyrosine kinases which stimulate two key signal transducers, the small GTPase Ras and the lipid kinase phosphatidylinositol-3-OH kinase (PI3K). These signal transducers then can stimulate an intersecting network that activates untethered cell growth, survival and invasiveness without influence from environmental cues and, when mutated, initiate tumors in humans.

In addition, oncogenic transformation mediated by Ras oncogenes induces high choline kinase activity levels resulting in an abnormal increase in the intracellular levels of its product, PCho. Ras gene proto-oncogenes encode a protein family of small membrane-bound GTPases which appear to be involved in cellular signal transduction from outside the cell to inside the nucleus. Activation of Ras signaling causes cell growth, division, terminal differentiation and senescence. Mutations in Ras are heavily implicated in the development of cancers. It is hypothesized that mutations may permanently activate Ras. Ras oncogenic transforming potential is acquired with point amino acid substitution mutations in codons 12, 13 or 61. These Ras mutations are found in up to approximately 6.5% of breast cancers, 30% of non-small cell lung cancers, 50% of colon cancers, and 100% of pancreatic cancers. Even in the absence of these mutations the Ras signaling pathway may be central to cancer development and progression, since several Ras pathway proteins upstream (e.g. epidermal growth factor receptor and Her2/neu) and downstream (e.g. Akt, ERK kinase) of Ras are also found to be amplified or mutated in human tumors. For example, although Ras is rarely found in mutated form in breast tumors, Ras overexpression and amplification has been observed in 50-70% of breast adenocarcinomas.

Complementary findings also support the role of ChoK in the generation of human tumors. For example, nuclear magnetic resonance (NMR) techniques have shown the presence of high PCho levels in several human tumor tissues including breast, prostate, brain and ovarian tumors with respect to normal tissues. ChoK appears to be activated by multiple growth factors and signal transducers that may be regulators of neoplastic growth and survival and may be implicated in the initiation and progression of human cancers.

Evidence for choline kinase activity in cancer has also been obtained from the observation that siRNA silencing of choline kinase mRNA expression by MDA-MB-231 breast adenocarcinoma cells reduces intracellular phosphocholine, which in turn decreases cellular proliferation and promotes differentiation. Although these studies were not conducted in vivo, they nevertheless supported the validity of choline kinase as a molecular target for the development of anti-breast cancer agents.

Ras is one of the most intensely studied oncogenes in human carcinogenesis and ChoK inhibition has been hypothesized as an anti-tumor strategy with some success. The design of compounds directly affecting ChoK activity or the enzyme activated by phosphorylcholine has provided agents with anti-tumor effects in cells transformed by oncogenes, however the specific test drugs available to-date suffer from delivery and/or safety deficiencies which make them unsuitable for clinical use.

Several ChoK inhibitors are well-known in the art. Researchers identified Hemicholinium-3 (HC-3) as a relatively potent and selective blocking agent (Cuadrado A., et al., 1993, Oncogene 8: 2959-2968, e.g.). HC-3 is a choline homologue with a biphenyl structure and has been used for designing new anti-tumor drugs. However, HC-3 is a potent respiratory paralyzing agent and is therefore not a good candidate for its use in clinical practice. Introduction of structural modifications have reduced toxic side effects but full retention of inhibitory activity is not achieved. Bisquaternized symmetric compounds derived from pyridinium have also been found to inhibit PCho production in whole cells (WO98/05644). However, these derivatives have high toxicity levels limiting extended therapeutic application. ChoK-specific siRNAs have been developed but use of an siRNA is not feasible due to a lack of suitable technology for transporting the siRNA to the tumor cell, and due to lack of selectivity of inhibition among ChoK isoforms. Mori et al (Cancer Res., 2007, 67:11284-11290).

Hence, there remains a need in the art for pharmaceutical compounds which effectively inhibit ChoK-alpha while reducing the toxic side effects which accompany the current state-of-the-art.

SUMMARY

Accordingly, the present invention provides a screening method for the identification and evaluation of small molecules for ability to interact with and directly inhibit a substrate binding pocket of choline kinase. Compounds having exceptional efficacy and safety profiles are disclosed. Structural formulas derived from inspection of the modeling and structure-function correlates of the identified compounds were derived and novel small molecule choline kinase inhibitors were synthesized.

One embodiment of the invention provides methods for treating a subject suffering from a disorder or disease characterized by neoplastic cell proliferation. The method comprises administering to the subject a therapeutically effective amount of a selective choline kinase (ChoK) inhibitor, wherein the ChoK inhibitor is selected from compounds having a structure designated and defined herein as "Formula I" or "Formula II," and in accordance with the substituent permutations defined herein explicitly with respect to Formula I and Formula II.

In specific embodiments the disease comprises tumor cell proliferation, and in very specific embodiments the tumor is a lung, breast, colorectal, pancreatic, cervical or ovarian tumor.

According to one aspect of the invention, the choline kinase inhibiting compound directly inhibits ChoK by interacting with a phosphocholine binding pocket of ChoK. In this fashion the compound occupies or interacts with the substrate binding pocket, preventing or limiting access to the pocket by its natural ligand.

In certain embodiments the selective ChoK inhibitor is a compound selected from Table 1, which constitutes compounds identified as efficacious by screening a large small molecule library. In other embodiments, the ChoK inhibitor may be selected from Table 2, which includes compounds synthesized according to formula I set forth herein, and Table 3 which includes novel compounds designed and synthesized in accordance with the invention. The compounds of the invention may be formulated as pharmaceutical compositions.

A further embodiment of the invention provides methods for treating subjects suffering from a disorder or disease benefited by suppressing cellular apoptosis. The methods comprise administering to the subject an amount of a choline kinase inhibitor effective to suppress cellular apoptosis.

The invention also provides screening methods including methods for identifying a compound that directly modulates ChoK activity. The method comprises: a) obtaining a crystal structure of ChoK or obtaining information relating to a crystal structure of ChoK, and b) modeling a test compound into or on the crystal structure coordinates to determine whether the compound binds to ChoK, wherein modeling comprises determining the ability of the compound to bind to or associate with a phosphocholine (PCho) binding pocket of ChoK defined by structural coordinates of one or more ChoK amino acid residues forming the PCho binding pocket. In specific embodiments, the crystal structure is of a splice isoform of choline kinase-α and the amino acid residues forming the PCho binding pocket include amino acid residues 116-124, 146, 256, 305-306, 308, 310-311, 323, 330, 332, 333, 345, 348-349, 354, 416, 420, 422-423, 427, 440, and 444 of the amino acid sequence set forth as SEQ ID NO: 1.

Other method embodiments include methods for identifying a compound that directly modulates ChoK activity comprising using atomic coordinates of one or more of ChoK amino acid residues to generate a three-dimensional structure of a molecule comprising a PCho binding pocket of ChoK, and employing the three-dimensional structure to identify a compound that directly modulates the activity of ChoK.

These and other embodiments and aspects of the invention will be more fully understood by reference to the following disclosure, including the Detailed Description, and Figures included herewith.

BRIEF DESCRIPTION OF THE DRAWINGS

FIG. 1. Virtual screening identified a number of novel small molecule inhibitors of choline kinase (including CK37) that were then subject to actual laboratory testing.

FIG. 3. CK37 selectively suppresses tumor cell proliferation and anchorage-independent growth.

FIG. 4. CK37 disrupts ERK phosphorylation and cellular actin cytoskeleton arrangement, and causes ultrastructural changes in the plasma membrane. FIG. 4A. Western blot analysis was performed as described in the ERK1/2 Phosphorylation method. Representative immunoblot depicting p-ERK1/2, ERK1/2, and β-actin levels from two independent experiments. FIG. 4B. Immunofluorescence confocal microscopy was performed as described in the methods. Representative images for vinculin, phalloidin and merged staining from vehicle or 10 µM CK37 treated samples from two independent experiments.

FIG. 5. CK37 administration suppresses tumor growth in vivo.

FIG. 10. The ability of the compounds listed in Tables 2 and 3 to inhibit the proliferation of cancer cells was investigated in five different cell lines. The results are set forth in Table 5 and demonstrate that many of the listed compound in accordance with the invention inhibit tumor cell proliferation at low micromolar concentrations and thus have good in vitro anticancer properties.

DETAILED DESCRIPTION

Figure 1A:
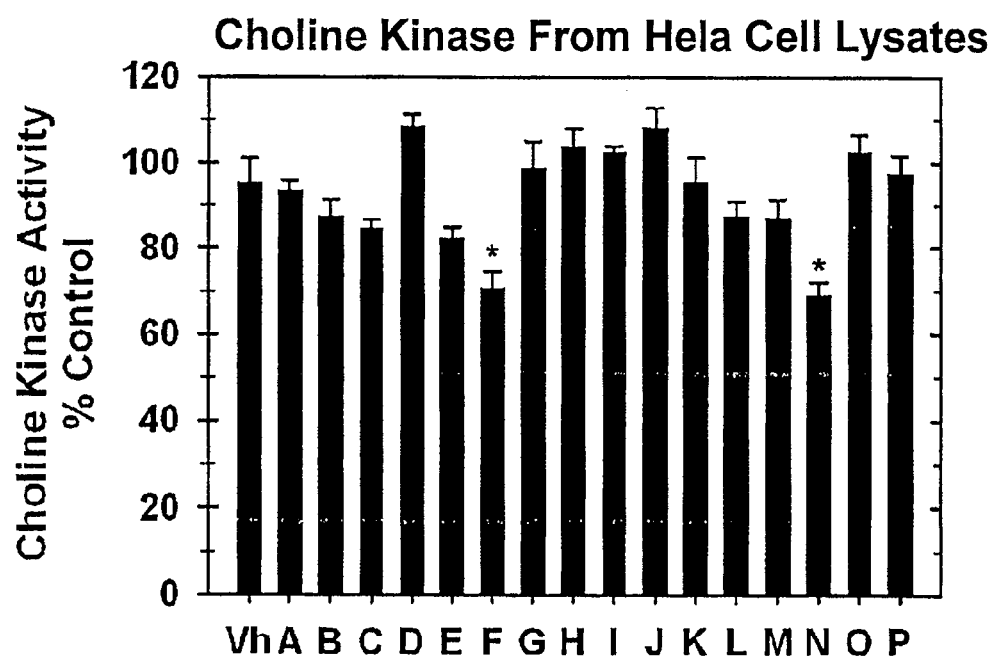
FIG. 1A. Choline kinase activity assays of Hela lysates were performed as described in the Choline Kinase Activity method. Activity assays were done in the presence of 100 µM of each compound. Data are represented as % of control activity for each compound. Mean±STD from two independent experiments. $p<0.05$.

As used herein, "substituted" is defined by the substitution of one, two, or three hydrogens on a carbon by groups including, but not limited to, halogen (e.g., Cl, Br, or F), hydroxy, thiol, amino, nitro, cyano, branched or unbranched $C_1$-$C_4$ alkyl, branched or unbranched $C_1$-$C_4$ alkylnoic, $C_1$-$C_2$ perfluorinated alkyl, alkylamino, oxo, carboxy, acetyl, amido, vinyl, and $C_1$-$C_3$ alkoxy.

"Aryl" as used herein, is defined to include an organic radical derived from an aromatic hydrocarbon consisting of 1-3 rings and containing about 6 to about 18 carbon atoms. Aryl includes but is not limited to, phenyl and naphthyl.

The term "heterocycle", as used herein, is defined as including an aromatic or non-aromatic cyclic alkyl, alkenyl, or allynyl moiety, having at least one O, S, or N atom interrupting the carbocyclic ring structure and optionally, one of the carbons of the carbocyclic ring structure may be replaced by a carbonyl. In some instances, heterocycles include monocyclics having 4 to 7 membered ring systems, bicyclics having 4 to 7 membered fused ring systems, and tricyclics having 4 to 7 membered fused ring systems; these ring systems can have 1 to 8 heteroatoms with different combinations of N, O, and S. Non-limiting examples of aromatic heterocycles are 1H-1,2,4-triazole, pyridyl, furyl, pyrrolyl, imidazolyl, benzimidazolyl, tetrazolyl, pyridazinyl, pyrimidinyl, pyrazinyl, quinolyl, pyrazolyl, indolyl, indolizinyl, purinyl, isoindolyl, and carbazolyl. Non-limiting examples of non-aromatic heterocycles are tetrahydrofuranyl, tetrahydropyranyl, piperidinyl, piperidyl, piperazinyl, imidazolidinyl, morpholino, and morpholinyl. The term "heterocycle" includes monocyclic, bicyclic, tricyclic, and tetracyclic groups.

The compounds of the present invention include those described herein including, for example, those of Formula (I) or Formula (II). These compounds can be used, for example, to inhibit choline kinase, to treat diseases, or both.

Formula (I) is

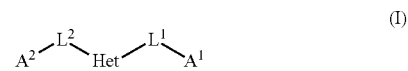

(I)

Het can be a substituted or unsubstituted bivalent heterocyclic group. $L^1$ can be a bond, or substituted or unsubstituted bivalent $C_1$-$C_2$ alkane. $L^1$ can be straight-chained or branched-chain. $L^2$ can be a substituted or unsubstituted bivalent $C_3$-$C_5$ alkane, where one or more of the carbons of the bivalent $C_3$-$C_5$ alkane can be replaced with one or more heteroatoms, such as N, S, O, or P. $L^2$ can be straight-chained or branched-chain. $A^1$ and $A^2$ can be the same or different and can be substituted or unsubstituted aryl groups or substituted or unsubstituted aromatic heterocyclic groups (e.g., univalent radicals of indole, benzofuran, benzothiophene, naphthalene, quinoline, pyridine, or thiophene).

In some embodiments, $L^1$ is a bond or methylene. In other embodiments, $L^2$ is a bivalent straight-chained butane or

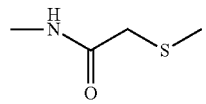

In some embodiments, $A^1$ and $A^2$ is a substituted or unsubstituted univalent bicyclic or heterocyclic group. For example, $A^1$ and $A^2$ can be a substituted or unsubstituted univalent five-membered heterocyclic group (such as thiazole, thiadiazole), a substituted or unsubstituted univalent six-membered heterocyclic group (such as pyridine, pyrimidine), a substituted or unsubstituted univalent bicyclic group (such as indole, indan, quinoline, isoquinoline, benzothiazole), or a substituted or unsubstituted univalent tricyclic group (such as anthracene, acridine). In some instances, a methyl, a methoxy, or combinations thereof can be placed at one or both meta positions to the attachment point. Also, $A^1$ and $A^2$ can be substituted with $CF_3$ or F.

In some embodiments, $A^2$ can be a substituted or unsubstituted univalent radical of the following: 9-Aminoacridine, 1-Aminoanthracene, 2-Aminoanthracene, 2-Aminobenzimidazole, 4-Amino-2,1,3-benzothiadiazole, 2-Aminobenzothiazole, 6-Aminobenzothiazole, 5-Aminobenzotriazole, 2-Aminobiphenyl, 2-Amino-5-bromobenzothiazole, 2-Amino-6-bromobenzothiazole, 2-amino-5-bromo-3,4-dimethylpyridine, 2-amino-5-bromo-4-hydroxy-6-methylpyrimidine, 2-amino-3-bromo-5-methylpyridine, 6-amino-3-bromo-2-methylpyridine, 3-amino-4-chloro-benzotrifluoride, 5-amino-2-chloro-benzotrifluoride, 2-amino-4-chloro-6-methylpyrimidine, 2-amino-4,6-dimethoxypyrimidine, 2-amino-4,6-dimethylpyrimidine, 2-amino-6-ethoxy-benzothiazole, 2-amino-4-ethylpyridine, 2-amino-6-ethylpyridine, 2-amino-6-fluorobenzothiazole, 3-amino-2-fluorobenzotrifluoride, 3-amino-4-fluorobenzotrifluoride, 5-aminoindazole, 5-aminoindan, 5-aminoindole, 5-aminoisoquinoline, 5-amino-2-methylindole, 5-amino-3-methylisoxazole, 2-amino-4-methylpyridine, 2-amino-4-methylpyrimidine, 2-amino-5-methylthiazole, 3-aminoquinoline, 5-aminoquinoline, 6-aminoquinoline, and 8-aminoquinoline.

$A^1$ can be as-shown, substituted, or further substituted versions of the following radicals

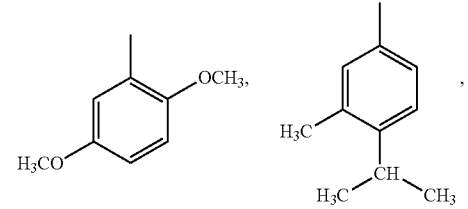

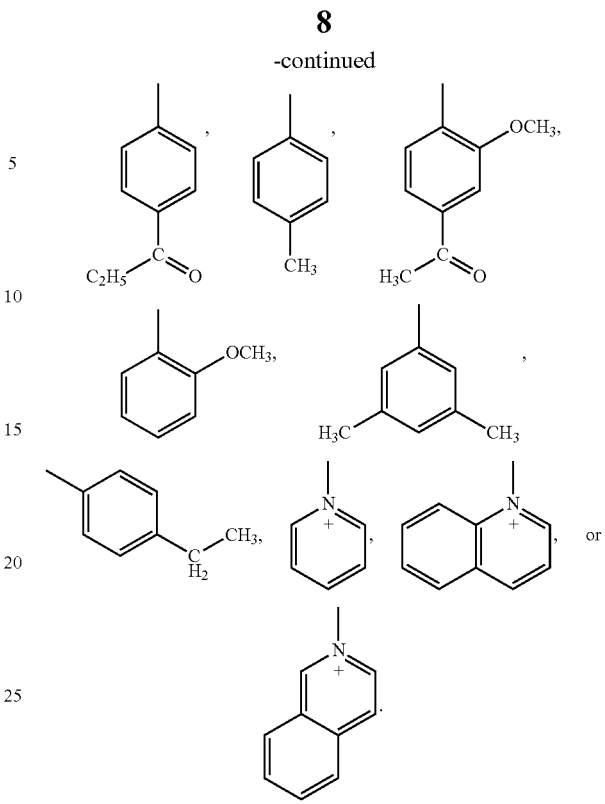

$A^2$ can be as-shown, substituted, or further substituted versions of the following radicals

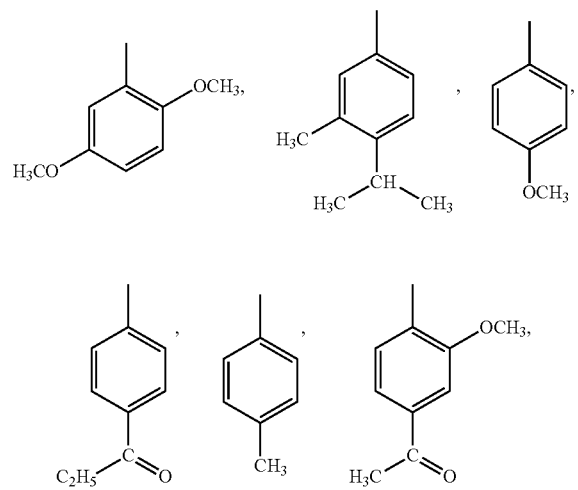

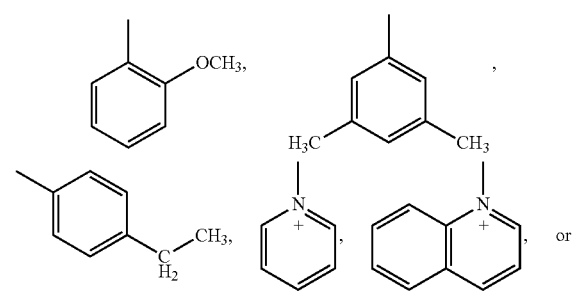

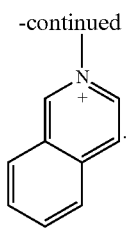

In some instances, $A^1$ is

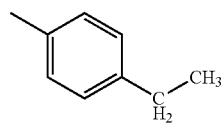

and $A^2$ is

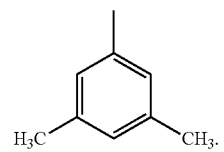

Het can be a five- or six-membered heterocyle. Where prototropic hydrogens exist on the heterocycle, structural depictions are understood to include the tautomeric forms. In some instances, Het is unsubstituted. In some embodiments, Het is a bivalent substituted

or a bivalent unsubstituted

such as

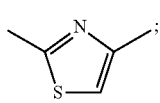

a bivalent substituted

or a bivalent unsubstituted

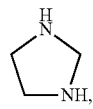

such as

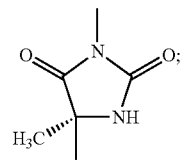

a bivalent substituted

or a bivalent unsubstituted

such as

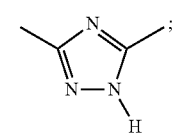

a bivalent substituted

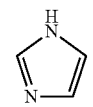

or a bivalent unsubstituted

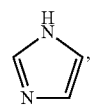

such as
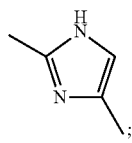
a bivalent further substituted
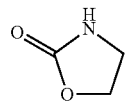
or bivalent unsubstituted
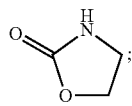
a bivalent substituted
or bivalent unsubstituted
a bivalent substituted
or a bivalent unsubstituted
a bivalent further substituted
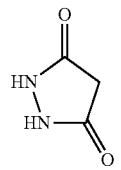
or a bivalent unsubstituted
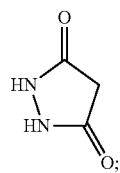
a bivalent substituted
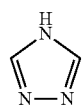
or a bivalent unsubstituted
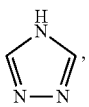
such as
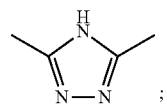
a bivalent substituted
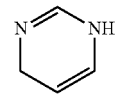
or a bivalent unsubstituted
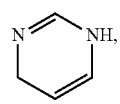
such as
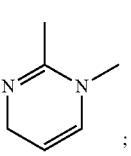

a bivalent substituted

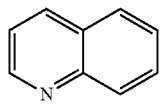

or a bivalent unsubstituted

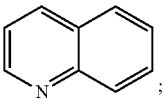;

or
a bivalent substituted

or a bivalent unsubstituted

.

In another embodiment, formula (I) is

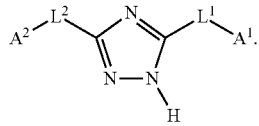

including the 1H, 2H, and 4H tautomeric forms thereof:

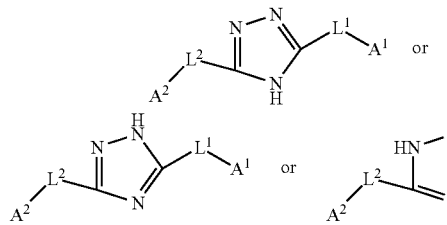

In still other embodiments, Formula (I) can be

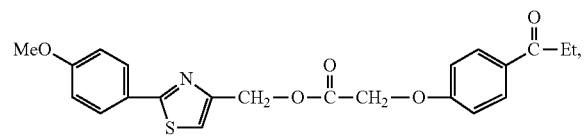

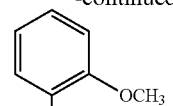

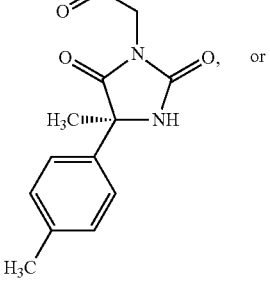

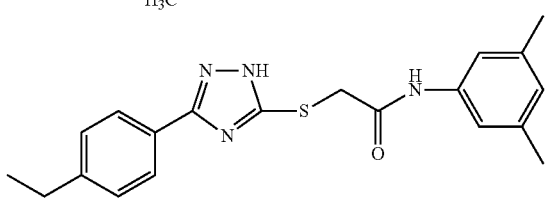

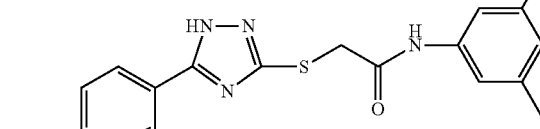

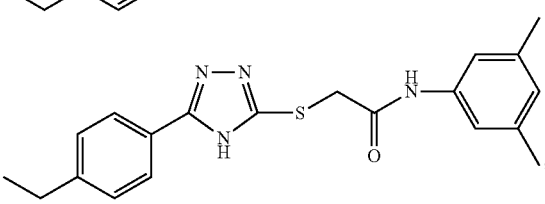, which are N-(3,5-dimethylphenyl)-2-[[5-(4-ethylphenyl)-1H-1,2,4-triazol-3-yl]sulfanyl]acetamide, N-(3,5-dimethylphenyl)-2-[[5-(4-ethylphenyl)-2H-1,2,4-triazol-3-yl]sulfanyl]acetamide, and N-(3,5-dimethylphenyl)-2-[[5-(4-ethylphenyl)-4H-1,2,4-triazol-3-yl]sulfanyl]acetamide, and which are the triazole tautomers of the compound referred to herein as CK37.

Formula (II) is

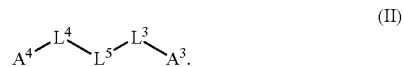 (II)

$L^3$ can be a substituted or unsubstituted bivalent $C_1$-$C_3$ alkane, where one or more of the carbons of the bivalent $C_1$-$C_3$ alkane can be replaced with one or more heteroatoms, such as N, S, O, or P. $L^3$ can be straight-chained or branched-chained. $L^4$ can be a substituted or unsubstituted bivalent $C_1$-$C_4$ alkane, where one or more of the carbons of the bivalent $C_1$-$C_4$ alkane can be replaced with one or more heteroatoms, such as N, S, O, or P. $L^4$ can be straight-chained or branched-chained. $A^3$ and $A^4$ can be the same or different and can be substituted or unsubstituted aryl groups or substituted or unsubstituted aromatic heterocycle groups (e.g., univalent radicals of indole, benzofuran, benzothiophene, naphthalene, quinoline, pyridine, or thiophene). L⁵ can be the substituted or unsubstituted bivalent

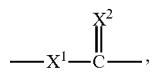

where $X^1$ can be C, or N, S, O, or P; and $X^2$ can be N, S, O, P, or C. $X^1$ can be the same as or different from $X^2$. In some embodiments, $X^1$ is O and $X^2$ is O; $X^1$ is N and $X^2$ is N; $X^1$ is O and $X^2$ is N; $X^1$ is N and $X^2$ is O; $X^1$ is N and $X^2$ is S; $X^2$ is S; or $X^2$ is C.

In some embodiments, $L^3$ is —NH—; —CH$_2$O—; —CH$_2$S—; or —CH$_2$CH$_2$—. In some embodiments, $L^4$ is —CH$_2$—, —COCH$_2$—,

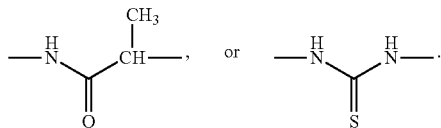

In some embodiments, $A^3$ and $A^4$ is a substituted or unsubstituted univalent bicyclic or heterocyclic group. For example, $A^3$ and $A^4$ can be a substituted or unsubstituted univalent five-membered heterocyclic group (such as thiazole, thiadiazole), a substituted or unsubstituted univalent six-membered heterocyclic group (such as pyridine, pyrimidine), a substituted or unsubstituted univalent bicyclic group (such as indole, indan, quinoline, isoquinoline, benzothiazole), or a substituted or unsubstituted univalent tricyclic group (such as anthracene, acridine). In some instances, a methyl, a methoxy, or combinations thereof can be placed at one or both meta positions to the attachment point. Also, $A^3$ and $A^4$ can be substituted with CF$_3$ or F.

In some embodiments, $A^3$ and $A^4$ can be a substituted or unsubstituted univalent radical of the following: 9-Aminoacridine, 1-Aminoanthracene, 2-Aminoanthracene, 2-Aminobenzimidazole, 4-Amino-2,1,3-benzothiadiazole, 2-Aminobenzothiazole, 6-Aminobenzothiazole, 5-Aminobenzotriazole, 2-Aminobiphenyl, 2-Amino-5-bromobenzothiazole, 2-Amino-6-bromobenzothiazole, 2-amino-5-bromo-3,4-dimethylpyridine, 2-amino-5-bromo-4-hydroxy-6-methylpyrimidine, 2-amino-3-bromo-5-methylpyridine, 6-amino-3-bromo-2-methylpyridine, 3-amino-4-chloro-benzotrifluoride, 5-amino-2-chloro-benzotrifluoride, 2-amino-4-chloro-6-methylpyrimidine, 2-amino-4,6-dimethoxypyrimidine, 2-amino-4,6-dimethylpyrimidine, 2-amino-6-ethoxy-benzothiazole, 2-amino-4-ethylpyridine, 2-amino-6-ethylpyridine, 2-amino-6-fluorobenzothiazole, 3-amino-2-fluorobenzotrifluoride, 3-amino-4-fluorobenzotrifluoride, 5-aminoindazole, 5-aminoindan, 5-aminoindole, 5-aminoisoquinoline, 5-amino-2-methylindole, 5-amino-3-methylisoxazole, 2-amino-4-methylpyridine, 2-amino-4-methylpyrimidine, 2-amino-5-methylthiazole, 3-aminoquinoline, 5-aminoquinoline, 6-aminoquinoline, and 8-aminoquinoline.

$A^3$ can be as-shown, substituted, or further substituted versions of the following radicals

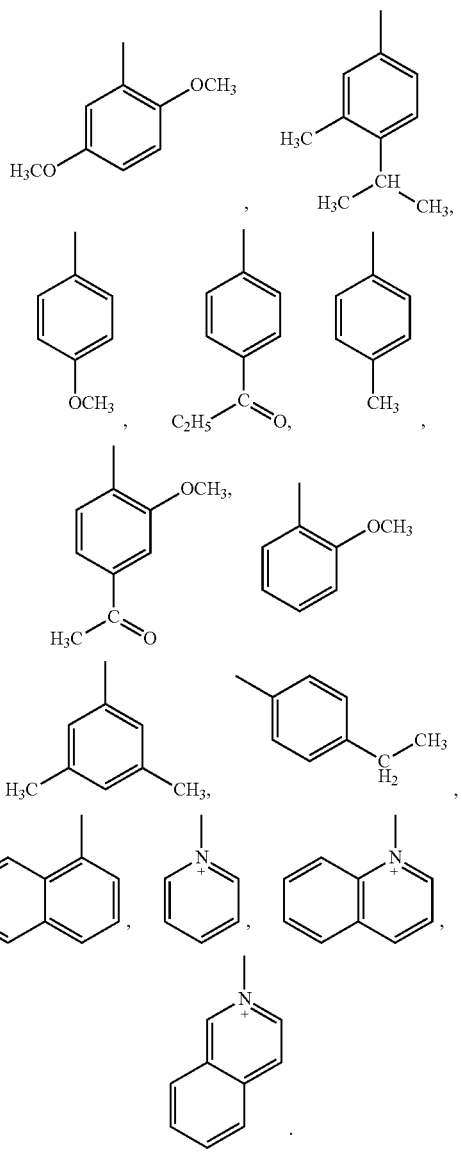

$A^4$ can be as-shown, substituted, or further substituted versions of the following radicals

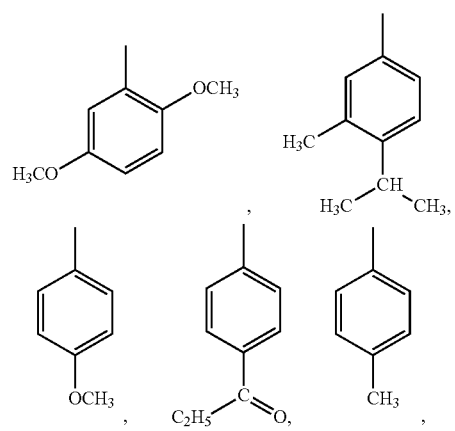

-continued

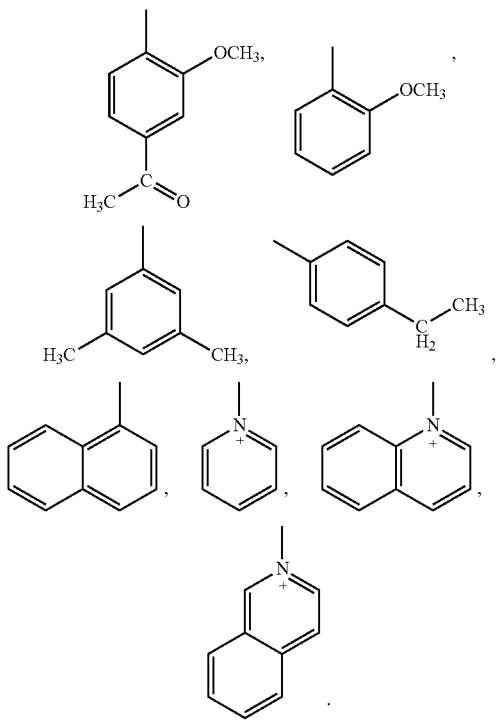

In some embodiments, Formula (II) is

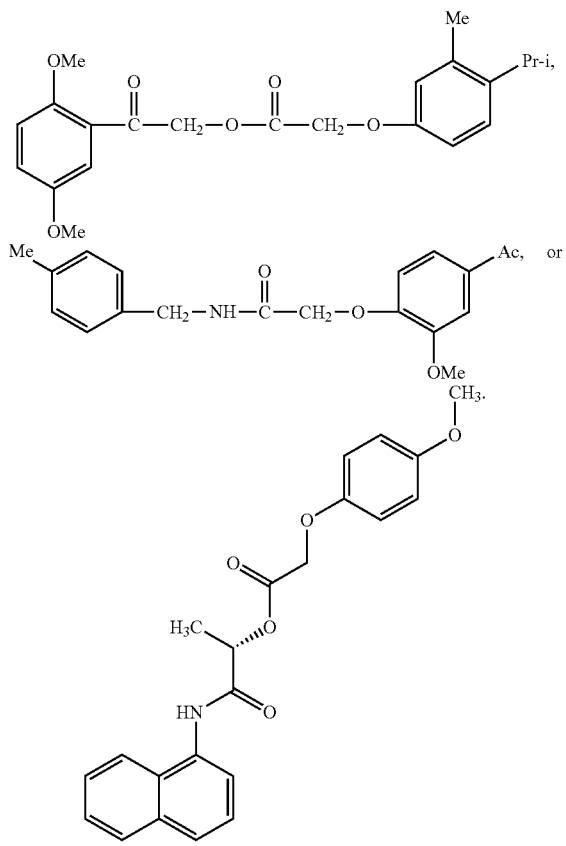

In some embodiments, Formula (II) is

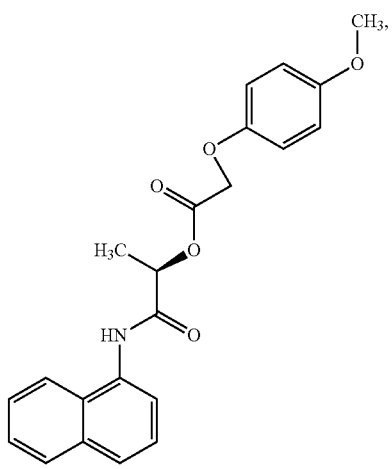 [SMILES: COc1ccc(OCC(=O)O[C@H](C)C(=O)Nc2cccc3ccccc23)cc1]

referred to herein as CP6.

The compounds described herein (e.g., those of Formula (I) and Formula (II)) can interact with the choline kinase binding pocket. The binding pocket of choline kinase that determines recognition (e.g., specificity and binding strength) of the compounds can be comprised of the following amino acid residues (numbered according to the 2CKQ.pdb sequence, set forth herein as SEQ ID NO: 1): ILE116, ARG117, GLY118, GLY119, LEU120, SER121, ASN122, MET123, LEU124, ARG146, ARG256, ASN305, ASP306, GLN308, GLY310, ASN311, ILE323, ASP330, GLU332, TYR333, ASN345, CYS348, GLU349, TYR354, SER416, TRP420, TRP422, TRP423, GLN427, TYR440, and ARG444. The interaction pocket that binds the compounds is a 5 angstrom pocket. There can be multiple hydrogen bonds (e.g., 1, 2, 3, 4, 5, or 6 hydrogen bonds) from the non-carbon atoms in the linker region (e.g., one or more of $L^1$, $L^2$, $L^3$, $L^4$, $L^5$, or Het) of the compound to amino acid residues in the binding pocket choline kinase; these hydrogen bonds can occur on the amino acid side chain, on the protein backbone, or both. Hydrogen bonds between the compound and the choline kinase binding pocket may include (but are not limited to) the following residues: LEU 120, SER 121, ASN 122, ASP 306, and ASP 330.

CK37 appears to form six hydrogen bonds with the binding pocket of choline kinase. In CK37, hydrogen bonds are formed from (a) the CK37 amide carbonyl oxygen atom to the backbone amide nitrogen of ASN 122, (b) the CK37 amide nitrogen to the carboxylic oxygen of ASP 330, (c) the CK37 triazole ring NH to ASP 306 and to the SER 121 OH group, and (d) CK37 triazole non-protonated nitrogen atoms individually to the backbone amide nitrogens of LEU 120 and SER 121. CP6 appears to form four hydrogen bonds with the binding pocket of choline kinase. In the case of CP6, hydrogen bonds are formed from (a) the CP6 amide carbonyl oxygen atom to the backbone amide nitrogens of SER 121 and ASN 122, (b) the CP6 ester ether oxygen to the hydroxyl of the side chain of SER 121, and (c) the ester carbonyl oxygen atom to the carbonyl oxygen atom of ASP 306.

Compounds according to Formulae (I) or (II) (e.g., CK37 or CP6) can be used to modulate choline kinase in vitro, in situ, or in vivo, such as in an animal. Modulation can be, for example, an increase or decrease in the activity or expression of choline kinase. Modulation can occur directly, indirectly, or both.

The compounds of Formula (I) or (II) (e.g., CK37 or CP6) can be administered to animals by any number of administration routes or formulations. The compounds can also be used to treat animals for a variety of diseases. Animals include but are not limited to canine, bovine, porcine, avian, mammalian, and human.

Diseases that can be treated or cured using the compounds (e.g., CK37 or CP6) can be those related to or affected by choline kinase, including, for example, those diseases related to or affected by the inhibition of choline kinase. Diseases that can be treated or cured using the compounds (e.g., CK37 or CP6) include but are not limited to treatment of infections (e.g., mycobacterial infections such as infections associated with tuberculosis, gram-negative bacterial infections, gram positive bacterial infections, fungal infections), cardiovascular diseases, cancer, endocrinological diseases, metabolic diseases, gastroenterological diseases, inflammation, hematological diseases, respiratory diseases, muscle skeleton diseases, neurological diseases, and urological diseases. The treatment of cancer can include, but is not limited to, treatment of breast cancer, colon cancer, lung cancer, cervical cancer, melanoma, lymphoma, and leukemia (e.g., acute or chronic lymphocytic leukemias (sometime called lymphoblastic), or acute or chronic myelogenous leukemias (sometimes called myeloid). For example, the compounds can be used as (or as part of) a chemotherapeutic strategy. Treatment can include the treatment of tumors and growths associated with cancers. The treatment can include treatments that have anti-neoplastic effects.

The route of administration of the compounds (e.g., CK37 or CP6) may be of any suitable route such as that which provides a concentration in the blood corresponding to a therapeutic concentration. Administration routes that can be used, but are not limited to the oral route, the parenteral route, the cutaneous route, the nasal route, the rectal route, the vaginal route and the ocular route. The choice of administration route can depend on the compound identity, such as the physical chemical properties of the compound, as well as the age and weight of the animal, the particular disease, and the severity of the disease. Of course, combinations of administration routes can be administered, as desired.

The compounds of Formula (I) or (II) (e.g., CK37 or CP6) can be part of a pharmaceutical composition and can be in an amount from about 1% to about 95% by weight of the total composition (or from about 10% to about 90%, or from about 25% to about 75%). The composition can be presented in a dosage form which is suitable for the oral, parenteral, rectal, cutaneous, nasal, vaginal, or ocular administration route. The composition can be of the form of, for example, tablets, capsules, pills, powders granulates, suspensions, emulsions, solutions, gels (including hydrogels), pastes, ointments, creams, plasters, drenches, delivery devices, suppositories, enemas, injectables, implants, sprays, aerosols or other suitable forms.

Pharmaceutical compositions can be formulated to release the active compound substantially immediately upon the administration or any substantially predetermined time or time after administration. Such formulations can include, for example, controlled release formulations such as various controlled release compositions and coatings. Such formulations also include pro-drug principles, such as converting the active drug substance into an inactive derivative; when the pro-drug is administered to the organism, the organism converts the pro-drug to the active drug (e.g., by an enzymatic or non-enzymatic process) so the active drug can exert its therapeutic effect.

Other formulations include those incorporating the drug (or control release formulation) into food, food stuffs, feed, or drink.

The compounds of Formula (I) or (II) (e.g., CK37 or CP6) can be in the form of salts, optical and geometric isomers, and salts of isomers, and may exist as tautomers in a tautomeric equilibrium according to properties of solvents, temperature, pH and/or and ionic properties of proximal substituents, for example proximity of electron-withdrawing groups to the prototropic hydrogen. In particular, N-heterocycles are known to exist as annular tautomers, and specifically in protropic triazoles the hydrogen may exist as 1H, 2H, or 4H of 1,2,4-triazole or may exist in tautomeric equilibrium between any combination of these, depending on, for example, solvent conditions. Compounds of the invention comprising substituted triazoles may exist as one tautomeric form, or a mixture of the tautomers. A person of ordinary skill in the art may readily shift the equilibrium to a desired tautomeric ration. For example, under a particular ionic state/condition, tautomeric equilibrium may be shifted by manipulation of substituents at proximate positions. Also, the compounds can be in various forms, such as uncharged molecules, components of molecular complexes, or non-irritating pharmacologically acceptable salts, e.g. the hydrochloride, hydrobromide, sulphate, phosphate, nitrate, borate, acetate, maleate, tartrate, salicylate, etc. For acidic compounds, salts include metals, amines, or organic cations (e.g. quaternary ammonium). Furthermore, simple derivatives of the compounds (such as ethers, esters, amides, etc.) which have desirable retention and release characteristics but which are easily hydrolyzed by body pH, enzymes, etc., can be employed.

The methods of treating an organism will involve treatment with an amount of the compound (e.g., CK37 or CP6) that is effective to treat the disease, condition, or disorder that the organism has, or is suspected of having, or to bring about a desired physiological effect. In some cases, this amount will be less than the amount of HC-3 or any of the HC-3 derivatives used to treat a comparable disease, condition, or disorder or to bring about a comparable desired physiological effect. In some embodiments, the amount of the compound is administered to mammals (e.g., humans) at a concentration of about 0.05 to about 500 mg/kg body weight, about 0.05 to about 250 mg/kg body weight, about 0.05 to about 15 mg/kg body weight, about 0.2 to about 10 mg/kg body weight, about 0.5 to about 7 mg/kg body weight, about 0.5 mg/kg, about 1 mg/kg, about 3 mg/kg, about 5 mg/kg, about 5.5 mg/kg, about 6 mg/kg, about 6.5 mg/kg, about 7 mg/kg, about 7.5 mg/kg, about 8 mg/kg, about 10 mg/kg, about 12 mg/kg, about 15 mg/kg, about 50 mg/kg, about 100 mg/kg, about 200 mg/kg, about 250 mg/kg, about 300 mg/kg, about 400 mg/kg, or about 500 mg/kg. In regard to some conditions, the dosage will be about 6.5 mg/kg human body weight. In some instances, a mouse can be administered a dosage of about 80 mg/kg, about 50 mg/kg, about 100 mg/kg, about 150 mg/kg, about 250 mg/kg, about 350 mg/kg, or about 500 mg/kg. The compounds of the invention can be administered in combination with one or more other therapeutic agent for a given disease, condition, or disorder.

The following Examples are provided to illustrate certain aspects and embodiments of the invention and should not be construed as limiting the scope of the invention as defined by the claims herein.

EXAMPLES

General Methodology

The following are descriptions of experimental methodologies associated with certain of the illustrative Examples which follow.

Cell Culture—

HeLa (ATCC: CCL-2), A549-human lung carcinoma (ATCC: CCL-185), Lewis lung carcinoma (LLC) (ATCC: CRL-1642), and melanoma cells (ATCC: CRL-11147) were cultured in DMEM (Hyclone) supplemented with 10% fetal bovine serum (Hyclone) and 50 μg/mL gentamicin sulfate (Invitrogen). Jurkat leukemia cells were cultured in RPMI (Hyclone) supplemented with 10% fetal bovine serum and 50 μg/mL gentamicin sulfate. Human mammary epithelial cells were grown in mammary epithelial basal medium (Lonza) supplemented according to manufacturer's protocol. All cell lines were maintained at 5% $CO_2$ at 37° C.

Choline Kinase Activity—

Choline kinase activity was assayed as described previously in Hernandez-Alcoceba et al. "Choline kinase inhibitors as a novel approach for antiproliferative drug design," Oncogene 1997, 15:2289-2301, the disclosure of which is incorporated herein by this reference. For HeLa cell lysate, equal volume of lysate was incubated in the presence or absence of the tested compound in kinase assay buffer (100 mM Tris-HCl, 100 mM $MgCl_2$, 10 mM ATP, 200 μM choline, and 2 μM methyl[$^{14}$C]-choline chloride (50-60 μCi, mmol). Reactions were carried out at 37° C. for one hour and immediately stopped by addition of TCA (Trichloroacetic Acid) to a final concentration of 16%. The TCA soluble fraction was then washed 3× with four volumes of water saturated ethyl ether, and dried under vacuum. Metabolites were separated by thin layer chromatography using 60 Å silica gel plates and a liquid phase consisting of 0.9% NaCl:methanol:ammonium hydroxide (50:70:5; V:V:V). Radioactive images were resolved by PhosphorImager screening and densitometry was performed using Image Quant software.

Human recombinant choline kinase was purified from E. Coli bacterial cultures via thrombin cleavage of expressed GST-tagged choline kinase. The expression construct was generously gifted by Arnon Lavie at the University of Illinois. Equal volume of recombinant choline kinase was incubated in the presence or absence of the tested compound in kinase assay buffer (100 mM Tris-HCl, 100 mM $MgCl_2$, 10 mM ATP, and 2 μM methyl[$^{14}$C]-choline chloride (50-60 μCi, mmol). Reactions were carried out at 37° C. for one hour and immediately stopped by addition of TCA (Trichloroacetic Acid) to a final concentration of 16%. The TCA soluble fraction was then washed 3× with four volumes of water saturated ethyl ether, and dried under vacuum. Metabolites were separated by thin layer chromatography using 60 Å silica gel plates and a liquid phase consisting of 0.9% NaCl:methanol:ammonium hydroxide (50:70:5; V:V:V). Radioactive images were resolved by PhosphorImager screening and densitometry was performed using Image Quant software.

For HeLa cell labeling, cells were seeded at $1\times10^5$ cells/mL and incubated with increasing concentrations of the tested compound for 48 hours. Methyl[$^{14}$C]-choline chloride was added 24 hours before cell harvest, and cells were extracted and analyzed as described above. Densitometry units were normalized to total protein levels for each sample.

NMR Measurement of Choline Metabolites—

HeLa cells were seeded at $1\times10^5$ cells/mL and treated with either 10 μM or 50 μM CK37 for 12 hours. Cells were then extracted twice with 300 μL trichloroacetic acid (TCA) and combined supernatants (total 600 μL) were lyophilized for 48 hours. Dried samples were re-suspended in 100% $D_2O$ with addition of DSS (2,2-Dimethyl-2-silapentane-5-sulfonic acid) standard and placed in Shigemi 5 mm NMR tubes for analysis.

NMR spectra were recorded at 20° C. on a 14.1 T Varian Inova NMR spectrometer equipped with an inverse triple resonance cold probe. One dimension $^1H$ spectra were recorded using an acquisition time of 2 sec and a recycle time of 5 sec; 256 transients were collected. Peaks areas of the phosphocholine resonance at 3.22 ppm, the valine methyl, the lactate methyl, the threonine methyl, and DSS were measured using the Varian VNMR software. Where necessary, small corrections for partial saturation were made as described previously using measured $T_1$ values (Lane et al., "Isotopomer-based metabolomic analysis by NMR and mass spectrometry," Methods in Cell Biol. (2008) Vol. 84, pp. 541-588). The concentration of phosphocholine was then estimated from the ratio of its peak area normalized either to DSS or to the valine methyl. The former requires a further correction for the number of cells in each sample, whereas valine (or threonine) is an internal standard whose concentration does not change significantly over time (Fan et al., "Rhabdomyosarcoma cells show an energy producing anabolic metabolic phenotype compared with primary myocytes," Molecular Cancer (Oct. 21, 2008) Vol. 7, Article No. 79).

Cell Growth Inhibition—

All cell lines were plated at $1\times10^5$/mL in the appropriate medium. For suspension cells, the tested compound was added immediately to the medium, whereas the tested compound treatment was initiated the following day for adherent cell lines. For overexpression studies, HeLa cells were transiently transfected with empty vector or vector containing wild type choline kinase twenty-four hours prior to addition of increasing concentrations of CK37. Cells were then collected 48 h after treatment, and cell number and viability were determined by trypan blue exclusion. $IC_{50}$s were calculated at the tested compound concentration needed for 50% of vehicle-treated cell growth (see Table 4). The data represented are the mean±STD from triplicate measurements from three independent experiments.

Soft Agar Colony Formation—

HeLa cells were plated at a density of $25\times10^3$ cells per 60-mm plate with 3 mL bottom agar (0.6%) and 2 mL top agar (0.3%) in normal growth medium. Cells were fed every three days by addition of a new layer of top agar which contained increasing concentrations of the tested compound. After 14 days of growth, colonies were counted in random from 1 cm squared sections of each plate.

ERK1/2 Phosphorylation—

HeLa cells were treated in the absence or presence of increasing concentrations of the tested compound. Protein extraction and western blotting was performed as described previously in Telang et al. "Ras transformation requires metabolic control by 6-phosphofructo-2-kinase" Oncogene 2006, 25:7225-7234, the disclosure of which is incorporated herein by this reference. Blots were probed for p-ERK1/2, total ERK1/2, and β-actin using anti-pERK1/2, anti-ERK1/2, and anti-actin antibodies, respectively.

Actin/Cytoskeleton and Focal Adhesion Immunofluorescence—

HeLa cells were grown on slide coverslips and treated in the absence or presence of 10 μM the tested compound for 48 hours. Staining of the actin cytoskeleton and focal adhesion points was performed following the manufacturer's protocol (Millipore). Briefly, cells were fixed with 4% paraformaldehyde and permeabilized with addition of 0.1% Triton X. The vinculin focal adhesion protein was visualized using α-vinculin antibody followed by α-rat AlexaFluor 488 secondary antibody. F-actin was assayed by addition of TRITC-conjugated phalloidin. Immunofluorescence images were generated using the Olympus BX51WI confocal microscope with Fluoview software.

Electron Microscopy—

HeLa or MDA-MB-231 cells were treated in the absence or presence of 10 µM the tested compound for 48 hours. Samples were fixed in cacodylate buffered 3% glutaraldehyde for 16 hours at 4° C. They were subsequently postfixed in cacodylate buffered 1% osmium tetroxide for one hour, dehydrated through a series of graded alcohols, and embedded in LX-112 epoxy plastic (Ladd Research Industries). 80 µM sections were cut on a LKB 8800 ultratone utilizing a diamond knife, mounted on 200 mesh copper grids, stained with uranium acetate and lead citrate, and viewed with a Phelps CM 12 electron microscope operating at 60 KV.

Mouse Tumors—

Exponentially growing Lewis lung carcinoma cells were collected, washed twice, and resuspended in PBS ($1\times10^7$/mL). C57B1/6 female mice (20 g) were injected s.c. with 0.1 mL of the suspension. Body weight and tumor growth were monitored daily throughout the study. Tumor masses were determined by measurement with Vernier calipers using the formula: mass (mg)=[width$^2$ (mm)×length (mm)]/2. Mice with established tumors (between 130 and 190 mg) were randomized into vehicle control or the tested compound treated groups. Vehicle control groups received i.p. injections of 50 µL DMSO, whereas treated groups received 0.08 mg/g the tested compound in 50 µL DMSO at the indicated time points. All protocols were approved by the University of Louisville Institutional Animal Care and Use Committee.

Statistics—

Statistical significance for the choline kinase inhibition, growth and soft agar colony formation inhibition, and in vivo studies between control and the tested compound treatment was determined by a two-sample, nonparametric, two-tailed t test using Graph Pad Prism version 3.0 (Graph Pad Software). $p<0.05$ was considered to be statistically significant.

Example 1

Computational Screening for Small Molecule Inhibitors of Choline Kinase

In mammalian cells, there exist three isoforms of choline kinase which are encoded by two separate genes, choline kinase-α and choline kinase-β. Two functional isoforms of choline kinase result from alternative splicing of the choline kinase-α transcript. Homodimeric and heterodimeric forms of choline kinase confer the kinase activity that phosphorylates free choline to phosphocholine. The available crystal structure of splice isoform 2 of choline kinase with phosphocholine bound (pdb entry 2CKQ) was used in our virtual screen. The difference in the splice isoforms 1 and 2 are not in the ATP or phosphocholine binding site, the dimer interface, the Brenner's motif, or the choline kinase motif as these are 100% conserved. Isoform 2 has an additional 18 residues starting at residue 155 which do not appear to be involved in these binding sites.

Utilizing the recently described X-ray structure of human choline kinase, we performed an in silico screen, as described herein, of the ZINC Library to identify potential choline kinase interacting compounds. Specifically, the crystal structure 2CKQ (with the phosphocholine removed) was used for virtual screening targeting of the phosphocholine binding site. The water molecules were stripped from the structure and the target site was the area surrounding phosphocholine. The phosphocholine molecule was stripped but was used to create a ligand-based protomol, with proto_thresh set at 0.2 and proto_bloat at 1, for Surflex-Dock. The 2007 ZINC "all purchasable" library containing 2,667,437 compounds was used with Surflex-Dock to generate a ranked list of candidates. All computational set up and analysis of the virtual screening was done in the JG Brown Cancer Center Molecular Modeling Facility. The University of Louisville JG Brown Cancer Center Molecular Modeling Facility used the Kentucky Dataseam Distributed Grid to perform the actual virtual screening docking calculations.

Using this in silico screen, the 50 highest ranked molecules were identified, scored, ranked, and analyzed based on their association potential with the active site within choline kinase. The sixteen best-score compounds were purchased from Enamine (of Monmouth Jct., N.J. and Kiev, Ukraine) and tested for their ability to inhibit choline kinase activity in vitro. The sixteen compounds are provided in Table 1 below.

TABLE 1

| Labels in FIG. 1A (with Identifying Numbers) | Chemical Structures and Names |
| --- | --- |
| A (CAS No. 1007741-39-0) | (5S)-3-[2-(2,4-dimethoxyphenyl)-2-oxoethyl]-5-ethyl-5-phenylimidazolidine-2,4-dione |

TABLE 1-continued

| Labels in FIG. 1A (with Identifying Numbers) | Chemical Structures and Names |
|---|---|
| B (Pubchem: 7793283; Zinc: 5776466) | 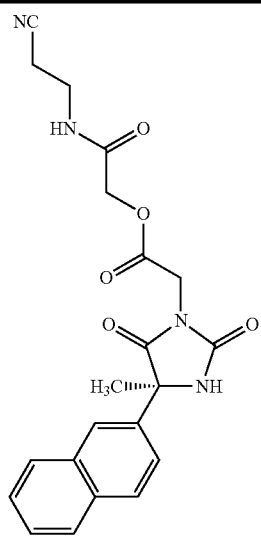 [2-(2-cyanoethylamino)-2-oxoethyl] 2-[(4S)-4-methyl-4-naphthalen-2-yl-2,5-dioxoimidazolidin-1-yl]acetate |
| C (CAS No. 1030732-26-3) | 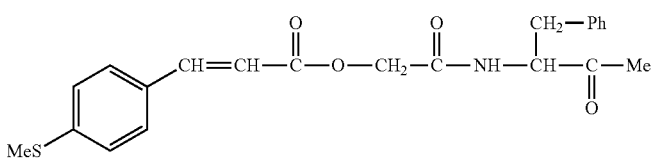 [2-oxo-2-[[(2R)-3-oxo-1-phenylbutan-2-yl]amino]ethyl] (E)-3-(4-methylsulfanylphenyl)prop-2-enoate |
| D (CAS No. 1002698-13-6) | 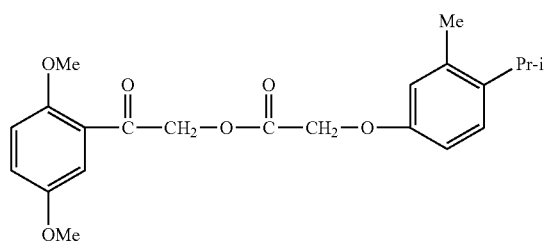 [2-(2,5-dimethoxyphenyl)-2-oxoethyl] 2-(3-methyl-4-propan-2-ylphenoxy)acetate |
| E (CAS No. 849183-27-3) | 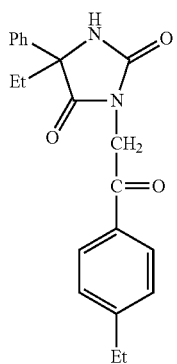 (5S)-5-ethyl-3-[2-(4-ethylphenyl)-2-oxoethyl]-5-phenylimidazolidine-2,4-dione |

TABLE 1-continued
| Labels in FIG. 1A (with Identifying Numbers) | Chemical Structures and Names |
|---|---|
| F (CP6) (CAS No. 950148-91-1) | 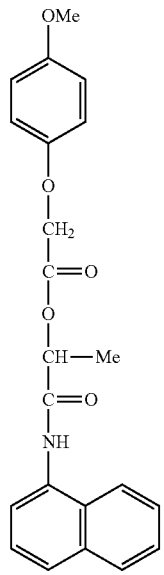<br>[(2R)-1-(naphthalen-1-ylamino)-1-oxopropan-2-yl] 2-(4-methoxyphenoxy) acetate |
| G (CAS No. 950092-17-8) | 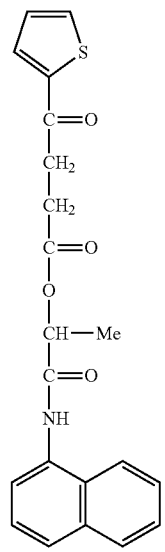<br>[(2R)-1-(naphthalen-1-ylamino)-1-oxopropan-2-yl] 4-oxo-4-thiophen-2-ylbutanoate |

TABLE 1-continued

| Labels in FIG. 1A (with Identifying Numbers) | Chemical Structures and Names |
|---|---|
| H (PubChem: 7709976; Zinc: 5485444) | 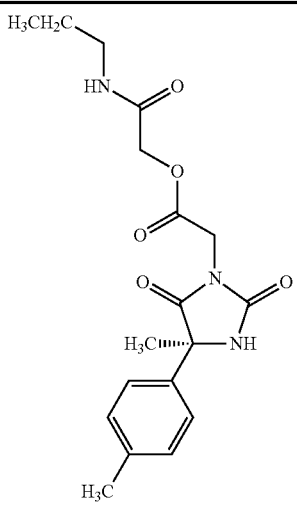<br>[2-oxo-2-(propylamino)ethyl] 2-[(4R)-4-methyl-4-(4-methylphenyl)-2,5-dioxoimidazolidin-1-yl]acetate |
| I (CAS No. 950148-96-6) | 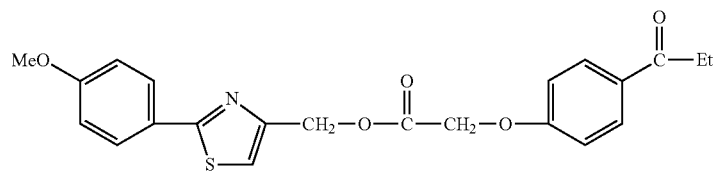<br>[2-(4-methoxyphenyl)-1,3-thiazol-4-yl]methyl 2-(4-propanoylphenoxy)acetate |
| J (CAS No. 002527-18-5) | 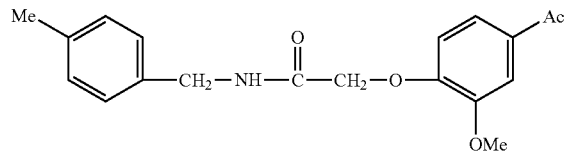<br>2-(4-acetyl-2-methoxyphenoxy)-N-[(4-methylphenyl)methyl]acetamide |
| K (CAS No. 1008200-67-6) | 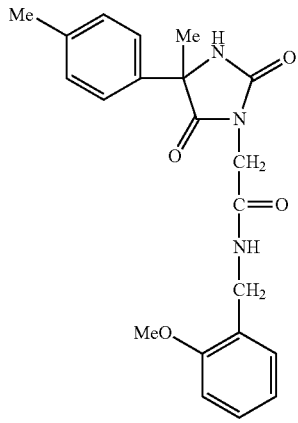<br>N-[(2-methoxyphenyl)methyl]-2-[(4S)-4-methyl-4-(4-methylphenyl)-2,5-dioxoimidazolidin-1-yl]acetamide |

TABLE 1-continued

| Labels in FIG. 1A (with Identifying Numbers) | Chemical Structures and Names |
|---|---|
| L (CAS No. 956205-31-5) | 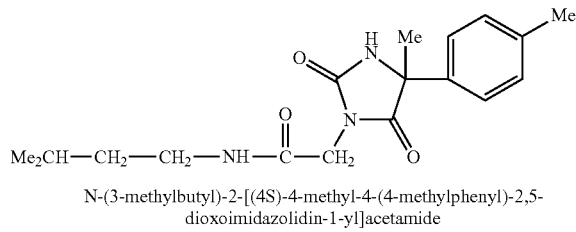 N-(3-methylbutyl)-2-[(4S)-4-methyl-4-(4-methylphenyl)-2,5-dioxoimidazolidin-1-yl]acetamide |
| M (CAS No. 956771-19-0) | 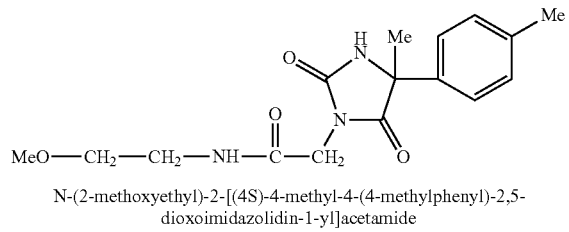 [SMILES: COCCNC(=O)CN1C(=O)NC(C)(c2ccc(C)cc2)C1=O] N-(2-methoxyethyl)-2-[(4S)-4-methyl-4-(4-methylphenyl)-2,5-dioxoimidazolidin-1-yl]acetamide |
| N (CK37) (CAS No. 1001478-90-5) | 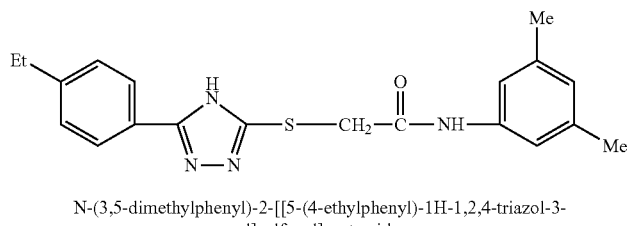 N-(3,5-dimethylphenyl)-2-[[5-(4-ethylphenyl)-1H-1,2,4-triazol-3-yl]sulfanyl]acetamide |
| O (CAS No. 1030731-22-6) | 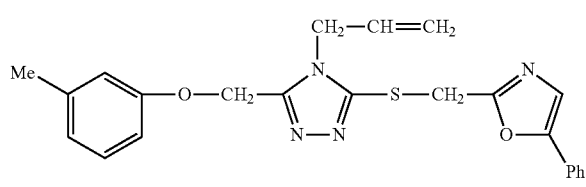 2-[[5-(3-methylphenoxy)methyl]-4-prop-2-enyl-1,2,4-triazol-3-yl]sulfanylmethyl]-5-phenyl-1,3-oxazole |
| P (Pubchem: 7710770; Zinc: 5486618) | 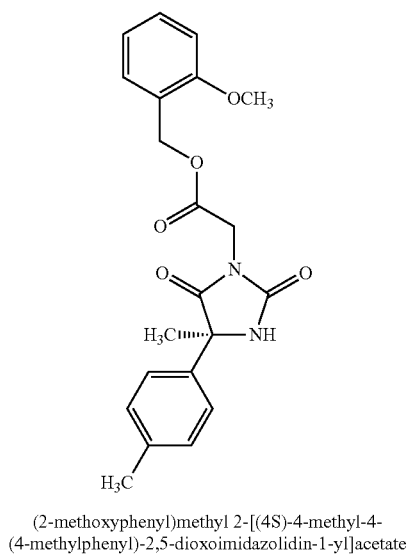 [SMILES: COc1ccccc1COC(=O)CN1C(=O)N[C@@](C)(c2ccc(C)cc2)C1=O] (2-methoxyphenyl)methyl 2-[(4S)-4-methyl-4-(4-methylphenyl)-2,5-dioxoimidazolidin-1-yl]acetate |

Example 2

The compounds identified according to the molecular modeling screen detailed in Example 2 were carefully inspected in order to determine features of the compounds which correlated to desired functionality. Additional compounds were synthesized according to preliminary analysis and are set forth in Table 2, below. These compounds also fall within the formula I set forth above and were synthesized according to one of two schemes:

SCHEME-1

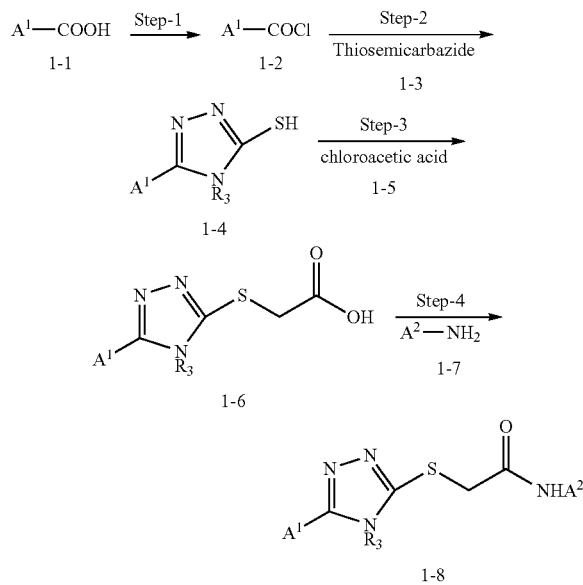

the mixture was extracted with ethyl acetate. Ethyl acetate was removed under vacuum to give the desired compound 1-6 as white solid (yield: 47-75%).

Step-4

1-(3-Dimethylaminopropyl)-3-ethylcarbodiimide hydrochloride (11.4 mmole) and 1-hydroxybenzotriazole (11.4 mmole) were added to a solution of compound 1-6 (9.5 mmole) in THF (250 mL). The reaction mixture was refluxed for 6 h and the desired amine (11.4 mmole) in THF (55 mL) was added and the reaction mixture was again refluxed for 3 h. Progress of the reaction was monitored by TLC (Ethyl acetate:Hexane-4:6). After completion of the reaction, the reaction mixture was concentrated and purified over a column of silica gel using an appropriate solvent to give the desired target 1-8 (Yield—40-80%).

SCHEME-2

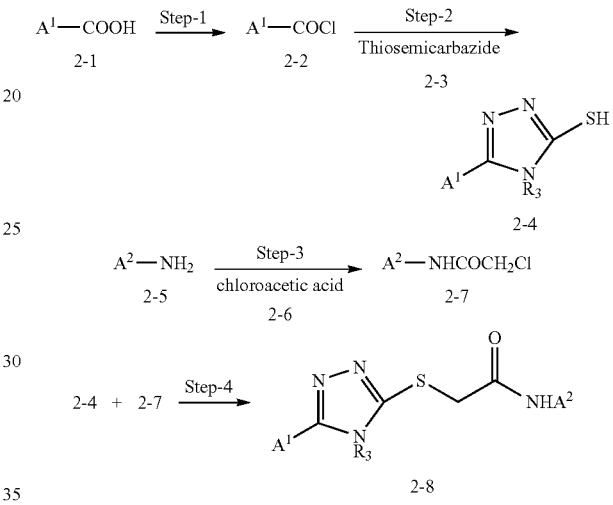

$A^1$=Phenyl or heterocycle substituted with ethyl, fluoro, methoxy and combinations thereof; $A^2$=phenyl, naphthyl, or heterocycle substituted with methyl, methoxy, hydroxyl, chloro, fluoro, trifluoromethyl, phenyl, acetyl, nitro, bromo, ethyl, ethoxy, phenoxy, n-propyl, benzyloxy, amino and combinations thereof or indan;

$R_3$=H or methyl;

General Procedure

Step-1:

Oxalyl chloride (20 mmole) followed by two drops DMF were added to a stirred solution of 1-1 (10 mmole) in dichloromethane (23 mL). Solution was stirred for 3 h at 25° C. Completion of the reaction was checked by TLC (CHCl$_3$: MeOH-9:1). Reaction mixture was then concentrated under vacuum to obtain compound 1-2.

Step-2

Compound 1-2 (8 mmole) was added drop wise to a stirred solution of thiosemicarbazide (8 mmole) in 2N NaOH (8 mL) at 0-5° C. Reaction mixture was then stirred at room temperature for 2 h and finally refluxed for 3 h. Completion of reaction was checked by TLC (CHCl$_3$:MeOH-9.5:0.5). After cooling to room temperature, 2 ml 10N NaOH was added to the reaction mixture and the resulting solution was filtered. The filtrate was acidified with conc. HCl and the precipitate obtained was collected by filtration to give 1-4 as white solid (yield: 55-97%).

Step-3

Chloroacetic acid 1-5 (23 mmole) in 10% NaOH (20 ml) was added to a solution of compound 1-4 in 10% NaOH (20 mL). Reaction mixture was refluxed for 4 h. After cooling, the reaction mixture was neutralized with glacial acetic acid and General Procedures Step-1:

Oxalyl chloride (20 mmole) followed by two drops DMF was added to a stirred solution of 2-1 (10 mmole) in dichloromethane (23 mL). The solution was stirred at 25° C. and after completion of the reaction (checked by TLC), the reaction mixture was then concentrated under vacuum to obtain compound 2-2.

Step-2:

Compound 2-2 (8 mmole) was added drop wise to a stirred solution of thiosemicarbazide or methylthiosemicarbazide (8 mmole) in 2N NaOH (8 mL) at 0-5° C. Reaction mixture was then stirred at room temperature for 2 h and then refluxed for 3 h. After completion of reaction (checked by TLC), the reaction mixture was cooled to room temperature and 2 ml 10N NaOH was added to the reaction mixture. The resulting solution was filtered, acidified with conc HCl, and the solid obtained was collected by filtration to give compound 2-4 (yield: 55-97%).

Step-3

Chloroacetyl chloride (54.38 mmole) was added drop wise to a stirred solution of desired amine, 2-5 (54.38 mmole) in acetonitrile (70 mL) in an ice bath. The reaction mixture was then heated to reflux until the gas (HCl) ceased to evolve. The reaction mixture was then cooled to ambient temperature and the solvent was removed under vacuum. The solid residue was washed with acetonitrile (3×8 mL), and the solid was collected by filtration to give compound 2-7 as a white powder (Yield—50-79%).

Step: 4

Compound 2-7 (15.55 mmole) was added to a solution of compound 2-4 (15.55 mmole) and NaOH (17.14 mmole) in methanol (32 mL). The reaction mixture was stirred overnight at room temperature. Solvent was removed and the crude was purified on a column of silica gel to give the desired target 2-8 (Yield—30-60%).

The compounds of Table 2 are exemplary compounds according to the invention prepared according to Scheme I or Scheme II, as set forth above and specified immediately after the compound name below.

TABLE 2

001

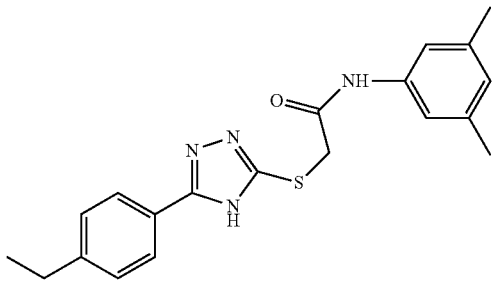 [SMILES: CCc1ccc(-c2nnc(SCC(=O)Nc3cc(C)cc(C)c3)[nH]2)cc1]

N-(3,5-Dimethyl-phenyl)-2-[5-(4-ethyl-phenyl)-4H-[1,2,4]triazol-3-ylsulfanyl]-acetamide. It was prepared using Scheme-1 as white solid. 1H NMR (300 MHz, DMSO-$d_6$) δ 1.28 (t, J = 7.5 Hz, 3H), 2.21 (s, 6H), 2.71 (q, J = 7.5 Hz, 2H), 3.89 (s, 2H), 6.72 (s, 1H), 7.14 (s, 2H), 7.26-7.32 (m, 2H), 7.90 (d, J = 8.1 Hz, 2H), 9.77 (s, 1H).

010

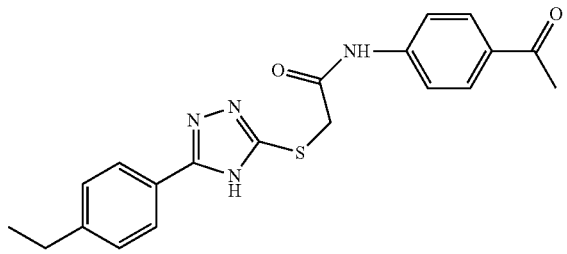 [SMILES: CCc1ccc(-c2nnc(SCC(=O)Nc3ccc(C(C)=O)cc3)[nH]2)cc1]

N-(4-Acetyl-phenyl)-2-[5-(4-ethyl-phenyl)-4H-[1,2,4]triazol-3-ylsulfanyl]-acetamide. It was prepared using Scheme-2 as white solid. 1H NMR (300 MHz, DMSO-$d_6$) δ 1.20 (t, J = 7.5 Hz, 3H), 2.49-2.61 (m, 3H), 2.65 (q, J = 7.5 Hz, 2H), 4.15 (s, 2H), 7.34 (d, J = 7.8 Hz, 2H), 7.71-7.74 (m, 2H), 7.84-7.86 (m, 2H), 7.92-7.95 (m, 2H), 10.64 (s, 1H), 14.35 (s, 1H).

011

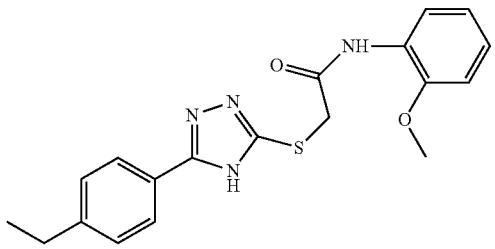 [SMILES: CCc1ccc(-c2nnc(SCC(=O)Nc3ccccc3OC)[nH]2)cc1]

2-[5-(4-Ethyl-phenyl)-4H-[1,2,4]triazol-3-ylsulfanyl]-N-(2-methoxy-phenyl)-acetamide. It was prepared using Scheme-1 as white solid. 1H NMR (300 MHz, DMSO-$d_6$) δ 1.20 (t, J = 7.5 Hz, 3H), 2.66 (q, J = 7.5 Hz, 2H), 3.71 (s, 3H), 4.09 (s, 2H), 6.89 (d, J = 6.6 Hz, 1H), 6.99-7.05 (m, 2H), 7.25-7.39 (m, 2H), 7.88-8.08 (m, 3H), 9.49 (s, 1H), 14.48 (s, 1H).

014

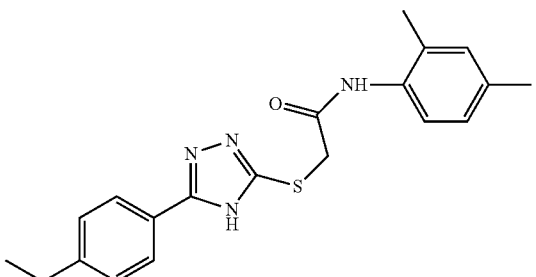

N-(2,4-Dimethyl-phenyl)-2-[5-(4-ethyl-phenyl)-4H-[1,2,4]triazol-3-ylsulfanyl]-acetamide. It was prepared using Scheme-2 as white solid. 1H NMR (300 MHz, DMSO-$d_6$) δ 1.21 (t, J = 7.5 Hz, 3H), 2.11 (s, 3H), 2.49 (s, 3H), 2.66 (q, J = 7.5 Hz, 2H), 4.10 (s, 2H), 6.94-6.99 (m, 2H), 7.26-7.37 (m, 3H), 7.88 (d, J = 8.1 Hz, 2H), 9.52 (s, 1H), 14.35 (s, 1H).

TABLE 2-continued

019

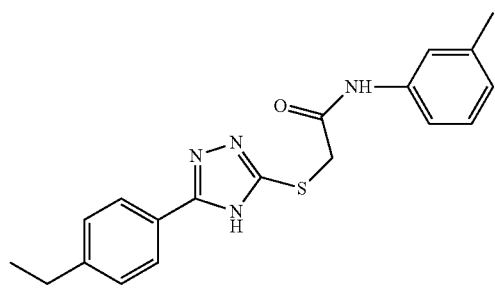 [SMILES: CCc1ccc(-c2nnc(SCC(=O)Nc3cccc(C)c3)[nH]2)cc1]

2-[5-(4-Ethyl-phenyl)-4H-[1,2,4]triazol-3-ylsulfanyl]-N-m-tolyl-acetamide.
It was prepared using Scheme-2 as white solid. 1H NMR (300 MHz, DMSO-$d_6$) δ 1.20
(t, J = 7.5 Hz, 3H), 2.26 (s, 3H), 2.65 (q, J = 7.5 Hz, 2H), 4.09 (s, 2H), 6.87 (d, J =
7.5 Hz, 1H), 7.18 (t, J = 7.5 Hz, 1H), 7.33-7.42 (m, 4H), 7.86 (d, J = 8.1 Hz, 2H),
10.22 (s, 1H), 14.32 (s, 1H).

021

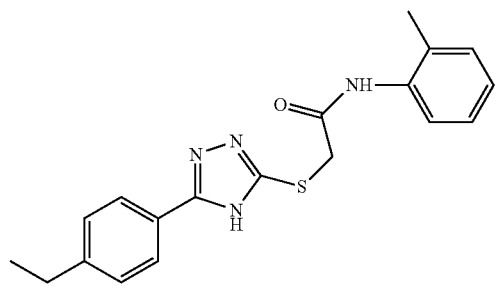 [SMILES: CCc1ccc(-c2nnc(SCC(=O)Nc3ccccc3C)[nH]2)cc1]

2-[5-(4-Ethyl-phenyl)-4H-[1,2,4]triazol-3-ylsulfanyl]-N-o-tolyl-acetamide.
It was prepared using Scheme-2 as white solid. 1H NMR (300 MHz, DMSO-$d_6$) δ 1.21
(t, J = 7.5 Hz, 3H), 2.16 (s, 3H), 2.66 (q, J = 7.5 Hz, 2H), 4.12 (s, 2H), 7.07-7.20 (m, 3H),
7.34-7.44 (m, 3H), 7.88 (d, J = 8.1 Hz, 2H), 9.60 (s, 1H).

022

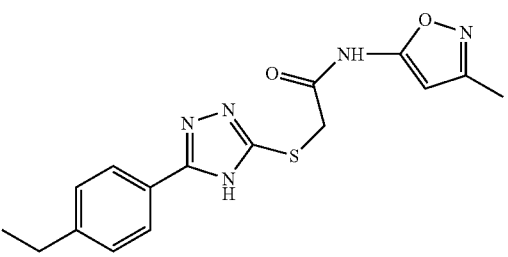 [SMILES: CCc1ccc(-c2nnc(SCC(=O)Nc3cc(C)no3)[nH]2)cc1]

2-[5-(4-Ethyl-phenyl)-4H-[1,2,4]triazol-3-ylsulfanyl]-N-(3-methyl-
isoxazol-5-yl)-acetamide. It was prepared using Scheme-2 as white solid. 1H NMR
(300 MHz, DMSO-$d_6$) δ 1.23 (m, 3H), 2.17 (q, J = 4.2 Hz, 3H), 2.62-2.70 (m, 2H), 4.13 (s,
2H), 6.11 (s, 1H), 7.34-7.45 (m, 2H), 7.84 (d, J = 8.4 Hz, 2H), 11.87 (s, 1H), 14.41 (s,
1H).

023

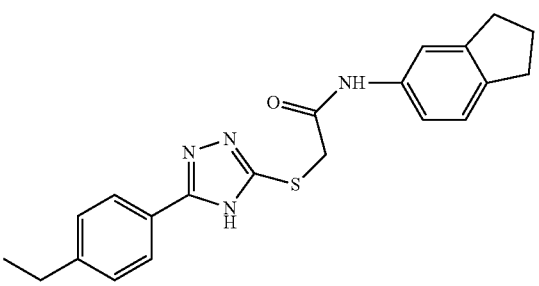 [SMILES: CCc1ccc(-c2nnc(SCC(=O)Nc3ccc4c(c3)CCC4)[nH]2)cc1]

2-[5-(4-Ethyl-phenyl)-4H-[1,2,4]triazol-3-ylsulfanyl]-N-indan-5-yl-
acetamide. It was prepared using Scheme-1 as white solid. 1H NMR (300 MHz,
DMSO-$d_6$) δ 1.20 (t, J = 7.5 Hz, 3H), 1.94-2.04 (m, 2H), 2.65 (q, J = 7.5 Hz, 2H), 2.80
(q, J = 7.2 Hz, 4H), 4.08 (s, 2H), 7.13 (d, J = 8.1 Hz, 1H), 7.26-7.34 (m, 3H), 7.50 (s,
1H), 7.87 (d, J = 8.1 Hz, 2H), 10.17 (s, 1H), 14.40 (s, 1H).

| | |
|---|---|
| 026 | 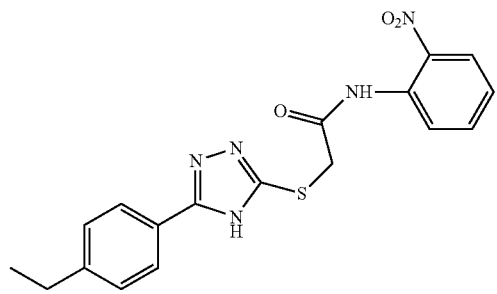 [SMILES: CCc1ccc(-c2nnc(SCC(=O)Nc3ccccc3[N+](=O)[O-])[nH]2)cc1]
2-[5-(4-Ethyl-phenyl)-4H-[1,2,4]triazol-3-ylsulfanyl]-N-(2-nitro-phenyl)-acetamide. It was prepared using Scheme-2 as Yellow solid. 1H NMR (300 MHz, DMSO-$d_6$) δ 1.20 (t, J = 7.5 Hz, 6H), 2.65 (q, J = 7.5 Hz, 2H), 4.14 (s, 2H), 7.33-7.39 (m, 3H), 7.73 (t, J = 7.5 Hz, 1H), 7.84-7.87 (m, 3H), 7.98-8.02 (m, 1H), 10.72 (s, 1H), 14.39 (br s, 1H). |
| 027 | 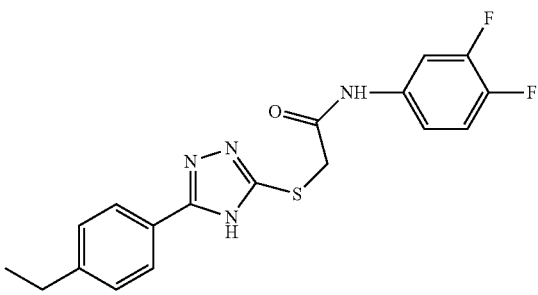 [SMILES: CCc1ccc(-c2nnc(SCC(=O)Nc3ccc(F)c(F)c3)[nH]2)cc1]
N-(3,4-Difluoro-phenyl)-2-[5-(4-ethyl-phenyl)-4H-[1,2,4]triazol-3-ylsulfanyl]-acetamide. It was prepared using Scheme-2 as white solid. 1H NMR (300 MHz, DMSO-$d_6$) δ 1.20 (t, J = 7.5 Hz, 3H), 2.66 (q, J = 7.5 Hz, 2H), 4.09 (s, 2H), 7.36-7.45 (m, 4H), 7.76-7.87 (m, 3H), 10.54 (s, 1H), 14.43 (s, 1H). |
| 030 | 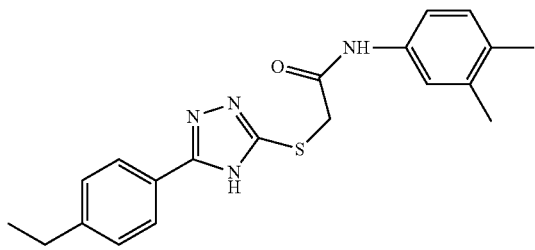 [SMILES: CCc1ccc(-c2nnc(SCC(=O)Nc3ccc(C)c(C)c3)[nH]2)cc1]
N-(3,4-Dimethyl-phenyl)-2-[5-(4-ethyl-phenyl)-4H-[1,2,4]triazol-3-ylsulfanyl]-acetamide. It was prepared using Scheme-2 as white solid. 1H NMR (300 MHz, DMSO-$d_6$) δ 1.20 (t, J = 7.5 Hz, 3H), 2.16 (s, 6H), 2.65 (q, J = 7.5 Hz, 2H), 4.08 (s, 2H), 7.05 (d, J = 8.4 Hz, 1H), 7.28-7.36 (m, 4H), 7.87 (d, J = 8.1 Hz, 2H), 10.14 (s, 1H), 14.34 (br s, 1H). |
| 033 | 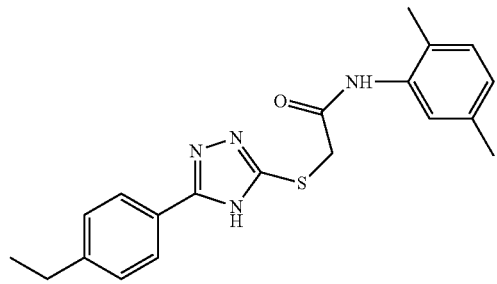 [SMILES: CCc1ccc(-c2nnc(SCC(=O)Nc3cc(C)ccc3C)[nH]2)cc1]
N-(2,5-Dimethyl-phenyl)-2-[5-(4-ethyl-phenyl)-4H-[1,2,4]triazol-3-ylsulfanyl]-acetamide. It was prepared using Scheme-2 as white solid. 1H NMR (300 MHz, DMSO-$d_6$) δ 1.21 (t, J = 7.5 Hz, 3H), 2.11 (s, 3H), 2.22 (s, 3H), 2.66 (q, J = 7.5 Hz, 2H), 4.08 (s, 2H), 6.88 (d, J = 7.5 Hz, 1H), 7.06 (d, J = 7.8 Hz, 1H), 7.21-7.39 (m, 3H), 7.87-7.92 (m, 2H), 9.51 (s, 1H), 14.44 (br s, 1H). |

TABLE 2-continued

041

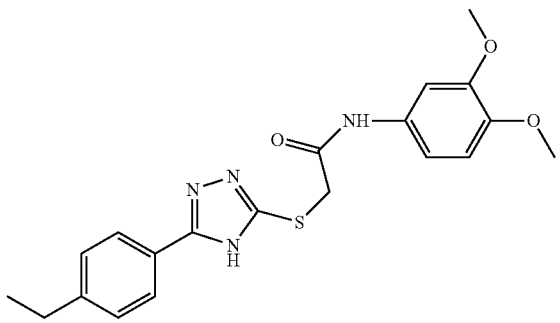 [SMILES: CCc1ccc(-c2nnc(SCC(=O)Nc3ccc(OC)c(OC)c3)[nH]2)cc1]

N-(3,4-Dimethoxy-phenyl)-2-[5-(4-ethyl-phenyl)-4H-[1,2,4]triazol-3-ylsulfanyl]-acetamide. It was prepared using Scheme-2 as white solid. 1H NMR (300 MHz, DMSO-$d_6$) δ 1.20 (t, J = 7.5 Hz, 3H), 2.64-2.67 (m, 2H), 3.93 (s, 6H), 4.06 (s, 2H), 6.89 (d, J = 8.7 Hz, 1H), 7.32 (d, J = 7.8 Hz, 1H), 7.28-7.35 (m, 3H), 7.86-7.89 (m, 2H), 10.16 (s, 1H), 14.41 (br s, 1H).

043

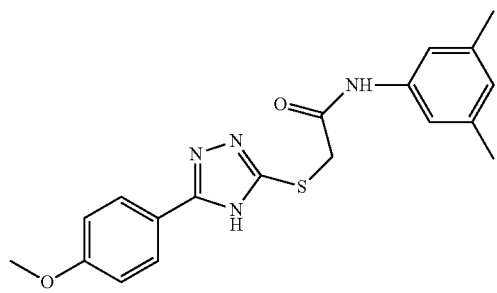

N-(3,5-Dimethyl-phenyl)-2-[5-(4-methoxy-phenyl)-4H-[1,2,4]triazol-3-ylsulfanyl]-acetamide. It was prepared using Scheme-2 as white solid. 1H NMR (300 MHz, CDCl$_3$) δ 2.22 (s, 6H), 3.82 (s, 3H), 4.04 (s, 2H), 6.70 (s, 1H), 7.08 (d, J = 8.4 Hz, 2H), 7.20 (s, 2H), 7.89 (d, J = 8.7 Hz, 2H), 10.12 (s, 1H), 14.29 (s, 1H).

044

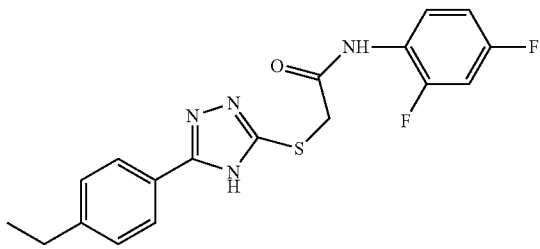 [SMILES: CCc1ccc(-c2nnc(SCC(=O)Nc3ccc(F)cc3F)[nH]2)cc1]

N-(2,4-Difluoro-phenyl)-2-[5-(4-ethyl-phenyl)-4H-[1,2,4]triazol-3-ylsulfanyl]-acetamide. It was prepared using Scheme-2 as white solid. 1H NMR (300 MHz, DMSO-$d_6$) δ 1.21 (t, J = 7.5 Hz, 3H), 2.66 (q, J = 7.5 Hz, 2H), 4.15 (s, 2H), 7.02-7.10 (m, 1H), 7.29-7.37 (m, 3H), 7.84-7.89 (m, 3H), 10.10 (s, 1H), 14.40 (br s, 1H).

045

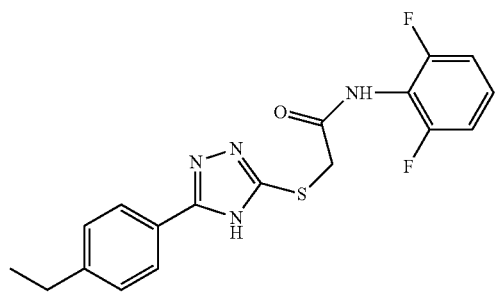 [SMILES: CCc1ccc(-c2nnc(SCC(=O)Nc3c(F)cccc3F)[nH]2)cc1]

N-(2,6-Difluoro-phenyl)-2-[5-(4-ethyl-phenyl)-4H-[1,2,4]triazol-3-ylsulfanyl]-acetamide. It was prepared using Scheme-2 as white solid. 1H NMR (300 MHz, CDCl$_3$) δ 1.25 (t, J = 7.5 Hz, 3H), 2.69 (q, J = 7.5 Hz, 2H), 3.95 (s, 2H), 6.91-6.97 (m, 2H), 7.15-7.20 (m, 1H), 7.27-7.32 (m, 2H), 7.91 (d, J = 7.8 Hz, 2H), 10.07 (s, 1H), 14.09 (br s, 1H).

TABLE 2-continued

049

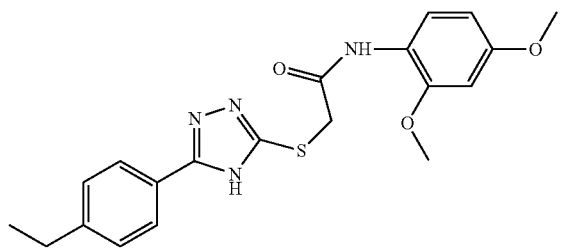 [SMILES: CCc1ccc(-c2nnc(SCC(=O)Nc3ccc(OC)cc3OC)[nH]2)cc1]

N-(2,4-Dimethoxy-phenyl)-2-[5-(4-ethyl-phenyl)-4H-[1,2,4]triazol-3-ylsulfanyl]-acetamide. It was prepared using Scheme-2 as white solid. 1H NMR (300 MHz, DMSO-$d_6$) δ 1.24 (t, J = 7.5 Hz, 3H), 2.67 (q, J = 7.5 Hz, 2H), 3.52 (s, 3H), 3.73 (s, 3H), 3.99 (s, 2H), 6.36-6.41 (m, 2H), 7.25 (d, J = 8.4 Hz, 2H), 7.91 (d, J = 8.1 Hz, 2H), 8.12 (d, J = 9.0 Hz, 1H), 9.22 (s, 1H).

053

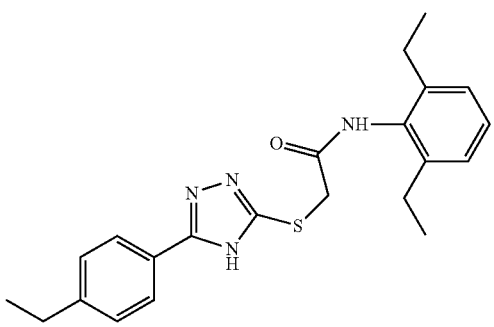 [SMILES: CCc1ccc(-c2nnc(SCC(=O)Nc3c(CC)cccc3CC)[nH]2)cc1]

N-(2,6-Diethyl-phenyl)-2-[5-(4-ethyl-phenyl)-4H-[1,2,4]triazol-3-ylsulfanyl]-acetamide. It was prepared using Scheme-2 as white solid. 1H NMR (300 MHz, DMSO-$d_6$) δ 1.08 (t, J = 7.5 Hz, 6H), 1.25 (t, J = 7.5 Hz, 3H), 2.53 (q, J = 7.5 Hz, 4H), 2.67 (q, J = 7.5 Hz, 2H), 3.98 (s, 2H), 7.06-7.08 (m, 2H), 7.15-7.30 (m, 3H), 7.86 (d, J = 8.4 Hz, 2H), 9.28 (s, 1H), 13.78 (s, 1H).

054

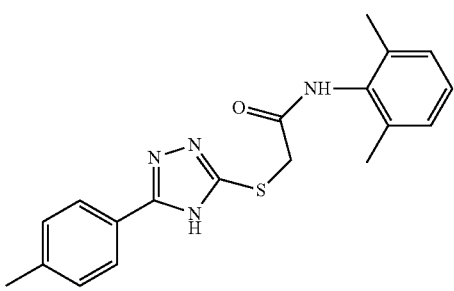 [SMILES: Cc1ccc(-c2nnc(SCC(=O)Nc3c(C)cccc3C)[nH]2)cc1]

N-(2,6-Dimethyl-phenyl)-2-(5-p-tolyl-4H-[1,2,4]triazol-3-ylsulfanyl)-acetamide. It was prepared using Scheme-2 as white solid. 1H NMR (300 MHz, DMSO-$d_6$) δ 2.16 (s, 6H), 2.38 (s, 3H), 3.97 (s, 2H), 7.00-7.06 (m, 3H), 7.23 (d, J = 8.1 Hz, 2H), 7.84 (d, J = 8.1 Hz, 2H), 9.30 (s, 1H), 13.85 (s, 1H).

055

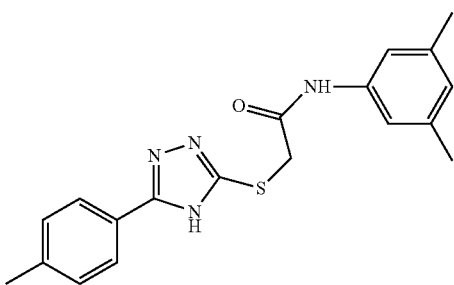

N-(3,5-Dimethyl-phenyl)-2-(5-p-tolyl-4H-[1,2,4]triazol-3-ylsulfanyl)-acetamide. It was prepared using Scheme-2 as white solid. 1H NMR (300 MHz, DMSO-$d_6$) δ 2.23 (s, 6H), 2.42 (d, J = 9.6 Hz, 3H), 3.87 (s, 2H), 6.70 (s, 1H), 7.17 (s, 2H), 7.27 (d, J = 8.1 Hz, 2H), 7.93 (d, J = 8.1 Hz, 2H), 10.20 (s, 1H), 14.05 (brs, 1H).

TABLE 2-continued

061

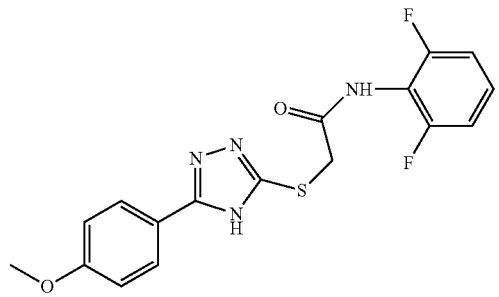 [SMILES: COc1ccc(-c2nnc(SCC(=O)Nc3c(F)cccc3F)[nH]2)cc1]

N-(2,6-Difluoro-phenyl)-2-[5-(4-methoxy-phenyl)-4H-[1,2,4]triazol-3-ylsulfanyl]-acetamide. It was prepared using Scheme-2 as white solid. 1H NMR (300 MHz, DMSO-$d_6$) δ 3.85 (s, 3H), 3.95 (s, 2H), 6.93-6.97 (m, 4H), 7.12-7.22 (m, 1H), 7.94 (d, J = 9.0 Hz, 2H), 10.06 (s, 1H), 13.90 (s, 1H).

062

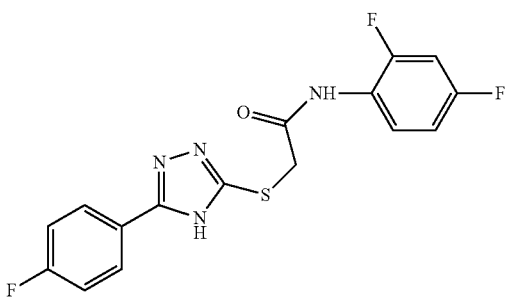 [SMILES: O=C(CSc1nnc(-c2ccc(F)cc2)[nH]1)Nc1ccc(F)cc1F]

N-(2,4-Difluoro-phenyl)-2-[5-(4-fluoro-phenyl)-4H-[1,2,4]triazol-3-ylsulfanyl]-acetamide. It was prepared using Scheme-2 as white solid. 1H NMR (300 MHz, DMSO-$d_6$) δ 3.96 (s, 2H), 6.78-6.88 (m, 2H), 7.15 (t, J = 7.8 Hz, 2H), 8.05 (br s, 2H), 8.23-8.25 (m, 1H), 9.98 (s, 1H), 14.30 (s, 1H).

063

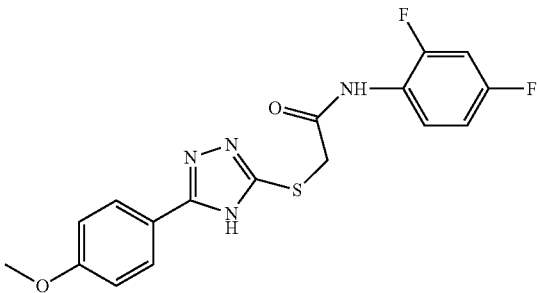 [SMILES: COc1ccc(-c2nnc(SCC(=O)Nc3ccc(F)cc3F)[nH]2)cc1]

N-(2,4-Difluoro-phenyl)-2-[5-(4-methoxy-phenyl)-4H-[1,2,4]triazol-3-ylsulfanyl]-acetamide. It was prepared using Scheme-2 as white solid. 1H NMR (300 MHz, DMSO-$d_6$) δ 3.86 (d, J = 5.1 Hz, 3H), 3.93 (s, 2H), 6.82-6.89 (m, 2H), 6.98 (d, J = 8.7 Hz, 2H), 7.97 (d, J = 8.1 Hz, 2H), 8.21-8.26 (m, 1H), 10.11 (s, 1H), 14.09 (br s, 1H).

066

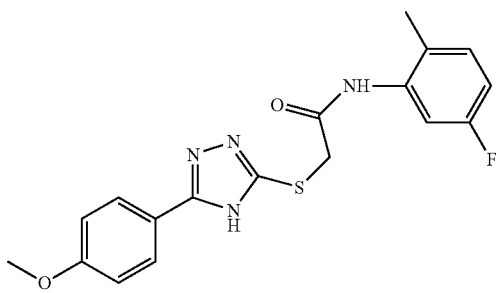 [SMILES: COc1ccc(-c2nnc(SCC(=O)Nc3cc(F)ccc3C)[nH]2)cc1]

N-(5-Fluoro-2-methyl-phenyl)-2-[5-(4-methoxy-phenyl)-4H-[1,2,4]triazol-3-ylsulfanyl]-acetamide. It was prepared using Scheme-2 as white solid. 1H NMR (300 MHz, CDCl$_3$) δ 2.06 (s, 3H), 3.85 (s, 3H), 3.96 (s, 2H), 6.70-6.74 (m, 1H), 6.94-7.04 (m, 3H), 7.77-7.81 (m, 1H), 7.89 (s, 1H), 7.93 (s, 1H), 9.44 (s, 1H), 13.99 (br s, 1H).

TABLE 2-continued

068

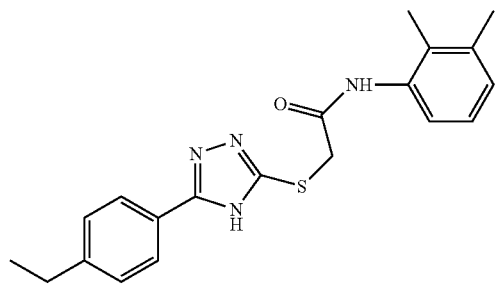

N-(2,3-Dimethyl-phenyl)-2-[5-(4-ethyl-phenyl)-4H-[1,2,4]triazol-3-ylsulfanyl]-acetamide. It was prepared using Scheme-2 as white solid. 1H NMR (300 MHz, DMSO-$d_6$) δ 1.21 (t, J = 7.5 Hz, 3H), 2.04 (s, 3H), 2.22 (s, 3H), 2.66 (q, J = 7.5 Hz, 2H), 4.12 (s, 2H), 6.98-7.06 (m, 2H), 7.14-7.17 (m, 1H), 7.34-7.37 (m, 2H), 7.88 (s, 1H), 7.90 (s, 1H), 9.67 (s, 1H), 14.37 (br s, 1H).

070

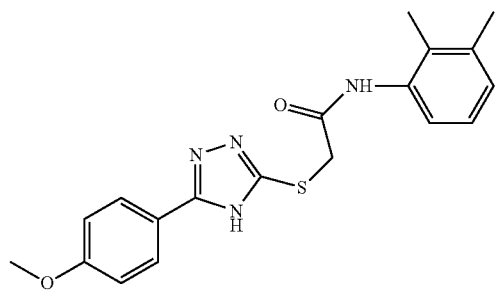

N-(2,3-Dimethyl-phenyl)-2-[5-(4-methoxy-phenyl)-4H-[1,2,4]triazol-3-ylsulfanyl]-acetamide. It was prepared using Scheme-2 as white solid. 1H NMR (300 MHz, CDCl$_3$) δ 2.02 (s, 3H), 2.23 (s, 3H), 3.84 (s, 3H), 3.95 (s, 2H), 6.93-6.98 (m, 3H), 7.06 (t, J = 7.8 Hz, 1H), 7.45-7.48 (m, 1H), 7.90 (s, 1H), 7.93 (s, 1H), 9.39 (s, 1H), 14.05 (br s, 1H).

078

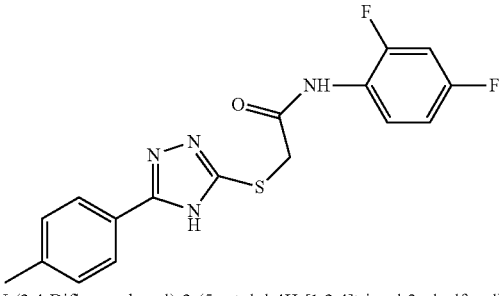

N-(2,4-Difluoro-phenyl)-2-(5-p-tolyl-4H-[1,2,4]triazol-3-ylsulfanyl)-acetamide. It was prepared using Scheme-2 as white solid. 1H NMR (300 MHz, DMSO-$d_6$) δ 2.36 (s, 3H), 4.15 (s, 2H), 7.07 (m, 1H), 7.29-7.37 (m, 3H), 7.83-7.88 (m, 3H), 10.11 (s, 1H), 14.28 (br. s, 1H).

080

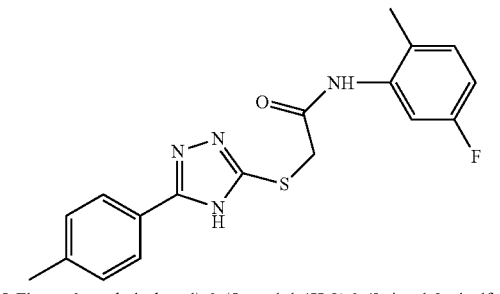

N-(5-Fluoro-2-methyl-phenyl)-2-(5-p-tolyl-4H-[1,2,4]triazol-3-ylsulfanyl)-acetamide. It was prepared using Scheme-2 as white solid. 1H NMR (300 MHz, DMSO-$d_6$) δ 2.15 (s, 3H), 2.36 (s, 3H), 4.14 (s, 2H), 6.90-6.94 (m, 1H), 7.19-7.24 (m, 1H), 731 (s, 1H), 7.34 (s, 1H), 7.44 (dd, J = 11.1 Hz, 2.7 Hz, 1H), 7.84-7.87 (m, 2H), 9.63 (s, 1H), 14.35 (br s, 1H).

082

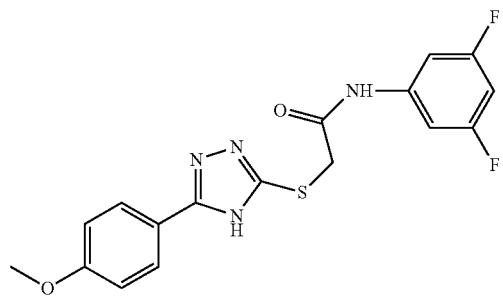 [SMILES: COc1ccc(-c2nnc(SCC(=O)Nc3cc(F)cc(F)c3)[nH]2)cc1]

N-(3,5-Difluoro-phenyl)-2-[5-(4-methoxy-phenyl)-4H-[1,2,4]triazol-3-ylsulfanyl]-acetamide. It was prepared using Scheme-2 as white solid. 1H NMR (300 MHz, DMSO-$d_6$) δ 3.81 (s, 3H), 4.11 (s, 2H), 6.93 (tt, J = 9.3 Hz, 2.4 Hz, 1H), 7.06 (m, 2H), 7.29-7.33 (m, 2H), 785-7.89 (m, 2H), 10.70 (s, 1H), 14.21 (br s, 1H).

085

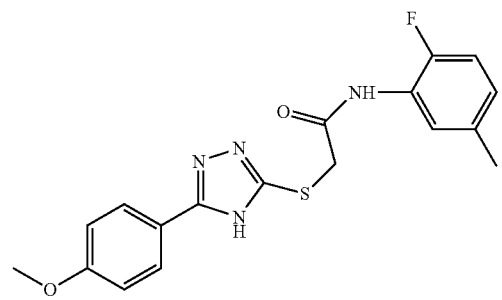

N-(2-Fluoro-5-methyl-phenyl)-2-[5-(4-methoxy-phenyl)-4H-[1,2,4]triazol-3-ylsulfanyl]-acetamide. It was prepared using Scheme-2 as white solid. 1H NMR (300 MHz, DMSO-$d_6$) δ 2.25 (s, 3H), 3.82 (s, 3H), 4.13 (s, 2H), 6.92-6.95 (m, 1H), 7.06-7.16 (m, 1H), 7.75 (d, J = 7.2 Hz, 1H), 7.89 (s, 1H), 7.91 (s, 1H), 10.01 (s, 1H), 14.32 (br s, 1H).

089

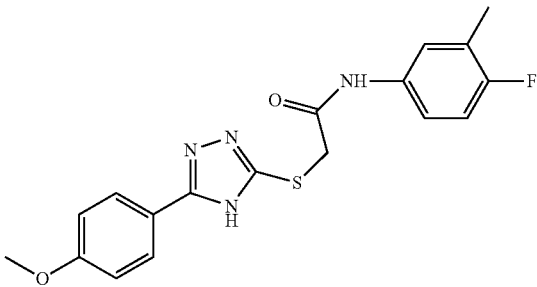 [SMILES: COc1ccc(-c2nnc(SCC(=O)Nc3ccc(F)c(C)c3)[nH]2)cc1]

N-(4-Fluoro-3-methyl-phenyl)-2-[5-(4-methoxy-phenyl)-4H-[1,2,4]triazol-3-ylsulfanyl]-acetamide. It was prepared using Scheme-2 as white solid. 1H NMR (300 MHz, DMSO-$d_6$) δ 2.18 (s, 3H), 3.79 (s, 3H), 4.05 (s, 2H), 7.03-7.09 (m, 3H), 7.34-7.39 (m, 1H), 7.48 (dd, J = 6.9 Hz, 2.1 Hz, 1H), 7.85 (s, 1H), 7.88 (s, 1H), 10.25 (s, 1H), 14.21 (br s, 1H).

092

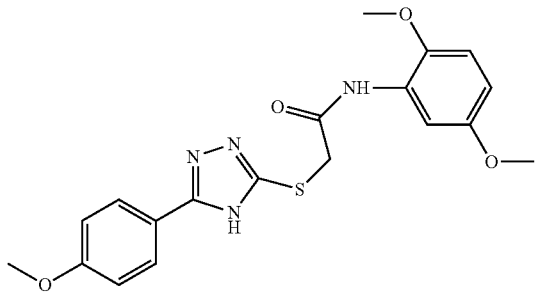

N-(2,5-Dimethoxy-phenyl)-2-[5-(4-methoxy-phenyl)-4H-[1,2,4]triazol-3-ylsulfanyl]-acetamide. It was prepared using Scheme-2 as white solid. 1H NMR (300 MHz, DMSO-$d_6$) δ 3.67 (s, 6H), 3.82 (s, 3H), 4.09-4.21 (m, 2H), 6.61 (d, J = 8.1 Hz, 1H), 6.90-7.11 (m, 3H), 7.75-7.93 (m, 3H), 9.50 (s, 1H), 14.38 (br s, 1H).

TABLE 2-continued

096

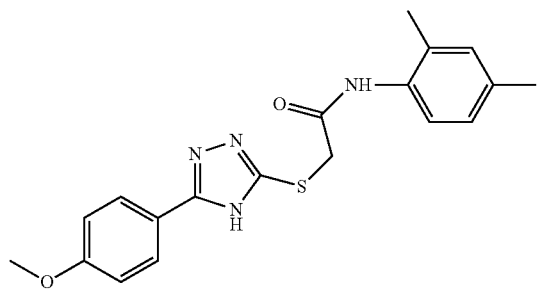

N-(2,4-Dimethyl-phenyl)-2-[5-(4-methoxy-phenyl)-4H-[1,2,4]triazol-3-ylsulfanyl]-acetamide. It was prepared using Scheme-2 as white solid. 1H NMR (300 MHz, DMSO-$d_6$) δ 2.11 (s, 3H), 2.23 (s, 3H), 3.82 (s, 2H), 4.09 (s, 2H), 6.94-7.00 (m, 2H), 7-06-7.09 (m, 2H), 7.28 (d, J = 8.1 Hz, 1H), 7.90-7.93 (m, 2H), 9.52 (s, 1H), 14.27 (br s, 1H).

098

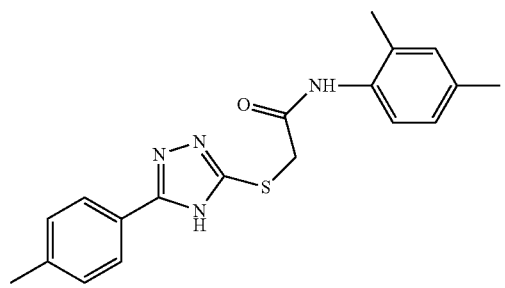

N-(2,4-Dimethyl-phenyl)-2-(5-p-tolyl-4H-[1,2,4]triazol-3-ylsulfanyl)-acetamide. It was prepared using Scheme-2 as white solid. 1H NMR (300 MHz, DMSO-$d_6$) δ 2.06 (s, 3H), 2.27 (s, 3H), 2.38 (s, 3H), 3.95 (s, 2H), 6.92-6.98 (m, 2H), 7.22-7.25 (m, 2H), 7.61 (d, J = 8.1 Hz, 1H), 7.84-7.87 (m, 2H), 9.30 (s, 1H), 13.94 (br s, 1H).

099

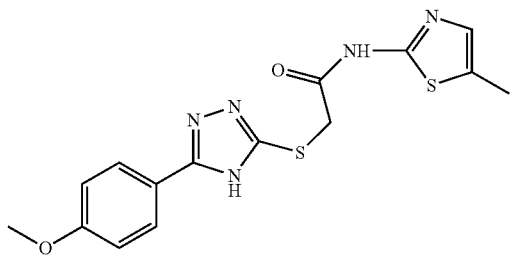

2-[5-(4-Methoxy-phenyl)-4H-[1,2,4]triazol-3-ylsulfanyl]-N-(5-methyl-thiazol-2-yl)-acetamide. It was prepared using Scheme-2 as white solid. 1H NMR (300 MHz, DMSO-$d_6$) δ 2.33 (s, 3H), 3.81 (s, 3H), 4.15 (s, 2H), 7.04-7.15 (m, 3H), 7.85-7.88 (m, 2H), 12.21 (br s, 1H), 14.28 (br s, 1H).

104

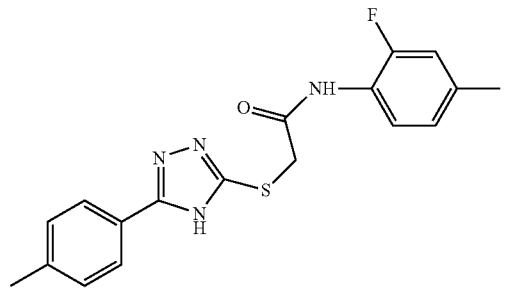

N-(2-Fluoro-4-methyl-phenyl)-2-(5-p-tolyl-4H-[1,2,4]triazol-3-ylsulfanyl)-acetamide. It was prepared using Scheme-2 as white solid. 1H NMR (300 MHz, DMSO-$d_6$) δ 2.27 (s, 3H), 2.36 (s, 3H), 4.15 (s, 2H), 6.96 (d, J = 8.7 Hz, 1H), 7.08 dd, J = 12 Hz, 1.2 Hz, 1H), 7.31-7.33 (m, 2H), 7.76 (t, J = 8.4 Hz, 1H), 7.84-7.87 (m, 2H), 10.00 (s, 1H), 14.38 (br s, 1H).

| | |
|---|---|
| 105 | 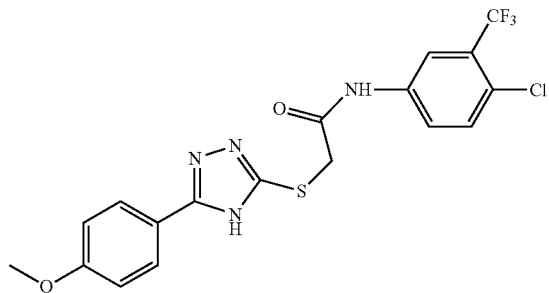 [SMILES: COc1ccc(-c2nnc(SCC(=O)Nc3ccc(Cl)c(C(F)(F)F)c3)[nH]2)cc1]<br>N-(4-Chloro-3-trifluoromethyl-phenyl)-2-[5-(4-methoxy-phenyl)-4H-[1,2,4]triazol-3-ylsulfanyl]-acetamide. It was prepared using Scheme-2 as white solid. 1H NMR (300 MHz, DMSO-d$_6$) δ 3.82 (s, 3H), 4.12 (s, 2H), 7.04-7.07 (m, 2H) 7.68 (d, J = 8.7 Hz, 1H), 7.83-7.90 (m, 3H), 8.19 (s, 1H), 10.76 (s, 1H), 14.24 (br s, 1H). |
| 110 | 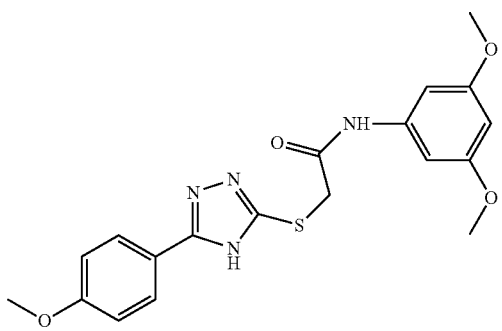 [SMILES: COc1ccc(-c2nnc(SCC(=O)Nc3cc(OC)cc(OC)c3)[nH]2)cc1]<br>N-(3,5-Dimethoxy-phenyl)-2-[5-(4-methoxy-phenyl)-4H-[1,2,4]triazol-3-ylsulfanyl]-acetamide. It was prepared using Scheme-2 as white solid. 1H NMR (300 MHz, DMSO-d$_6$) δ 3.37 (s, 6H), 3.70 (s, 3H), 4.06 (s, 2H), 6.23 (s, 1H), 6.84 (s, 2H), 7.07-7.09 (m, 2H), 7.88 (s, 1H), 7.91 (s, 1H), 10.25 (s, 1H), 14.31 (s, 1H). |
| 111 | 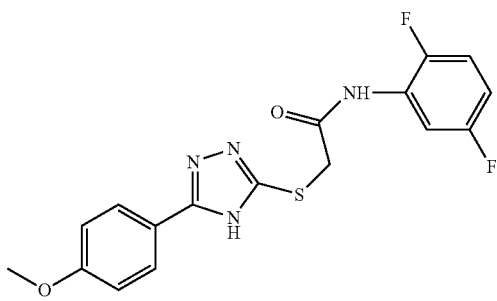 [SMILES: COc1ccc(-c2nnc(SCC(=O)Nc3cc(F)ccc3F)[nH]2)cc1]<br>N-(2,5-Difluoro-phenyl)-2-[5-(4-methoxy-phenyl)-4H-[1,2,4]triazol-3-ylsulfanyl]-acetamide. It was prepared using Scheme-2 as white solid. 1H NMR (300 MHz, DMSO-d$_6$) δ 3.82 (s, 3H), 4.17 (s, 2H), 7.05-7.08 (m, 2H), 7.17 (t, J = 6.6 Hz, 2H), 7.72 (t, J = 7.2 Hz, 1H), 7.88 (s, 1H), 7.91 (s, 1H), 10.29 (s, 1H), 14.31 (br s, 1H). |
| 121 | 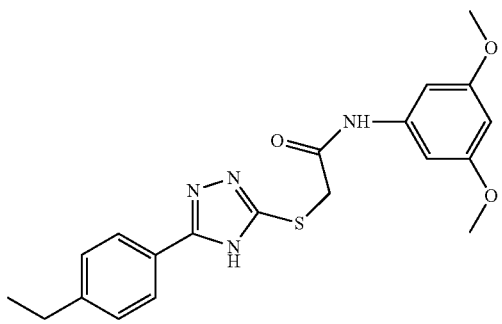 [SMILES: CCc1ccc(-c2nnc(SCC(=O)Nc3cc(OC)cc(OC)c3)[nH]2)cc1]<br>N-(3,5-Dimethoxy-phenyl)-2-[5-(4-ethyl-phenyl)-4H-[1,2,4]triazol-3-ylsulfanyl]-acetamide. It was prepared using Scheme-2 as white solid. 1H NMR (300 MHz, DMSO-d$_6$) δ 1.20 (t, J = 7.5 Hz, 3H), 2.65 (q, J = 7.5 Hz, 2H), 3.69 (s, 6H), 4.07 (s, 2H), 6.22-6.23 (m, 1H), 6.83 (s, 2H), 7.35-7.38 (m, 2H), 7.87 (d, J = 8.1 Hz, 2H), 10.26 (s, 1H), 14.42 (s, 1H). |

TABLE 2-continued

123

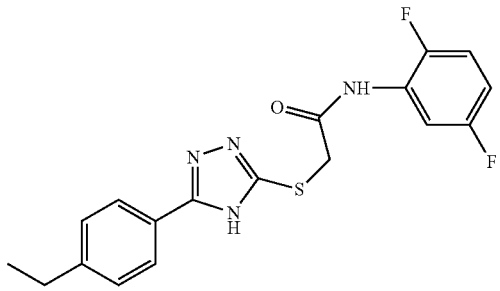 [SMILES: CCc1ccc(-c2nnc(SCC(=O)Nc3cc(F)ccc3F)[nH]2)cc1]

N-(2,5-Difluoro-phenyl)-2-[5-(4-ethyl-phenyl)-4H-[1,2,4]triazol-3-ylsulfanyl]-acetamide. It was prepared using Scheme-2 as white solid. 1H NMR (300 MHz, DMSO-$d_6$) δ 1.20 (t, J = 7.5 Hz, 3H), 2.66 (q, J = 7.5 Hz, 2H), 4.18 (s, 2H), 7.15-7.21 (m, 2H), 7.34-7.36 (m, 2H), 7.00-7.75 (m, 1H), 7.87 (d, J = 8.4 Hz, 2H), 10.30 (s, 1H), 14.42 (br s, 1H).

140

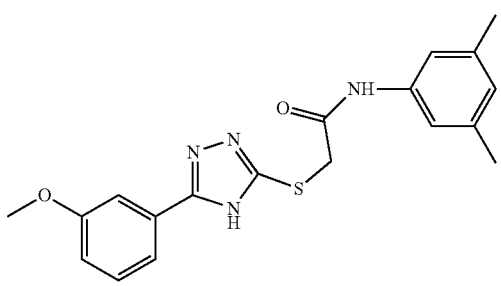

N-(3,5-Dimethyl-phenyl)-2-[5-(3-methoxy-phenyl)-4H-[1,2,4]triazol-3-ylsulfanyl]-acetamide. It was prepared using Scheme-2 as white solid. 1H NMR (300 MHz, DMSO-$d_6$) δ 2.21 (s, 6H), 3.79 (s, 3H), 4.08 (s, 2H), 6.69 (s, 1H), 7.03-7.06 (m, 1H), 7.21 (s, 2H), 7.41-7.55 (m, 3H), 10.15 (s, 1H), 14.43 (br s, 1H).

167

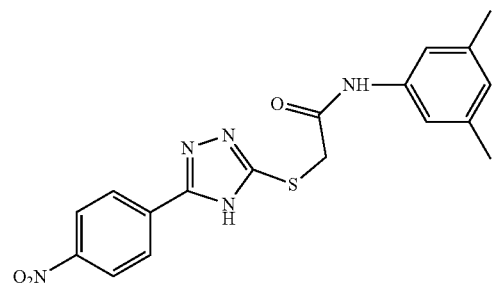

N-(3,5-Dimethyl-phenyl)-2-[5-(4-nitro-phenyl)-4H-[1,2,4]triazol-3-ylsulfanyl]-acetamide. It was prepared using Scheme-2 as Light yellow solid; 1H NMR (300 MHz, DMSO-$d_6$) δ 2.22 (s, 6H), 4.20 (s, 2H), 6.70 (s, 1H), 7.20 (s, 2H), 8.20-8.22 (m, 2H), 8.31-8.39 (m, 2H), 10.19 (s, 1H), 14.49 (br s, 1H).

The compounds of Table 3 are novel exemplary compounds according to the invention prepared according to Scheme I or Scheme II, as set forth above and specified immediately after the compound name below.

TABLE 3

002

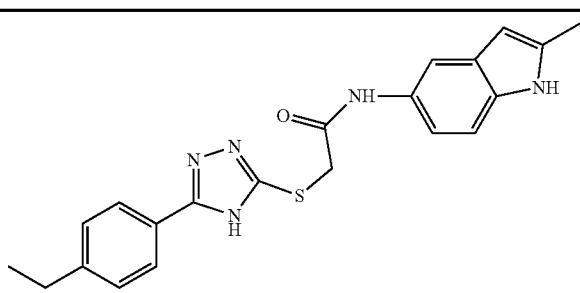

2-[5-(4-Ethyl-phenyl)-4H-[1,2,4]triazol-3-ylsulfanyl]-N-(2-methyl-1H-indol-5-yl)-acetamide. It was prepared using Scheme-1 as white solid. 1H NMR (300 MHz, DMSO-$d_6$) δ 1.27 (t, J = 7.5 Hz, 3H), 2.41 (s, 3H), 2.72 (q, J = 7.5 Hz, 2H), 4.14 (s, 2H), 6.12 (s, 1H), 7.18-7.22 (m, 2H), 7.42 (brs, 2H), 7.76 (s, 1H), 7.94 (d, J = 7.5 Hz, 2H), 10.08 (s, 1H), 10.88 (s, 1H), 14.47 (s, 1H).

TABLE 3-continued

003

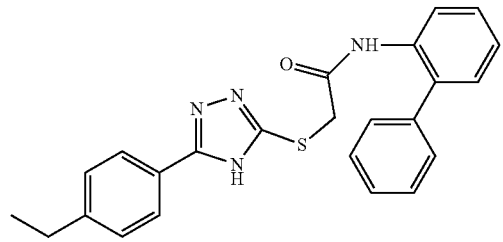 [SMILES: CCc1ccc(-c2nnc(SCC(=O)Nc3ccccc3-c3ccccc3)[nH]2)cc1]

N-Biphenyl-2-yl-2-[5-(4-ethyl-phenyl)-4H-[1,2,4]triazol-3-ylsulfanyl]-
acetamide. It was prepared using Scheme-1 as white solid. 1H NMR (300 MHz,
DMSO-$d_6$) δ 1.30 (t, J = 7.5 Hz, 3H), 2.66 (q, J = 7.5 Hz, 2H), 4.03 (s, 2H), 7.27-7.39
(m, 8H), 7.68-7.70 (m, 2H), 7.82-7.84 (m, 3H), 9.49 (s, 1H), 14.36 (s, 1H).

004

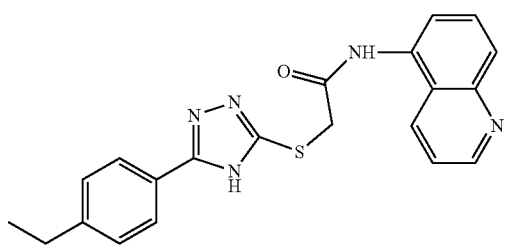 [SMILES: CCc1ccc(-c2nnc(SCC(=O)Nc3cccc4ncccc34)[nH]2)cc1]

2-[5-(4-Ethyl-phenyl)-4H-[1,2,4]triazol-3-ylsulfanyl]-N-quinolin-5-yl-
acetamide. It was prepared using Scheme-2 as white solid, white solid. 1H NMR
(300 MHz, DMSO-$d_6$) δ 1.26 (t, J = 7.5 Hz, 3H), 2.69 (q, J = 7.5 Hz, 2H), 4.25 (s, 2H),
7.38-7.46 (m, 3H), 7.73-7.75 (m, 2H), 7.86-8.00 (m, 3H), 8.49 (d, J = 8.1 Hz, 1H),
8.88-8.90 (m, 1H), 10.38 (s, 1H), 14.45 (s, 1H).

005

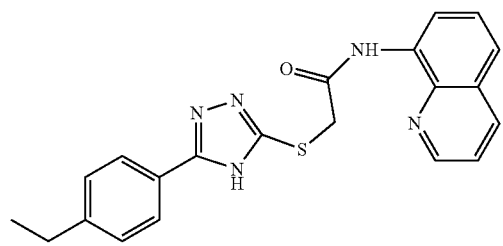 [SMILES: CCc1ccc(-c2nnc(SCC(=O)Nc3cccc4cccnc34)[nH]2)cc1]

2-[5-(4-Ethyl-phenyl)-4H-[1,2,4]triazol-3-ylsulfanyl]-N-quinolin-8-yl-
acetamide. It was prepared using Scheme-2 as white solid. 1H NMR (300 MHz,
DMSO-$d_6$) δ 1.26 (t, J = 7.5 Hz, 3H), 2.71 (q, J = 7.5 Hz, 2H), 4.31 (s, 2H), 7.40 (s, 2H),
7.63-7.72 (m, 3H), 7.93-7.96 (m, 2H), 8.43-8.46 (m, 1H), 8.69-8.78 (m, 2H), 10.83 (s,
1H), 14.50 (s, 1H).

007

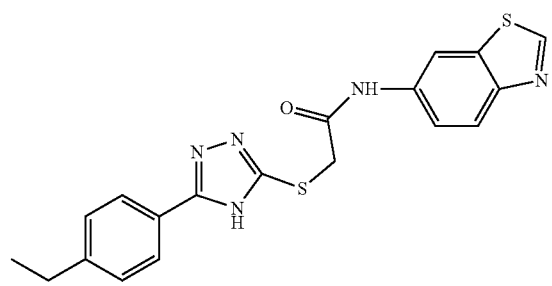 [SMILES: CCc1ccc(-c2nnc(SCC(=O)Nc3ccc4ncsc4c3)[nH]2)cc1]

N-Benzothiazol-6-yl-2-[5-(4-ethyl-phenyl)-4H-[1,2,4]triazol-3-ylsulfanyl]-
acetamide. It was prepared using Scheme-1 as white solid. white solid. 1H NMR
(300 MHz, DMSO-$d_6$) δ 1.20 (t, J = 7.5 Hz, 3H), 2.63 (q, J = 7.5 Hz, 2H), 4.14 (s, 2H), 7.37-
7.44 (m, 2H), 7.58-7.62 (m, 2H), 7.84-8.04 (m, 2H), 8.54 (s, 1H), 9.28 (d, J = 7.2 Hz,
1H), 10.60 (s, 1H), 14.50 (s, 1H).

008

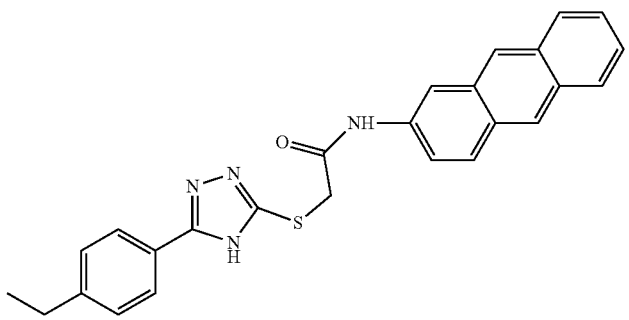 [SMILES: CCc1ccc(-c2nnc(SCC(=O)Nc3ccc4cc5ccccc5cc4c3)[nH]2)cc1]

N-Anthracen-2-yl-2-[5-(4-ethyl-phenyl)-4H-[1,2,4]triazol-3-ylsulfanyl]-
acetamide. It was prepared using Scheme-2 as Brown solid. 1H NMR (300 MHz,
DMSO-$d_6$) δ 1.20 (t, J = 7.5 Hz, 3H), 2.64 (q, J = 7.5 Hz, 2H), 4.30 (s, 2H), 7.42-7.50 (m,
5H), 7.96-8.09 (m, 5H), 8.48-8.52 (m, 3H), 10.58 (s, 1H), 14.21 (s, 1H).

009

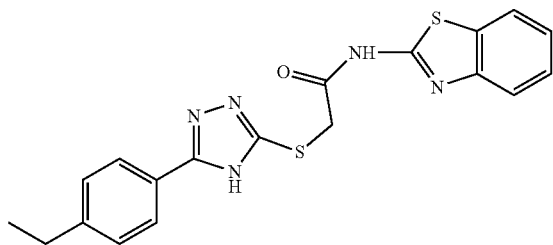 [SMILES: CCc1ccc(-c2nnc(SCC(=O)Nc3nc4ccccc4s3)[nH]2)cc1]

N-Benzothiazol-2-yl-2-[5-(4-ethyl-phenyl)-4H-[1,2,4]triazol-3-ylsulfanyl]-
acetamide. It was prepared using Scheme-2 as white solid. 1H NMR (300 MHz, DMSO-
$d_6$) δ 1.18 (t, J = 7.5 Hz, 3H), 2.63 (q, J = 7.5 Hz, 2H), 4.25 (s, 2H), 7.29-7.34 (m, 3H),
7.42-7.48 (m, 1H), 7.76-7.85 (m, 3H), 7.98 (d, J = 7.8 Hz, 1H), 12.68 (s, 1H), 14.44 (s,
1H).

012

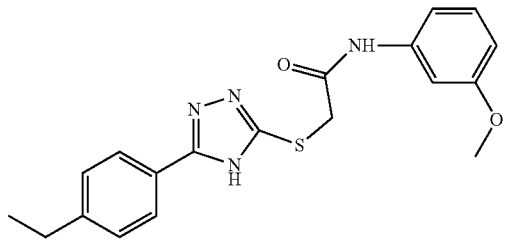 [SMILES: CCc1ccc(-c2nnc(SCC(=O)Nc3cccc(OC)c3)[nH]2)cc1]

2-[5-(4-Ethyl-phenyl)-4H-[1,2,4]triazol-3-ylsulfanyl]-N-(3-methoxy-
phenyl)-acetamide. It was prepared using Scheme-1 as white solid. 1H NMR (300 MHz,
DMSO-$d_6$) δ 1.20 (t, J = 7.5 Hz, 3H), 2.65 (q, J = 7.5 Hz, 2H), 3.70 (s, 3H), 4.09 (s, 2H),
6.63 (d, J = 8.1 Hz, 1H), 7.10-7.42 (m, 5H), 7.85-7.97 (m, 2H), 10.29 (s, 1H), 14.39 (s,
1H).

013

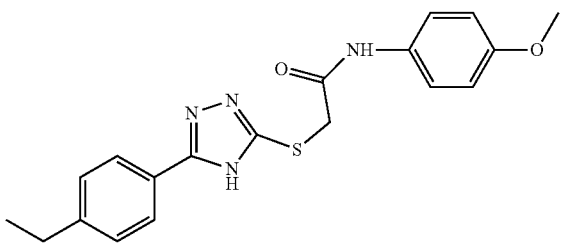 [SMILES: CCc1ccc(-c2nnc(SCC(=O)Nc3ccc(OC)cc3)[nH]2)cc1]

2-[5-(4-Ethyl-phenyl)-4H-[1,2,4]triazol-3-ylsulfanyl]-N-(4-methoxy-
phenyl)-acetamide. It was prepared using Scheme-2 as white solid. 1H NMR
(300 MHz, DMSO-$d_6$) δ 1.20 (t, J = 7.5 Hz, 3H), 2.66 (q, J = 7.5 Hz, 2H), 3.33 (s, 3H), 4.15
(s, 2H), 6.88 (d, J = 9.0 Hz, 2H), 7.30-7.38 (m, 2H), 7.45-7.51 (m, 2H), 7.86 (d, J =
7.8 Hz, 2H), 10.14 (s, 1H), 14.40 (s, 1H).

| | |
|---|---|
| 015 | 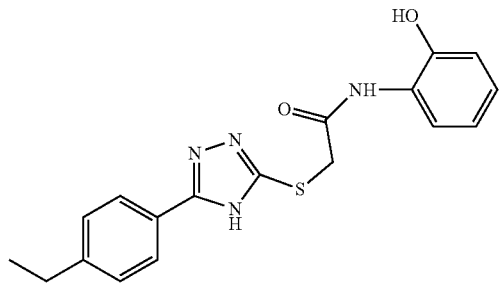 [SMILES: CCc1ccc(-c2nnc(SCC(=O)Nc3ccccc3O)[nH]2)cc1]<br>2-[5-(4-Ethyl-phenyl)-4H-[1,2,4]triazol-3-ylsulfanyl]-N-(2-hydroxy-phenyl)-acetamide. It was prepared using Scheme-2 as white solid. 1H NMR (300 MHz, DMSO-d$_6$) δ 1.21 (t, J = 7.5 Hz, 3H), 2.66 (q, J = 7.5 Hz, 2H), 4.04 (s, 2H), 6.78 (m, 1H), 6-84-6.94 (m, 2H), 7.35-7.37 (m, 2H), 7.89 (d, J = 8.1 Hz, 3H), 9.49 (s, 1H), 9.84 (s, 1H), 14.46 (s, 1H). |
| 016 | 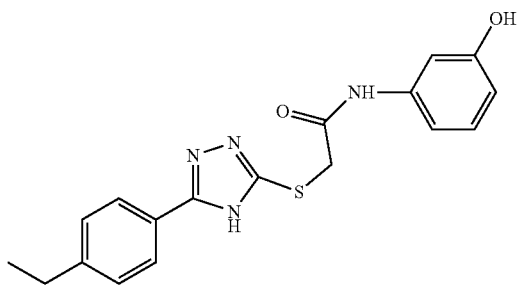 [SMILES: CCc1ccc(-c2nnc(SCC(=O)Nc3cccc(O)c3)[nH]2)cc1]<br>2-[5-(4-Ethyl-phenyl)-4H-[1,2,4]triazol-3-ylsulfanyl]-N-(3-hydroxy-phenyl)-acetamide. 1H NMR (300 MHz, DMSO-d$_6$) δ 1.20 (t, J = 7.5 Hz, 3H), 2.65 (q, J = 7.5 Hz, 2H), 4.08 (s, 2H), 6.46-6.47 (m, 1H), 6-93-6.95 (m, 1H), 7.07 (t, J = 8.1 Hz, 1H), 7.17 (s, 1H), 7.35 (d, J = 7.5 Hz, 2H), 7.86 (d, J = 8.1 Hz, 2H), 10.17 (s, 1H), 14.38 (s, 1H). |
| 017 | 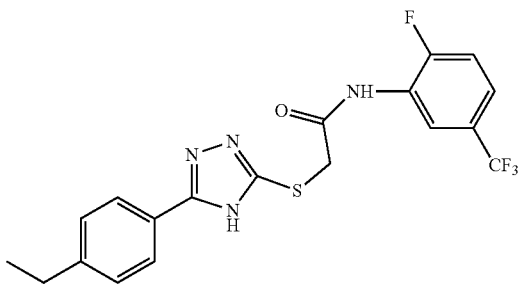 [SMILES: CCc1ccc(-c2nnc(SCC(=O)Nc3cc(C(F)(F)F)ccc3F)[nH]2)cc1]<br>2-[5-(4-Ethyl-phenyl)-4H-[1,2,4]triazol-3-ylsulfanyl]-N-(2-fluoro-5-trifluoromethyl-phenyl)-acetamide. It was prepared using Scheme-2 as white solid. 1H NMR (300 MHz, DMSO-d$_6$) δ 1.20 (t, J = 7.5 Hz, 3H), 2.65 (q, J = 7.5 Hz, 2H), 4.20 (s, 2H), 7.33-7.36 (m, 2H), 7.52-7.56 (m, 2H), 7.85 (s, 1H), 7.87 (s, 1H), 8.41-8.44 (m, 1H), 10.43 (s, 1H), 14.44 (br s, 1H). |
| 018 | 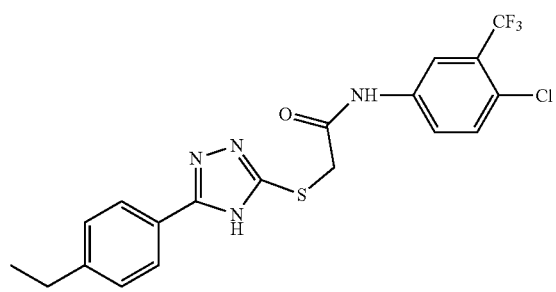 [SMILES: CCc1ccc(-c2nnc(SCC(=O)Nc3ccc(Cl)c(C(F)(F)F)c3)[nH]2)cc1]<br>N-(4-Chloro-3-trifluoromethyl-phenyl)-2-[5-(4-ethyl-phenyl)-4H-[1,2,4]triazol-3-ylsulfanyl]-acetamide. It was prepared using Scheme-2 as white solid. 1H NMR (300 MHz, DMSO-d$_6$) δ 1.20 (t, J = 7.5 Hz, 3H), 2.66 (q, J = 7.5 Hz, 2H), 4.21 (s, 2H), 7.31-7.37 (m, 2H), 7.68 (d, J = 9.0 Hz, 1H), 7.84 (d, J = 9.0 Hz, 3H), 8.19 (s, 1H), 10.75 (s, 1H), 14.43 (s, 1H). |

TABLE 3-continued

020

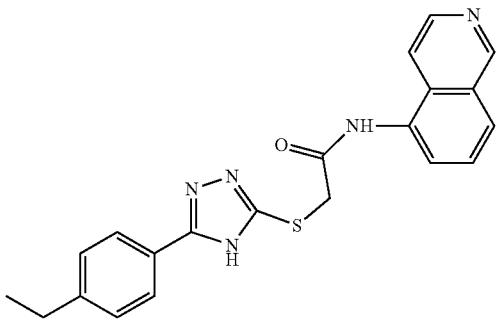 [SMILES: CCc1ccc(-c2nnc(SCC(=O)Nc3cccc4cnccc34)[nH]2)cc1]

2-[5-(4-Ethyl-phenyl)-4H-[1,2,4]triazol-3-ylsulfanyl]-N-isoquinolin-5-yl-acetamide. It was prepared using Scheme-2 as white solid. 1H NMR (300 MHz, DMSO-$d_6$) δ 1.21 (t, J = 7.5 Hz, 3H), 2.66 (q, J = 7.5 Hz, 2H), 4.25 (s, 2H), 7.30-7.40 (m, 2H), 7.69 (t, J = 8.1 Hz, 2H), 7.89-7.97 (m, 5H), 8.31-8.40 (m, 1H), 9.31 (s, 1H), 14.50 (s, 1H).

022

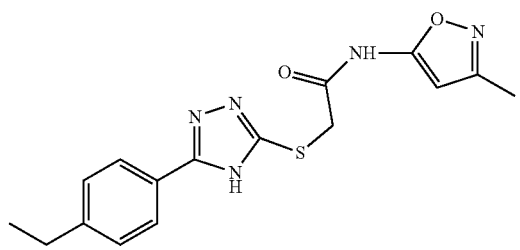 [SMILES: CCc1ccc(-c2nnc(SCC(=O)Nc3cc(C)no3)[nH]2)cc1]

2-[5-(4-Ethyl-phenyl)-4H-[1,2,4]triazol-3-ylsulfanyl]-N-(3-methyl-isoxazol-5-yl)-acetamide. It was prepared using Scheme-2 as white solid. 1H NMR (300 MHz, DMSO-$d_6$) δ 1.23 (m, 3H), 2.17 (q, J = 4.2 Hz, 3H), 2.62-2.70 (m, 2H), 4.13 (s, 2H), 6.11 (s, 1H), 7.34-7.45 (m, 2H), 7.84 (d, J = 8.4 Hz, 2H), 11.87 (s, 1H), 14.41 (s, 1H).

024

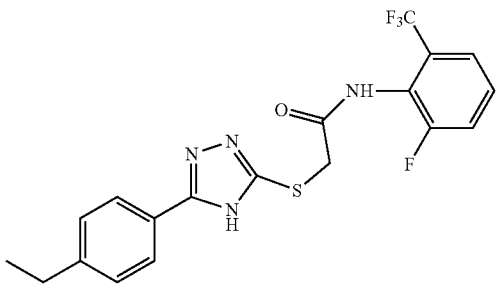 [SMILES: CCc1ccc(-c2nnc(SCC(=O)Nc3c(F)cccc3C(F)(F)F)[nH]2)cc1]

2-[5-(4-Ethyl-phenyl)-4H-[1,2,4]triazol-3-ylsulfanyl]-N-(2-fluoro-6-trifluoromethyl-phenyl)-acetamide. It was prepared using Scheme-2 as white solid. 1H NMR (300 MHz, DMSO-$d_6$) δ 1.21 (t, J = 7.5 Hz, 3H), 2.66 (q, J = 7.5 Hz, 2H), 4.15 (s, 2H), 7.36-7.39 (m, 2H), 7.59-7.65 (m, 3H), 7.88-7.90 (m, 2H), 10.02 (s, 1H), 14.41 (s, 1H).

025

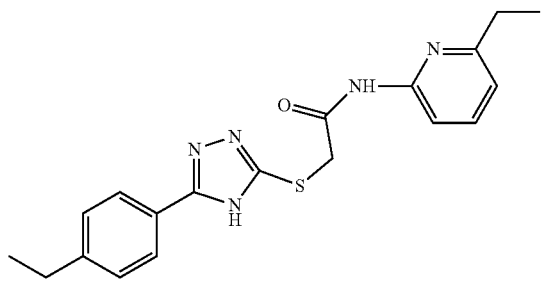 [SMILES: CCc1ccc(-c2nnc(SCC(=O)Nc3cccc(CC)n3)[nH]2)cc1]

2-[5-(4-Ethyl-phenyl)-4H-[1,2,4]triazol-3-ylsulfanyl]-N-(6-ethyl-pyridin-2-yl)-acetamide. It was prepared using Scheme-2 as white solid. 1H NMR (300 MHz, DMSO-$d_6$) δ 1.20 (t, J = 7.5 Hz, 6H), 2.62-2.72 (m, 4H), 4.12 (s, 2H), 6.99 (d, J = 7.5 Hz, 1H), 7.34 (d, J = 8.1 Hz, 2H), 7.69 (t, J = 7.8 Hz, 1H), 7.86-7.92 (m, 3H), 10.77 (s, 1H), 14.36 (br s, 1H).

TABLE 3-continued

028

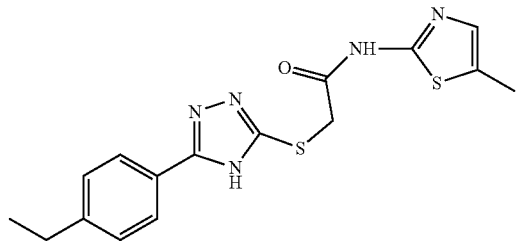 [SMILES: CCc1ccc(-c2nnc(SCC(=O)Nc3ncc(C)s3)[nH]2)cc1]

2-[5-(4-Ethyl-phenyl)-4H-[1,2,4]triazol-3-ylsulfanyl]-N-(5-methyl-thiazol-2-yl)-acetamide. It was prepared using Scheme-2 as white solid. 1H NMR (300 MHz, DMSO-$d_6$) δ 1.17-1.23 (m, 3H), 2.33 (s, 3H), 2.65 (q, J = 7.5 Hz, 2H), 4.14 (s, 2H), 7.15 (s, 1H), 7.36 (d, J = 8.1 Hz, 2H), 7.84 (d, J = 8.1 Hz, 2H), 12.20 (s, 1H), 14.43 (s, 1H).

029

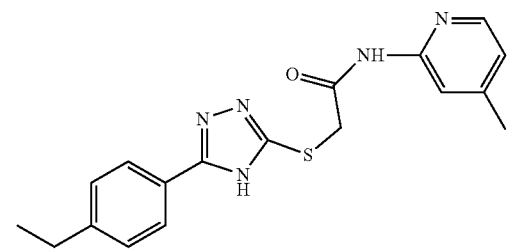 [SMILES: CCc1ccc(-c2nnc(SCC(=O)Nc3cc(C)ccn3)[nH]2)cc1]

2-[5-(4-Ethyl-phenyl)-4H-[1,2,4]triazol-3-ylsulfanyl]-N-(4-methyl-pyridin-2-yl)-acetamide. It was prepared using Scheme-2 as white solid. 1H NMR (300 MHz, DMSO-$d_6$) δ 1.20 (t, J = 7.5 Hz, 3H), 2.30 (s, 3H), 2.66 (q, J = 7.5 Hz, 2H), 4.11 (s, 2H), 6.95-6.96 (m, 1H), 7.35-7.38 (m, 2H), 7.87-7.89 (m, 3H), 8.17-8.19 (m, 1H), 10.70 (s, 1H), 14.44 (s, 1H).

031

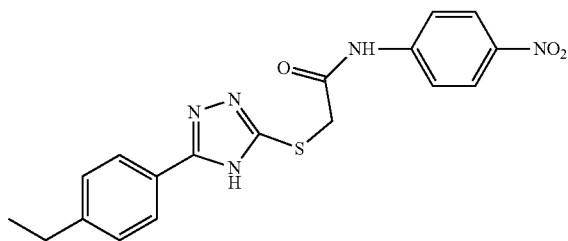 [SMILES: CCc1ccc(-c2nnc(SCC(=O)Nc3ccc([N+](=O)[O-])cc3)[nH]2)cc1]

2-[5-(4-Ethyl-phenyl)-4H-[1,2,4]-triazol-3-ylsulfanyl]-N-(4-nitro-phenyl)-acetamide. It was prepared using Scheme-2 as white solid. 1H NMR (300 MHz, DMSO-$d_6$) δ 1.20 (t, J = 7.5 Hz, 3H), 2.65 (q, J = 7.5 Hz, 2H), 4.16 (s, 2H), 7.36 (d, J = 8.1 Hz, 2H), 7.82-7.87 (m, 4H), 8.22-8.26 (m, 2H), 10.92 (s, 1H), 14.44 (br s, 1H).

032

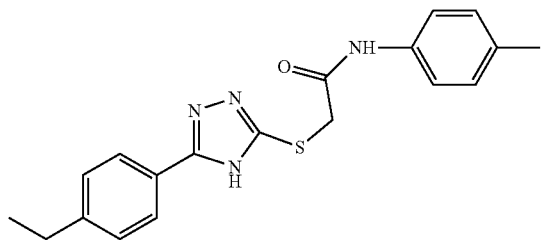 [SMILES: CCc1ccc(-c2nnc(SCC(=O)Nc3ccc(C)cc3)[nH]2)cc1]

2-[5-(4-Ethyl-phenyl)-4H-[1,2,4]triazol-3-ylsulfanyl]-N-p-tolyl-acetamide. It was prepared using Scheme-2 as white solid. 1H NMR (300 MHz, DMSO-$d_6$) δ 1.20 (t, J = 7.5 Hz, 3H), 2.25 (s, 3H), 2.65 (q, J = 7.5 Hz, 2H), 4.09 (s, 2H), 7.11 (d, J = 8.4 Hz, 2H), 7.35 (d, J = 7.8 Hz, 2H), 7.47 (d, J = 8.4 Hz, 2H), 7.86 (d, J = 8.1 Hz, 2H), 10.22 (s, 1H), 14.36 (br s, 1H).

034

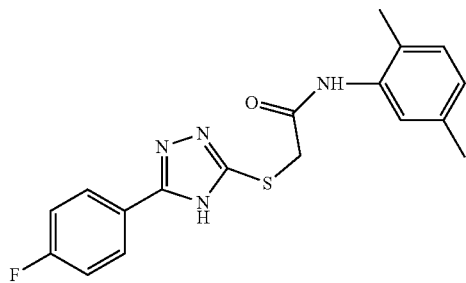 [SMILES: Cc1ccc(C)c(NC(=O)CSc2nnc(-c3ccc(F)cc3)[nH]2)c1]

N-(2,5-Dimethyl-phenyl)-2-[5-(4-fluoro-phenyl)-4H-[1,2,4]triazol-3-ylsulfanyl]-acetamide. It was prepared using Scheme-2 as white solid. 1H NMR (300 MHz, DMSO-d$_6$) δ 2.10 (s, 3H), 2.22 (s, 3H), 4.13 (s, 2H), 6.89 (d, J = 7.8 Hz, 1H), 7.06 (d, J = 7.5 Hz, 1H), 7.23 (s, 1H), 7.37 (br s, 2H), 8.00-8.04 (m, 2H), 9.54 (s, 1H), 14.50 (br s, 1H).

035

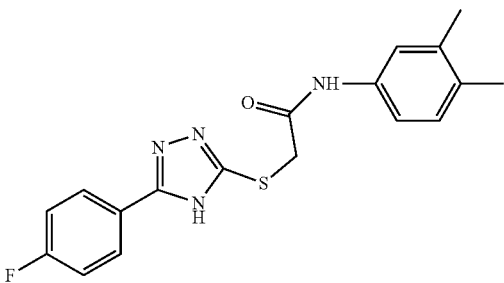 [SMILES: Cc1ccc(NC(=O)CSc2nnc(-c3ccc(F)cc3)[nH]2)cc1C]

N-(3,4-Dimethyl-phenyl)-2-[5-(4-fluoro-phenyl)-4H-[1,2,4]triazol-3-ylsulfanyl]-acetamide. It was prepared using Scheme-2 as white solid. 1H NMR (300 MHz, DMSO-d$_6$) δ 2.16 (s, 6H), 4.09 (s, 2H), 7.05 (d, J = 8.1 Hz, 1H), 7.27-7.35 (m, 4H), 7.97-8.02 (m, 2H), 10.14 (s, 1H), 14.37 (br s, 1H).

036

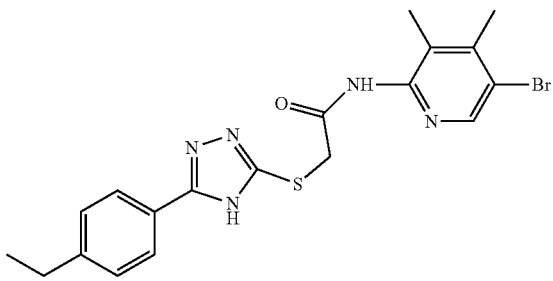 [SMILES: CCc1ccc(-c2nnc(SCC(=O)Nc3ncc(Br)c(C)c3C)[nH]2)cc1]

N-(5-Bromo-3,4-dimethyl-pyridin-2-yl)-2-[5-(4-ethyl-phenyl)-4H-[1,2,4]triazol-3-ylsulfanyl]-acetamide. It was prepared using Scheme-2 as white solid. 1H NMR (300 MHz, CDCl$_3$) δ 1.24 (t, J = 7.5 Hz, 3H), 2.19 (s, 3H), 2.38 (s, 3H), 2.66 (q, J = 7.5 Hz, 2H), 3.92 (s, 2H), 7.20-7.26 (m, 2H), 7.77 (d, J = 8.1 Hz, 2H), 8.30 (s, 1H), 10.09 (s, 1H).

037

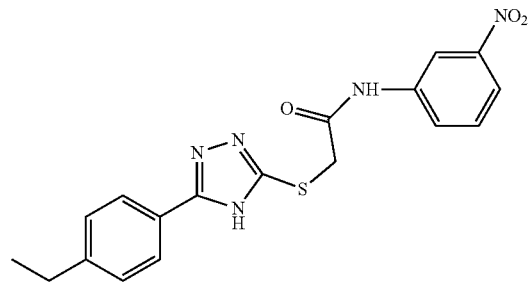 [SMILES: CCc1ccc(-c2nnc(SCC(=O)Nc3cccc([N+](=O)[O-])c3)[nH]2)cc1]

2-[5-(4-Ethyl-phenyl)-4H-[1,2,4]triazol-3-ylsulfanyl]-N-(3-nitro-phenyl)-acetamide. It was prepared using Scheme-2 as white solid. 1H NMR (300 MHz, DMSO-d$_6$) δ 1.20 (t, J = 7.5 Hz, 3H), 2.65 (q, J = 7.5 Hz, 2H), 4.14 (s, 2H), 7.32-7.35 (m, 2H), 7.62 (t, J = 8.4 Hz, 1H), 7.83-7.95 (m, 4H), 8.62 (s, 1H), 10.80 (s, 1H), 14.40 (br s, 1H).

TABLE 3-continued

038

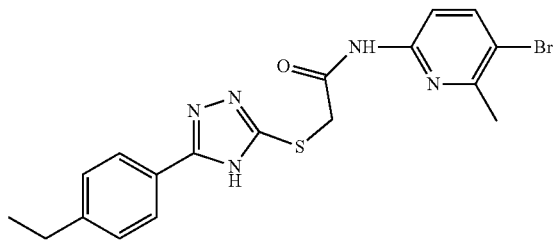 [SMILES: CCc1ccc(-c2nnc(SCC(=O)Nc3ccc(Br)c(C)n3)[nH]2)cc1]

N-(5-Bromo-6-methyl-pyridin-2-yl)-2-[5-(4-ethyl-phenyl)-4H-
[1,2,4]triazol-3-ylsulfanyl]-acetamide. It was prepared using Scheme-2 as white solid.
1H NMR (300 MHz, CDCl$_3$) δ 1.27 (t, J = 7.5 Hz, 3H), 2.53 (s, 3H), 2.71 (q, J = 7.5 Hz,
2H), 4.33 (s, 2H), 7.26-7.32 (m, 2H), 7.76 (d, J = 8.7 Hz, 1H), 7.94-8.04 (m, 3H), 10.93
(s, 1H).

039

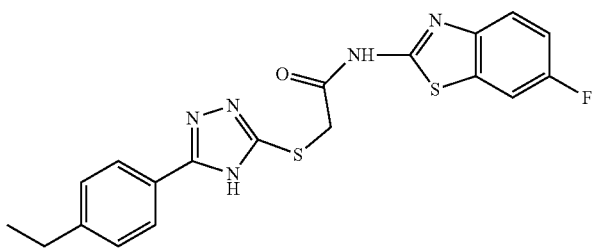 [SMILES: CCc1ccc(-c2nnc(SCC(=O)Nc3nc4ccc(F)cc4s3)[nH]2)cc1]

2-[5-(4-Ethyl-phenyl)-4H-[1,2,4]triazol-3-ylsulfanyl]-N-(6-fluoro-
benzothiazol-2-yl)-acetamide. It was prepared using Scheme-2 as white solid.
1H NMR (300 MHz, DMSO-d$_6$) δ 1.18 (t, J = 7.5 Hz, 3H), 2.63 (q, J = 7.5 Hz, 2H),
4.25 (s, 2H), 7.27-7.34 (m, 3H), 7.76-7.92 (m, 4H), 12.72 (s, 1H), 14.45 (s, 1H).

040

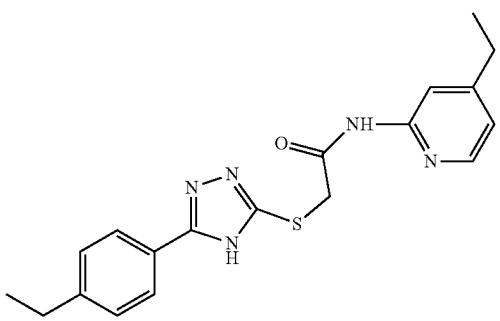 [SMILES: CCc1ccc(-c2nnc(SCC(=O)Nc3cc(CC)ccn3)[nH]2)cc1]

2-[5-(4-Ethyl-phenyl)-4H-[1,2,4]triazol-3-ylsulfanyl]-N-(4-ethyl-pyridin-2-
yl)-acetamide. It was prepared using Scheme-2 as white solid. 1H NMR (300 MHz,
DMSO-d$_6$) δ 1.14-1.23 (m, 6H), 2.59-2.66 (m, 4H), 4.12 (s, 2H), 6.99 (dd, J = 5.1,
1.2 Hz, 1H), 7.35-7.37 (m, 2H), 7.87-7.94 (m, 3H), 8.21 (d, J = 5.1 Hz, 1H), 10.71
(s, 1H), 14.43 (s, 1H).

042

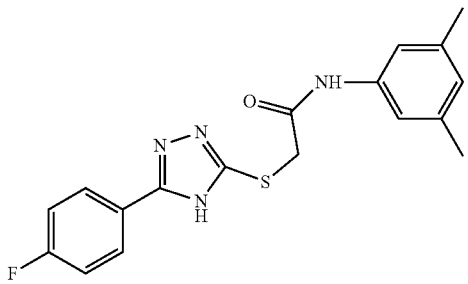 [SMILES: Cc1cc(C)cc(NC(=O)CSc2nnc(-c3ccc(F)cc3)[nH]2)c1]

N-(3,5-Dimethyl-phenyl)-2-[5-(4-fluoro-phenyl)-4H-[1,2,4]triazol-3-
ylsulfanyl]-acetamide. It was prepared using Scheme-2 as white solid. 1H NMR
(300 MHz, DMSO-d$_6$) δ 2.22 (s, 6H), 4.09 (s, 2H), 6.70 (s, 1H), 7.20 (s, 2H), 7.30-7.40
(m, 2H), 7.97-8.02 (m, 2H), 10.13 (s, 1H), 14.40 (br s, 1H).

044

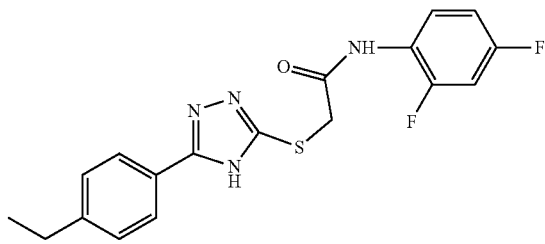 [SMILES: CCc1ccc(-c2nnc(SCC(=O)Nc3ccc(F)cc3F)[nH]2)cc1]

N-(2,4-Difluoro-phenyl)-2-[5-(4-ethyl-phenyl)-4H-[1,2,4]triazol-3-ylsulfanyl]-acetamide. It was prepared using Scheme-2 as white solid. 1H NMR (300 MHz, DMSO-$d_6$) δ 1.21 (t, J = 7.5 Hz, 3H), 2.66 (q, J = 7.5 Hz, 2H), 4.15 (s, 2H), 7.02-7.10 (m, 1H), 7.29-7.37 (m, 3H), 7.84-7.89 (m, 3H), 10.10 (s, 1H), 14.40 (br s, 1H).

046

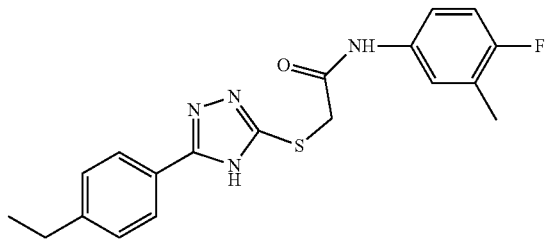 [SMILES: CCc1ccc(-c2nnc(SCC(=O)Nc3ccc(F)c(C)c3)[nH]2)cc1]

2-[5-(4-Ethyl-phenyl)-4H-[1,2,4]triazol-3-ylsulfanyl]-N-(4-fluoro-3-methyl-phenyl)-acetamide. It was prepared using Scheme-2 as white solid. 1H NMR (300 MHz, DMSO-$d_6$) δ 1.20 (t, J = 7.5 Hz, 3H), 2.20 (s, 3H), 2.65 (q, J = 7.5 Hz, 2H), 4.08 (s, 2H), 7.05-7.11 (m, 1H), 7.34-7.51 (m, 4H), 7.86 (d, J = 8.1 Hz, 2H), 10.29 (s, 1H), 14.36 (br s, 1H).

047

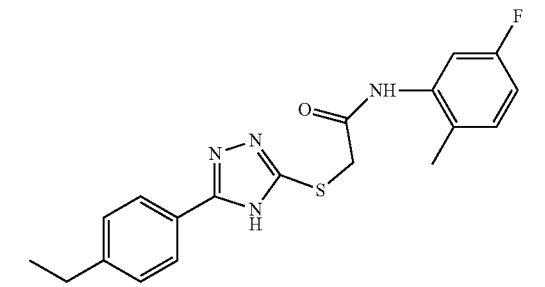 [SMILES: CCc1ccc(-c2nnc(SCC(=O)Nc3cc(F)ccc3C)[nH]2)cc1]

2-[5-(4-Ethyl-phenyl)-4H-[1,2,4]triazol-3-ylsulfanyl]-N-(5-fluoro-2-methyl-phenyl)-acetamide. It was prepared using Scheme-2 as white solid. 1H NMR (300 MHz, DMSO-$d_6$) δ 1.20 (t, J = 7.5 Hz, 3H), 2.50 (s, 3H), 2.65 (q, J = 7.5 Hz, 2H), 4.14 (s, 2H), 6.87-6.93 (m, 1H), 7.34-7.45 (m, 3H), 7.19-7.24 (m, 1H), 7.86-7.89 (m, 2H), 9.63 (s, 1H), 14.34 (br s, 1H).

048

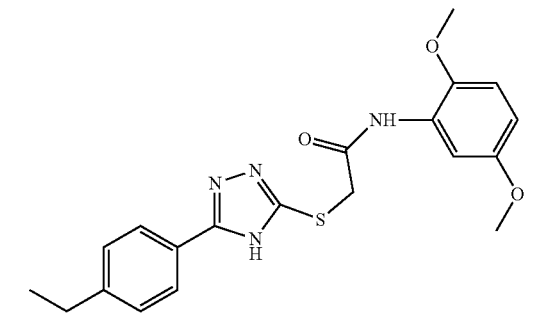 [SMILES: CCc1ccc(-c2nnc(SCC(=O)Nc3cc(OC)ccc3OC)[nH]2)cc1]

N-(2,5-Dimethoxy-phenyl)-2-[5-(4-ethyl-phenyl)-4H-[1,2,4]triazol-3-ylsulfanyl]-acetamide. It was prepared using Scheme-2 as white solid. 1H NMR (300 MHz, DMSO-$d_6$) δ 1.18-1.23 (m, 3H), 2.11 (s, 3H), 2.65-2.67 (m, 2H), 3.71 (s, 3H), 4.06 (s, 2H), 6.71-6.78 (m, 2H), 7.21-7.39 (m, 3H), 7.87-7.90 (m, 2H), 9.47 (s, 1H), 14.43 (s, 1H).

TABLE 3-continued

051

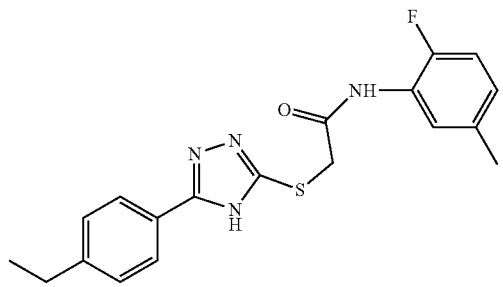 [SMILES: CCc1ccc(-c2nnc(SCC(=O)Nc3cc(C)ccc3F)[nH]2)cc1]

2-[5-(4-Ethyl-phenyl)-4H-[1,2,4]triazol-3-ylsulfanyl]-N-(2-fluoro-5-methyl-phenyl)-acetamide. It was prepared using Scheme-2 as white solid. 1H NMR (300 MHz, DMSO-$d_6$) δ 1.20 (t, J = 7.5 Hz, 3H), 2.25 (s, 3H), 2.66 (q, J = 7.5 Hz, 2H), 4.15 (s, 2H), 6.95-6.96 (m, 1H), 7.09-7.16 (m, 1H), 7.35 (d, J = 8.1 Hz, 2H), 7.74 (d, J = 6.3 Hz, 1H), 7.88 (d, J = 8.1 Hz, 2H), 10.02 (s, 1H), 14.30 (s, 1H).

052

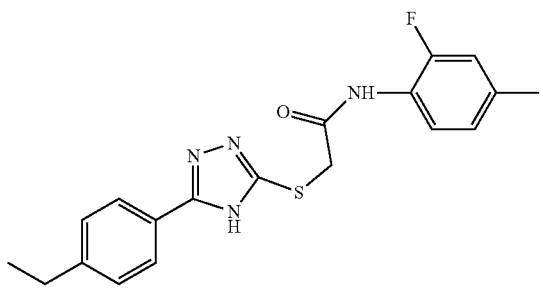 [SMILES: CCc1ccc(-c2nnc(SCC(=O)Nc3ccc(C)cc3F)[nH]2)cc1]

2-[5-(4-Ethyl-phenyl)-4H-[1,2,4]triazol-3-ylsulfanyl]-N-(2-fluoro-4-methyl-phenyl)-acetamide. It was prepared using Scheme-2 as white solid. 1H NMR (300 MHz, DMSO-$d_6$) δ 1.20 (t, J = 7.8 Hz, 3H), 2.27 (s, 3H), 2.66 (q, J = 7.8 Hz, 2H), 4.14 (s, 2H), 6.97 (d, J = 8.4 Hz, 1H), 7.08 (d, J = 12.0 Hz, 1H), 7.35 (d, J = 7.8 Hz, 2H), 7.75 (d, J = 8.1 Hz, 1H), 7.88 (d, J = 8.1 Hz, 2H), 9.99 (s, 1H), 14.41 (s, 1H).

056

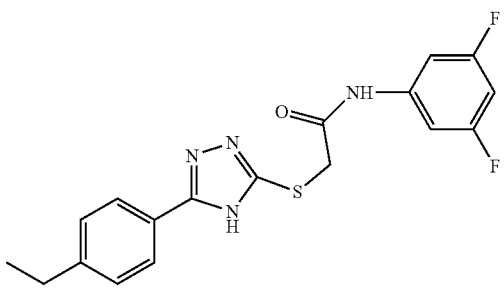 [SMILES: CCc1ccc(-c2nnc(SCC(=O)Nc3cc(F)cc(F)c3)[nH]2)cc1]

N-(3,5-Difluoro-phenyl)-2-[5-(4-ethyl-phenyl)-4H-[1,2,4]triazol-3-ylsulfanyl]-acetamide. It was prepared using Scheme-2 as white solid. 1H NMR (300 MHz, DMSO-$d_6$) δ 1.27 (t, J = 7.5 Hz, 3H), 2.71 (q, J = 7.5 Hz, 2H), 3.86 (s, 2H), 6.50-6.54 (m, 1H), 7.14-7.21 (m, 2H), 7.30-7.34 (m, 2H), 7.93 (d, J = 8.4 Hz, 2H), 10.78 (s, 1H), 14.15 (s, 1H).

057

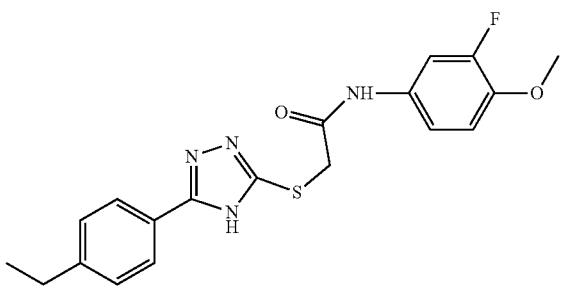 [SMILES: CCc1ccc(-c2nnc(SCC(=O)Nc3ccc(OC)c(F)c3)[nH]2)cc1]

2-[5-(4-Ethyl-phenyl)-4H-[1,2,4]triazol-3-ylsulfanyl]-N-(3-fluoro-4-methoxy-phenyl)-acetamide. It was prepared using Scheme-2 as white solid. 1H NMR (300 MHz, DMSO-$d_6$) δ 1.27 (t, J = 7.5 Hz, 3H), 2.71 (q, J = 7.5 Hz, 2H), 3.85 (d, J = 8.1 Hz, 5H), 6.86 (t, J = 9.0 Hz, 1H), 7.12-7.16 (m, 1H), 7.29-7.35 (m, 2H), 7.47-7.52 (dd, J = 12.9, 2.4 Hz, 1H), 7.94 (d, J = 8.4 Hz, 2H), 10.35 (s, 1H), 14.07 (s, 1H).

058

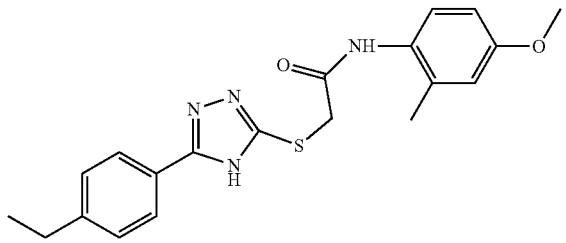 [SMILES: CCc1ccc(-c2nnc(SCC(=O)Nc3ccc(OC)cc3C)[nH]2)cc1]

2-[5-(4-Ethyl-phenyl)-4H-[1,2,4]triazol-3-ylsulfanyl]-N-(4-methoxy-2-methyl-phenyl)-acetamide. It was prepared using Scheme-2 as white solid. 1H NMR (300 MHz, DMSO-$d_6$) δ 1.20 (t, J = 7.5 Hz, 3H), 2.66 (q, J = 7.5 Hz, 2H), 3.66 (d, J = 2.4 Hz, 6H), 4.13 (s, 2H), 6.59-6.62 (dd, J = 8.7, 3.0 Hz, 1H), 6.92 (d, J = 9.0 Hz, 1H), 7.36 (d, J = 7.8 Hz, 2H), 7.79 (d, J = 2.7 Hz, 1H), 7.89 (d, J = 8.1 Hz, 2H), 9.51 (s, 1H), 14.44 (s, 1H).

059

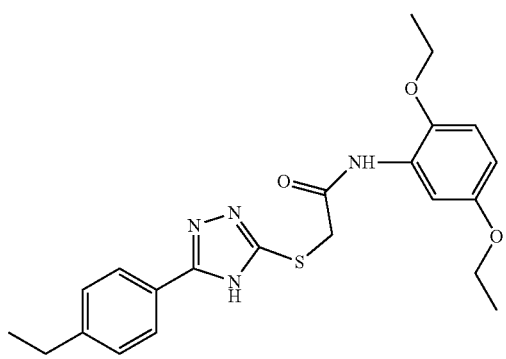 [SMILES: CCOc1ccc(OCC)c(NC(=O)CSc2nnc(-c3ccc(CC)cc3)[nH]2)c1]

N-(2,5-Diethoxy-phenyl)-2-[5-(4-ethyl-phenyl)-4H-[1,2,4]triazol-3-ylsulfanyl]-acetamide. It was prepared using Scheme-2 as white solid. 1H NMR (300 MHz, DMSO-$d_6$) δ 1.16-1.28 (m, 9H), 2.62-2.69 (m, 2H), 3.90-3.97 (m, 4H), 4.11 (brs, 2H), 6.56-6.60 (dd, J = 9.0, 3.0 Hz, 1H), 6.91 (d, J = 9.0 Hz, 1H), 7.36 (d, J = 6.3 Hz, 2H), 7.77 (br s, 1H), 7.87 (d, J = 8.1 Hz, 2H), 9.38 (s, 1H), 14.47 (s, 1H).

060

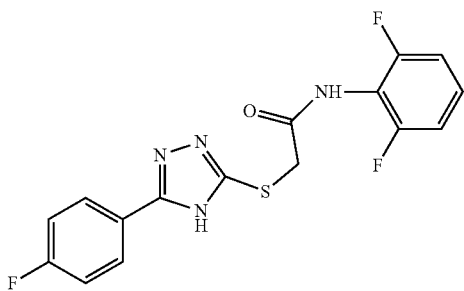 [SMILES: O=C(CSc1nnc(-c2ccc(F)cc2)[nH]1)Nc1c(F)cccc1F]

N-(2,6-Difluoro-phenyl)-2-[5-(4-fluoro-phenyl)-4H-[1,2,4]triazol-3-ylsulfanyl]-acetamide. It was prepared using Scheme-2 as white solid. 1H NMR (300 MHz, DMSO-$d_6$) δ 3.98 (s, 2H), 6.97-6.99 (m, 2H), 7.11-7.25 (m, 3H), 8.00-8.05 (m, 2H), 9.80 (s, 1H), 14.31 (s, 1H).

065

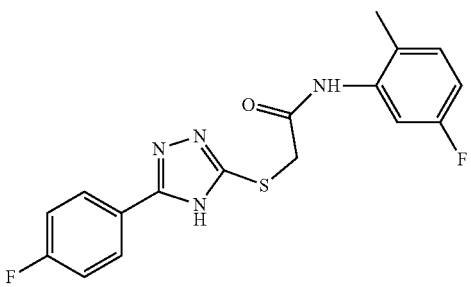 [SMILES: Cc1ccc(F)cc1NC(=O)CSc1nnc(-c2ccc(F)cc2)[nH]1]

N-(5-Fluoro-2-methyl-phenyl)-2-[5-(4-fluoro-phenyl)-4H-[1,2,4]triazol-3-ylsulfanyl]-acetamide. It was prepared using Scheme-2 as white solid. 1H NMR (300 MHz, CDCl$_3$) δ 2.05 (s, 3H), 3.98 (s, 2H), 6.72-6.76 (m, 1H), 7.01-7.06 (m, 1H), 7.13 (t, J = 8.7 Hz, 2H), 7.97-8.02 (m, 3H), 9.31 (s, 1H), 14.20 (br s, 1H).

TABLE 3-continued

069

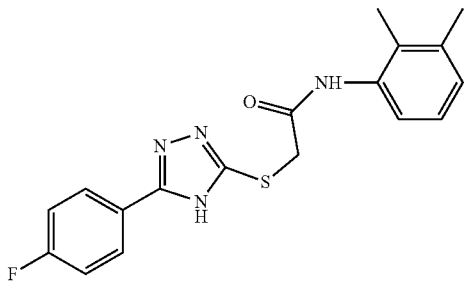 [SMILES: Cc1cccc(NC(=O)CSc2nnc(-c3ccc(F)cc3)[nH]2)c1C]

N-(2,3-Dimethyl-phenyl)-2-[5-(4-fluoro-phenyl)-4H-[1,2,4]triazol-3-ylsulfanyl]-acetamide. It was prepared using Scheme-2 as white solid. 1H NMR (300 MHz, CDCl$_3$) δ 2.05 (s, 3H), 2.42 (s, 3H), 3.97 (s, 2H), 6.97-6.99 (m, 1H), 7.05-7.15 (m, 3H), 7.42-7.51 (m, 1H), 7.93-8.04 (m, 2H), 9.21 (s, 1H), 14.20 (br s, 1H).

072

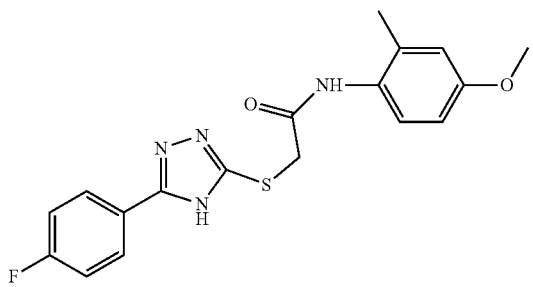 [SMILES: COc1ccc(NC(=O)CSc2nnc(-c3ccc(F)cc3)[nH]2)c(C)c1]

2-[5-(4-Fluoro-phenyl)-4H-[1,2,4]triazol-3-ylsulfanyl]-N-(4-methoxy-2-methyl-phenyl)-acetamide. It was prepared using Scheme-2 as white solid. 1H NMR (300 MHz, DMSO-d$_6$) δ 2.11 (s, 3H), 3.71 (s, 3H), 4.11 (s, 2H), 6.68-6.78 (m, 2H), 7.22 (d, J = 8.4 Hz, 1H), 7.36 (t, J = 8.7 Hz, 2H), 7.99-8.04 (m, 2H), 9.51 (s, 1H), 14.39 (br s, 1H).

073

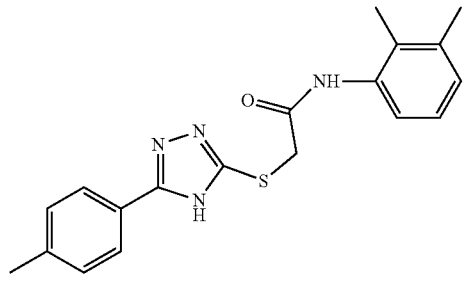

N-(2,3-Dimethyl-phenyl)-2-(5-p-tolyl-4H-[1,2,4]triazol-3-ylsulfanyl)-acetamide. It was prepared using Scheme-2 as white solid. 1H NMR (300 MHz, CDCl$_3$) δ 2.03 (s, 3H), 2.23 (s, 3H), 2.39 (s, 3H), 3.96 (s, 2H), 6.95-6.98 (m, 1H), 7.06 (t, J = 7.8 Hz, 1H), 7.21-7.27 (m, 2H), 7.46 (d, J = 9.0 Hz, 1H), 7.85 (s, 1H), 7.88 (s, 1H), 9.42 (s, 1H), 14.09 (br s, 1H).

074

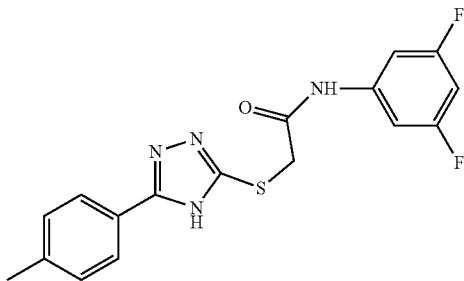 [SMILES: Cc1ccc(-c2nnc(SCC(=O)Nc3cc(F)cc(F)c3)[nH]2)cc1]

N-(3,5-Difluoro-phenyl)-2-(5-p-tolyl-4H-[1,2,4]triazol-3-ylsulfanyl)-acetamide. It was prepared using Scheme-2 as white solid. 1H NMR (300 MHz, CDCl$_3$) δ 2.42 (s, 3H), 3.86 (s, 2H), 6.52-6.54 (m, 1H), 7.14-7.23 (m, 2H), 7.28-7.31 (m, 2H), 7.88-7.91 (m, 2H), 10.70 (s, 1H), 14.22 (br s, 1H).

TABLE 3-continued

075

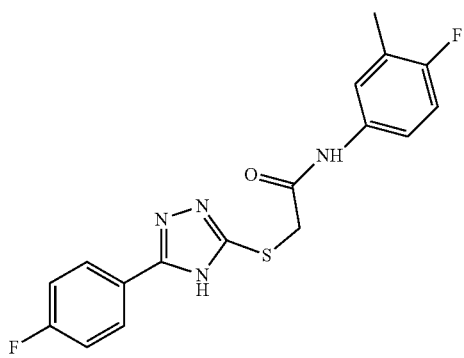 [SMILES: Cc1cc(NC(=O)CSc2nnc(-c3ccc(F)cc3)[nH]2)ccc1F]

N-(4-Fluoro-3-methyl-phenyl)-2-[5-(4-fluoro-phenyl)-4H-[1,2,4]triazol-3-ylsulfanyl]-acetamide. It was prepared using Scheme-2 as white solid. 1H NMR (300 MHz, DMSO-$d_6$) δ 2.19 (s, 3H), 4.10 (s, 2H), 7.08 (t, J = 9.1 Hz, 1H), 7.37 (m, 3H), 7.50 (m, 1H), 7.99 (m, 2H), 10.28 (s, 1H), 14.37 (br. s, 1H).

077

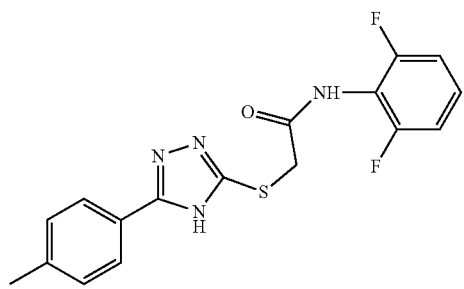 [SMILES: Cc1ccc(-c2nnc(SCC(=O)Nc3c(F)cccc3F)[nH]2)cc1]

N-(2,6-Difluoro-phenyl)-2-(5-p-tolyl-4H-[1,2,4]triazol-3-ylsulfanyl)-acetamide. It was prepared using Scheme-2 as white solid. 1H NMR (300 MHz, DMSO-$d_6$) δ 2.36 (s, 3H), 4.17 (s, 2H), 7.12-7.19 (m, 2H), 7.30-7.38 (m, 3H), 7.86 (s, 1H), 7.89 (s, 1H), 10.06 (s, 1H), 14.26 (br. s, 1H).

079

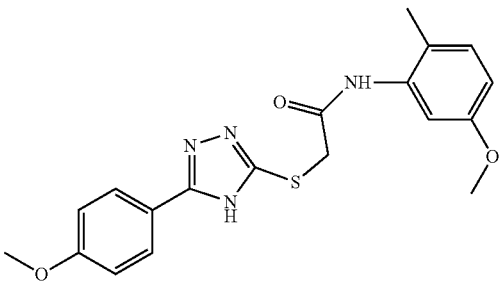 [SMILES: COc1ccc(-c2nnc(SCC(=O)Nc3cc(OC)ccc3C)[nH]2)cc1]

N-(5-Methoxy-2-methyl-phenyl)-2-[5-(4-methoxy-phenyl)-4H-[1,2,4]triazol-3-ylsulfanyl]-acetamide. It was prepared using Scheme-2 as white solid. 1H NMR (300 MHz, DMSO-$d_6$) δ 2.11 (s, 3H), 3.71 (s, 3H), 3.82 (s, 3H), 4.05 (s, 2H), 6.71-6.77 (m, 2H), 7.00-7.11 (m, 2H), 7.22-7.25 (m, 1H), 7.89 (s, 1H), 7.92 (s, 1H), 9.43 (s, 1H), 14.32 (s, 1H).

084

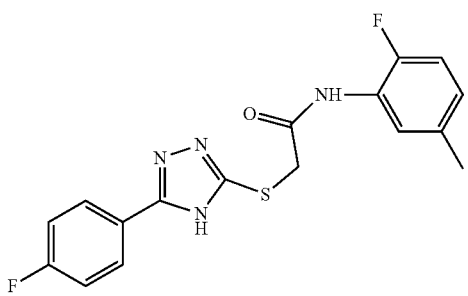 [SMILES: Cc1ccc(F)c(NC(=O)CSc2nnc(-c3ccc(F)cc3)[nH]2)c1]

N-2 Fluoro-5-methyl-phenyl)-2-[5-(4-fluoro-phenyl)-4H-[1,2,4]triazol-3-ylsulfanyl]-acetamide. It was prepared using Scheme-2 as white solid. 1H NMR (300 MHz, DMSO-$d_6$) δ 2.24 (s, 3H), 4.16 (s, 2H), 6.90-7.00 (m, 1H), 7.09-7.16 (m, 1H), 7.36 (m, 2H), 7.73 (d, J = 7.8 Hz, 1H), 7.98-8.03 (m, 2H), 10.01 (s, 1H), 14.41 (br s, 1H).

085

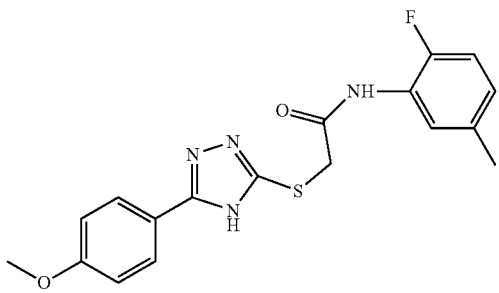

N-(2-Fluoro-5-methyl-phenyl)-2-[5-(4-methoxy-phenyl)-4H-[1,2,4]triazol-3-ylsulfanyl]-acetamide. It was prepared using Scheme-2 as white solid. 1H NMR (300 MHz, DMSO-$d_6$) δ 2.25 (s, 3H), 3.82 (s, 3H), 4.13 (s, 2H), 6.92-6.95 (m, 1H), 7.06-7.16 (m, 1H), 7.75 (d, J = 7.2 Hz, 1H), 7.89 (s, 1H),7.91 (s, 1H), 10.01 (s, 1H), 14.32 (br s, 1H).

086

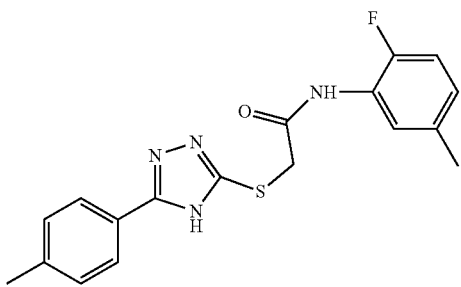

N-(2-Fluoro-5-methyl-phenyl)-2-(5-p-tolyl-4H-[1,2,4]triazol-3-ylsulfanyl)-acetamide. It was prepared using Scheme-2 as white solid. 1H NMR (300 MHz, DMSO-$d_6$) δ 2.25 (s, 3H), 2.36 (s, 3H), 4.16 (s, 2H), 6.91-6.96 (m, 1H), 7.09-7.16 (m, 1H), 7.30-7.33 (m, 2H), 7.74-7.77 (m, 1H), 7.85 (s, 1H), 7.88 (s, 1H), 10.01 (s, 1H), 14.31 (br.s, 1H).

088

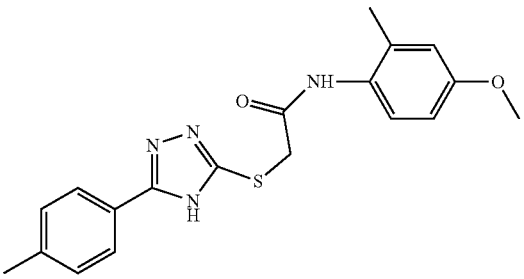

9N-(4-Methoxy-2-methyl-phenyl)-2-(5-p-tolyl-4H-[1,2,4]triazol-3-ylsulfanyl)-acetamide. It was prepared using Scheme-2 as white solid. 1H NMR (300 MHz, DMSO-$d_6$) δ 2.11 (s, 3H), 2.36 (s, 3H), 3.71 (s, 3H), 4.08 (s, 2H), 6.70-6.78 (m, 2H), 7.23 (d, J = 8.7 Hz, 1H), 7.31 (s, 1H), 7.34 (s, 1H), 7.85 (s, 1H), 7.88 (s, 1H), 9.52 (s, 1H), 14.31 (br s, 1H).

091

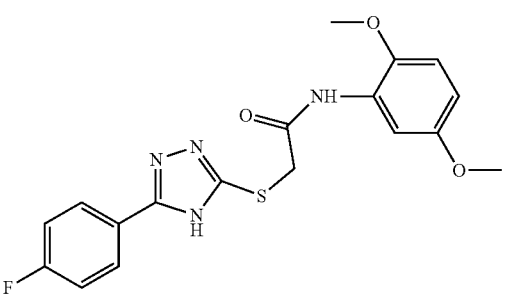 [SMILES: COc1ccc(OC)c(NC(=O)CSc2nnc(-c3ccc(F)cc3)[nH]2)c1]

N-(2,5-Dimethoxy-phenyl)-2-[5-(4-fluoro-phenyl)-4H-[1,2,4]triazol-3-ylsulfanyl]-acetamide. It was prepared using Scheme-2 as white solid. 1H NMR (300 MHz, DMSO-$d_6$) δ 3.66 (s, 6H), 4.13 (s, 2H), 6.61 (d, J = 7.2 Hz, 1H), 6.92 (d, J = 8.7 Hz, 1H), 7.37 (br s, 2H), 7.77 (s, 1H), 8.00-8.04 (m, 2H), 9.50 (s, 1H), 14.57 (br s, 1H).

TABLE 3-continued

094

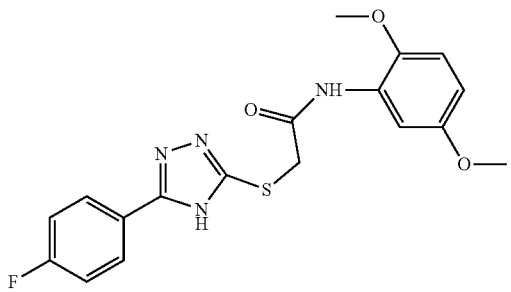 [SMILES: COc1ccc(OC)c(NC(=O)CSc2nnc(-c3ccc(F)cc3)[nH]2)c1]

N-(2,5-Dimethoxy-phenyl)-2-[5-(4-fluoro-phenyl)-4H-[1,2,4]triazol-3-ylsulfanyl]-acetamide. It was prepared using Scheme-2 as white solid. 1H NMR (300 MHz, DMSO-$d_6$) δ 2.36 (s, 3H), 3.66 (s, 6H), 4.12 (s, 2H), 6.61 (dd, J = 9.3 Hz, 3.0 Hz, 1H), 6.92 (d, J = 9.0 Hz, 1H), 7.32 (m, 2H), 7.78-7.88 (m, 3H), 9.50 (s, 1H), 14.43 (br s, 1H).

095

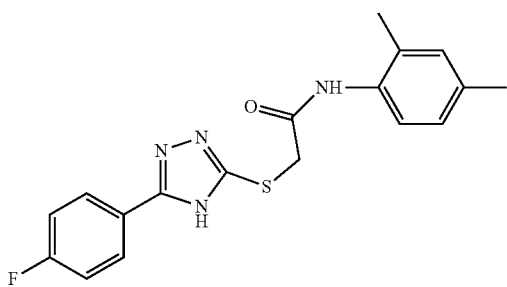 [SMILES: Cc1ccc(NC(=O)CSc2nnc(-c3ccc(F)cc3)[nH]2)c(C)c1]

N-(2,4-Dimethyl-phenyl)-2-[5-(4-fluoro-phenyl)-4H-[1,2,4]triazol-3-ylsulfanyl]-acetamide. It was prepared using Scheme-2 as white solid. 1H NMR (300 MHz, DMSO-$d_6$) δ 2.10 (s, 3H), 2.23 (s, 3H), 4.12 (s, 2H), 6.94-7.00 (m, 2H), 7.26 (d, J =7.8 Hz, 1H), 7.32 (m, 2H), 7.37 (t, J = 7.8 Hz, 2H), 7.99-8.04 (m, 2H), 9.52 (s, 1H), 14.36 (br s, 1H).

101

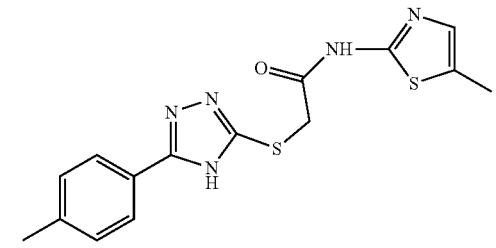

N-(5-Methyl-thiazol-2-yl)-2-(5-p-tolyl-4H-[1,2,4]triazol-3-ylsulfanyl)-acetamide. It was prepared using Scheme-2 as white solid. 1H NMR (300 MHz, DMSO-$d_6$) δ 2.33-2.35 (m, 6H), 4.16 (s, 2H), 7.14 (s, 1H), 7.30-7.32 (m, 2H), 7.81-7.83 (m, 2H), 12.10 (br s, 1H), 14.39 (br s, 1H).

102

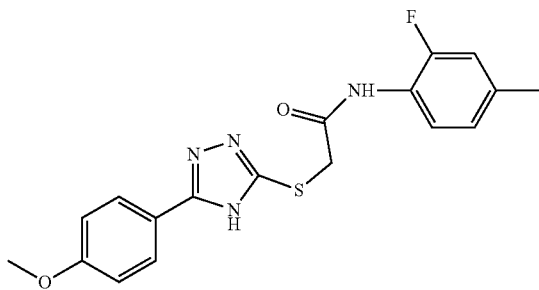

N-(2-Fluoro-4-methyl-phenyl)-2-[5-(4-methoxy-phenyl)-4H-[1,2,4]triazol-3-ylsulfanyl]-acetamide. It was prepared using Scheme-2 as white solid. 1H NMR (300 MHz, DMSO-$d_6$) δ 2.27 (s, 3H), 3.82 (s, 3H), 4.13 (s, 2H), 6.96 (d, J = 8.1 Hz, 1H), 7.06-7.10 (m, 3H), 7.76 (t, J = 8.4 Hz, 1H), 7.89-7.92 (m, 2H), 9.99 (s, 1H), 14.32 (br s, 1H).

| 107 | 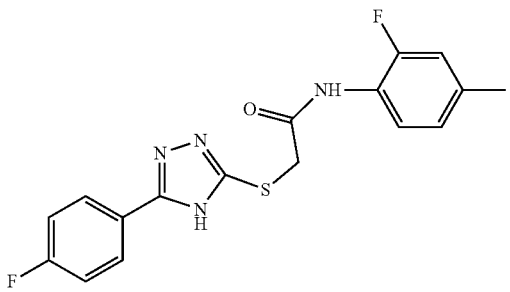 [SMILES: Cc1ccc(NC(=O)CSc2nnc(-c3ccc(F)cc3)[nH]2)c(F)c1]
N-(2-Fluoro-4-methyl-phenyl)-2-[5-(4-fluoro-phenyl)-4H-[1,2,4]triazol-3-ylsulfanyl]-acetamide. It was prepared using Scheme-2 as white solid. 1H NMR (300 MHz, DMSO-d$_6$) δ 2.27 (s, 3H) 4.15 (s, 2H), 6.96 (d, J = 8.40 Hz, 1H), 7.07 (d, J = 12.3 Hz, 1H), 7.35 (t, J = 9.0 Hz, 2H), 7.74 (t, J = 9.0 Hz, 1H), 7.98-8.03 (m, 2H), 9.98 (s, 1H), 14.43 (br s, 1H). |

| 112 | 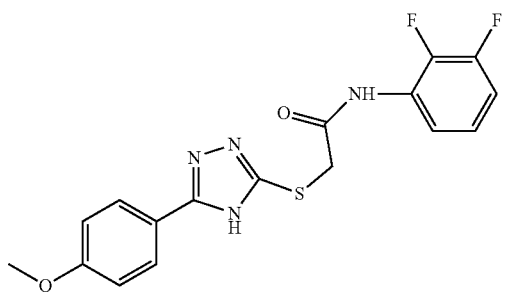 [SMILES: COc1ccc(-c2nnc(SCC(=O)Nc3cccc(F)c3F)[nH]2)cc1]
N-(2,3-Difluoro-phenyl)-2-[5-(4-methoxy-phenyl)-4H-[1,2,4]triazol-3-ylsulfanyl]-acetamide. It was prepared using Scheme-2 as white solid. 1H NMR (300 MHz, DMSO-d$_6$) δ 3.82 (s, 3H), 4.17 (s, 2H), 7.05-7.08 (m, 2H), 7.17 (t, J = 6.6 Hz, 2H), 7.72 (t, J = 7.2 Hz, 1H), 7.88 (s, 1H), 7.91 (s, 1H), 10.29 (s, 1H), 14.31 (br s, 1H). |

| 122 | 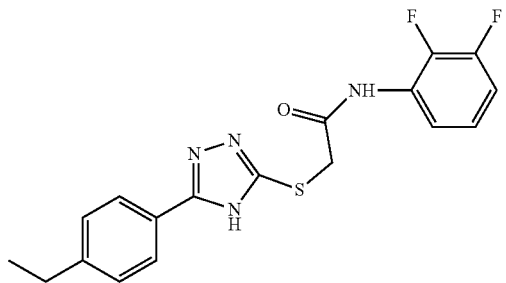 [SMILES: CCc1ccc(-c2nnc(SCC(=O)Nc3cccc(F)c3F)[nH]2)cc1]
N-(2,3-Difluoro-phenyl)-2-[5-(4-ethyl-phenyl)-4H-[1,2,4]triazol-3-ylsulfanyl]-acetamide. It was prepared using Scheme-2 as white solid. 1H NMR (300 MHz, DMSO-d$_6$) δ 1.20 (t, J = 7.5 Hz, 3H), 2.66 (q, J = 7.5 Hz, 2H), 4.17 (s, 2H), 6.96-7.00 (m, 1H), 7.29-7.37 (m, 3H), 7.86-7.92 (m, 3H), 10.27 (s, 1H), 14.46 (s, 1H). |

| 124 | 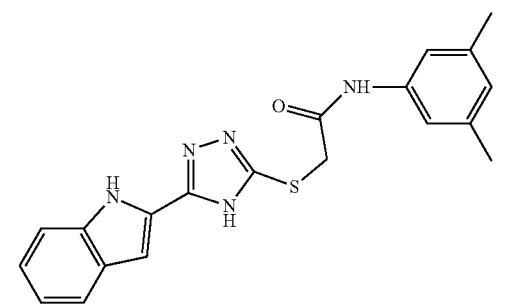 [SMILES: Cc1cc(C)cc(NC(=O)CSc2nnc(-c3cc4ccccc4[nH]3)[nH]2)c1]
N-(3,5-Dimethyl-phenyl)-2-[5-(1H-indol-2-yl)-4H-[1,2,4]triazol-3-ylsulfanyl]-acetamide. It was prepared using Scheme-2 as white solid. 1H NMR (300 MHz, DMSO-d$_6$) δ 2.21 (s, 6H), 4.08 (s, 2H), 6.70 (s, 1H), 6.88-7.21 (m, 5H), 7.43-7.64 (m, 2H), 10.10 (s, 1H), 11.86 (s, 1H), 14.52 (br s, 1H). |

| | |
|---|---|
| 131 | 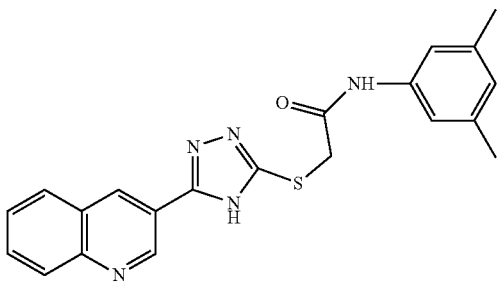 [SMILES: Cc1cc(C)cc(NC(=O)CSc2nnc(-c3cnc4ccccc4c3)[nH]2)c1] |

N-(3,5-Dimethyl-phenyl)-2-(5-quinolin-3-yl-4H-[1,2,4]triazol-3-ylsulfanyl)-acetamide. It was prepared using Scheme-2 as white solid. 1H NMR (300 MHz, DMSO-d$_6$) δ 2.22 (s, 6H), 4.17 (s, 2H), 6.70 (s, 1H), 7.23 (s, 2H), 7.69 (m, 2H), 8.06-8.10 (m, 2H), 8.88 (d, J = 1.8 Hz, 1H), 9.46 (d, J = 2.1 Hz, 1H), 10.20 (s, 1H).

| | |
|---|---|
| 132 | 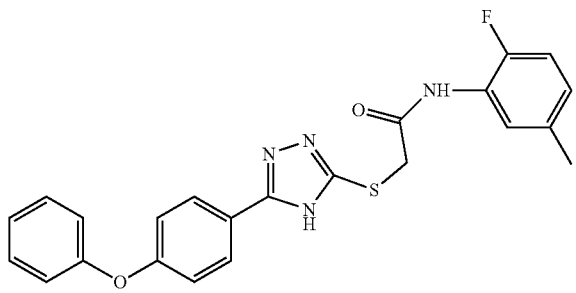 [SMILES: Cc1ccc(F)c(NC(=O)CSc2nnc(-c3ccc(Oc4ccccc4)cc3)[nH]2)c1] |

N-(2-Fluoro-5-methyl-phenyl)-2-[5-(4-phenoxy-phenyl)-4H-[1,2,4]triazol-3-ylsulfanyl]-acetamide. It was prepared using Scheme-2 as white solid. 1H NMR (300 MHz, DMSO-d$_6$) δ 2.24 (s, 3H), 4.13-4.22 (m, 2H), 6.93 (m, 1H), 7.09-7.24 (m, 6H), 7.42-7.47 (m, 2H), 7.74 (d, J = 6.3 Hz, 1H), 7.95-7.98 (m, 2H), 9.99 (s, 1H), 14.45 (s, 1H).

| | |
|---|---|
| 133 | 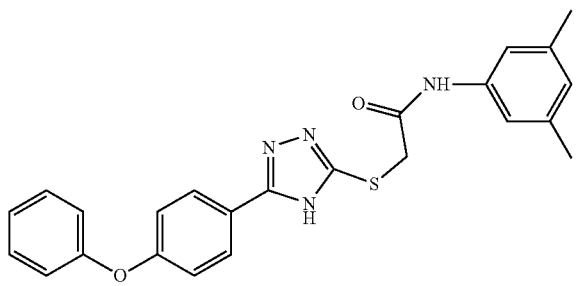 [SMILES: Cc1cc(C)cc(NC(=O)CSc2nnc(-c3ccc(Oc4ccccc4)cc3)[nH]2)c1] |

N-(3,5-Dimethyl-phenyl)-2-[5-(4-phenoxy-phenyl)-4H-[1,2,4]triazol-3-ylsulfanyl]-acetamide. It was prepared using Scheme-2 as white solid. 1H NMR (300 MHz, DMSO-d$_6$) δ 0.90 (t, J = 7.2 Hz, 3H), 1.57-1.65 (m, 2H), 2.22 (s, 6H), 2.58-2.63 (m, 2H), 4.07 (s, 2H), 6.70 (s, 1H), 7.20 (s, 2H), 7.31-7.34 (m, 2H), 7.85-7.88 (m, 2H), 10.14 (s, 1H), 14.33 (br s, 1H).

| | |
|---|---|
| 134 | 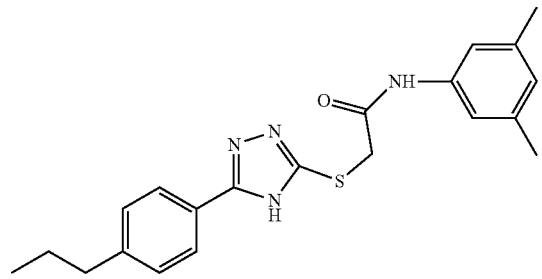 [SMILES: CCCc1ccc(-c2nnc(SCC(=O)Nc3cc(C)cc(C)c3)[nH]2)cc1] |

N-(3,5-Dimethyl-phenyl)-2-[5-(4-propyl-phenyl)-4H-[1,2,4]triazol-3-ylsulfanyl]-acetamide. It was prepared using Scheme-2 as white solid. 1H NMR (300 MHz, DMSO-d$_6$) δ 0.90 (t, J = 7.2 Hz, 3H), 1.57-1.65 (m, 2H), 2.22 (s, 6H), 2.58-2.63 (m, 2H), 4.07 (s, 2H), 6.70 (s, 1H), 7.20 (s, 2H), 7.31-7.34 (m, 2H), 7.85-7.88 (m, 2H), 10.14 (s, 1H), 14.33 (br s, 1H).

| 137 | 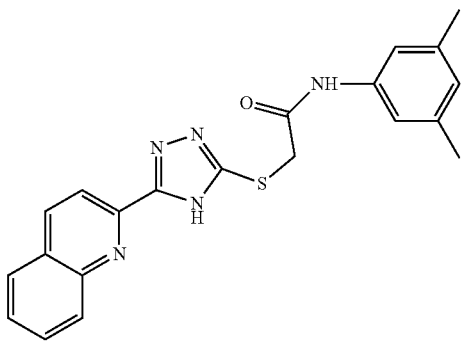 |

N-(3,5-Dimethyl-phenyl)-2-(5-quinolin-2-yl-4H-[1,2,4]triazol-3-ylsulfanyl)-acetamide. It was prepared using Scheme-2 as white solid. 1H NMR (300 MHz, DMSO-$d_6$) δ 2.22 (s, 6H), 4.14 (s, 2H), 6.70 (s, 1H), 7.23 (s, 2H), 7.67-7.72 (m, 1H), 7.84-7.89 (m, 1H), 8.06-8.20 (m, 3H), 8.56 (d, J = 7.8 Hz, 1H), 10.20 (s, 1H), 14.97 (br s, 1H).

| 139 | 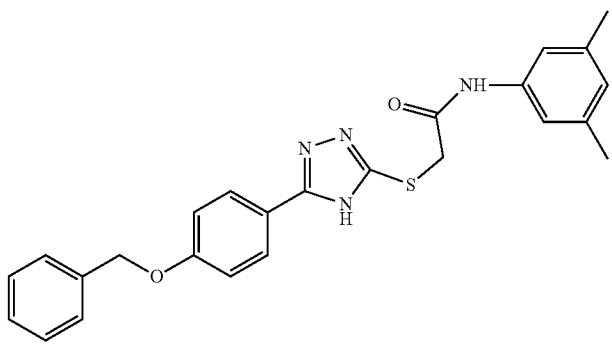 [SMILES: Cc1cc(C)cc(NC(=O)CSc2nnc(-c3ccc(OCc4ccccc4)cc3)[nH]2)c1] |

2-[5-(4-Benzyloxy-phenyl)-4H-[1,2,4]triazol-3-ylsulfanyl]-N-(3,5-dimethyl-phenyl)-acetamide. It was prepared using Scheme-2 as white solid. 1H NMR (300 MHz, DMSO-$d_6$) δ 2.22 (s, 6H), 4.06 (s, 2H), 5.17 (s, 2H), 6.70 (s, 1H), 7.13-7.20 (m, 4H), 7.41-7.46 (m, 5H), 7.88-7.90 (m, 2H), 10.14 (s, 1H), 14.25 (br s, 1H).

| 144 | 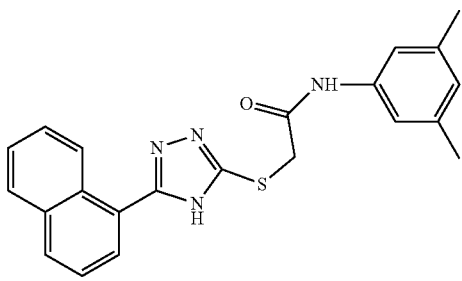 [SMILES: Cc1cc(C)cc(NC(=O)CSc2nnc(-c3cccc4ccccc34)[nH]2)c1] |

N-(3,5-Dimethyl-phenyl)-2-(5-naphthalen-1-yl-4H-[1,2,4]triazol-3-ylsulfanyl)-acetamide. It was prepared using Scheme-2 as white solid. 1H NMR (300 MHz, DMSO-$d_6$) δ 2.22-2.32 (m, 6H), 4.14-4.22 (m, 2H), 6.71-6.78 (m, 1H), 7.22-8.07 (m, 8H), 8.83-9.08 (m, 1H), 10.20-10.28 (m, 1H), 14.52 (br s, 1H).

| 145 | 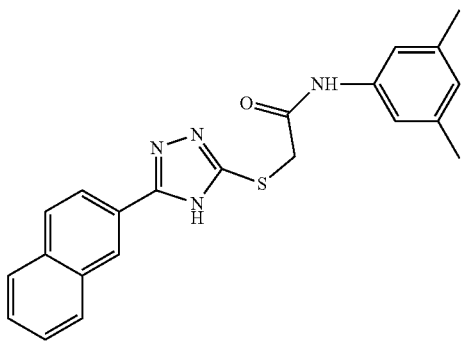 [SMILES: Cc1cc(C)cc(NC(=O)CSc2nnc(-c3ccc4ccccc4c3)[nH]2)c1] |

N-(3,5-Dimethyl-phenyl)-2-(5-naphthalen-2-yl-4H-[1,2,4]triazol-3-ylsulfanyl)-acetamide. It was prepared using Scheme-2 as white solid. 1H NMR (300 MHz, DMSO-$d_6$) δ 2.22 (s, 6H), 4.13 (s, 2H), 6.70 (s, 1H), 7.24 (s, 2H), 7.57-7.60 (m, 2H), 7.96-8.06 (m, 4H), 8.54 (s, 1H), 10.20 (s, 1H), 14.49 (br s, 1H).

146

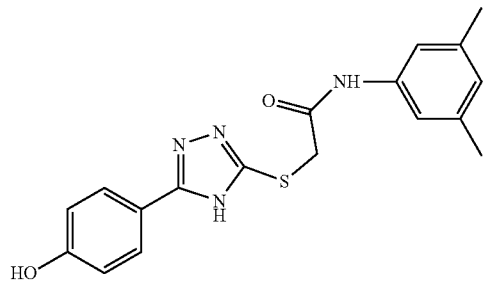 [SMILES: Cc1cc(C)cc(NC(=O)CSc2nnc(-c3ccc(O)cc3)[nH]2)c1]

N-(3,5-Dimethyl-phenyl)-2-[5-(4-hydroxy-phenyl)-4H-[1,2,4]triazol-3-ylsulfanyl]-acetamide. It was prepared using Scheme-2 as white solid. 1H NMR (300 MHz, DMSO-$d_6$) δ 2.22 (s, 6H), 4.02 (s, 2H), 6.69-6.86 (m, 3H), 7.20 (s, 2H), 7.70-7.80 (m, 2H), 10.03-10.12 (m, 2H), 14.18 (br s, 1H).

155

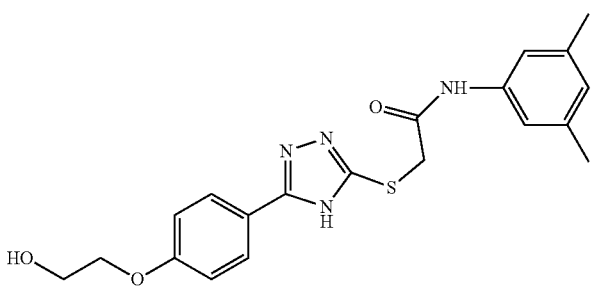 [SMILES: Cc1cc(C)cc(NC(=O)CSc2nnc(-c3ccc(OCCO)cc3)[nH]2)c1]

N-(3,5-Dimethyl-phenyl)-2-{5-[4-(2-hydroxy-ethoxy)-phenyl]-4H-[1,2,4]triazol-3-ylsulfanyl}-acetamide. It was prepared using Scheme-2 as white solid. 1H NMR (300 MHz, DMSO-$d_6$) δ 2.21 (s, 6H), 3.75 (s, 2H), 4.04-4.12 (m, 4H), 6.70-6.87 (m, 3H), 7.18 (s, 2H), 7.60-7.78 (m, 2H), 10.18 (s, 1H), 14.14 (br s, 1H).

166

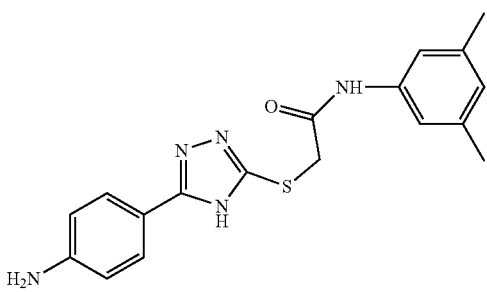

2-[5-(4-Amino-phenyl)-4H-[1,2,4]triazol-3-ylsulfanyl]-N-(3,5-dimethyl-phenyl)-acetamide. It was prepared using Scheme-2 as off-White solid; 1H NMR (300 MHz, DMSO-$d_6$) δ 2.22 (s, 6H), 4.07 (s, 2H), 5.63 (br s, 2H), 6.60-6.70 (m, 3H), 7.20 (s, 2H), 7.60-7.62 (m, 2H), 10.13 (s, 1H), 13.93 (br s, 1H).

168

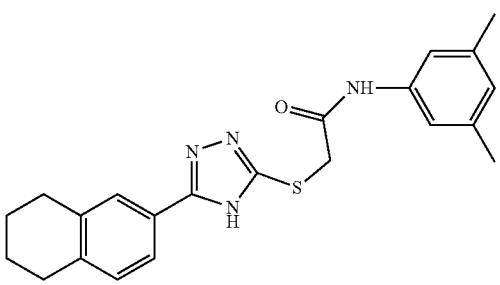 [SMILES: Cc1cc(C)cc(NC(=O)CSc2nnc(-c3ccc4c(c3)CCCC4)[nH]2)c1]

N-(3,5-Dimethyl-phenyl)-2-[5-(5,6,7,8-tetrahydro-naphthalen-2-yl)-4H-[1,2,4]triazol-3-ylsulfanyl]-acetamide. It was prepared using Scheme-2 as white solid. 1H NMR (300 MHz, DMSO-$d_6$) δ 1.76 (s, 4H), 2.22 (s, 6H), 2.75 (s, 4H), 4.07 (s, 2H), 6.70 (s, 1H), 7.21 (s, 3H), 7.67 (s, 2H), 10.15 (s, 1H), 14.29 (br s, 1H).

Example 3

The IC$_{50}$ of the 16 compounds according to Table 1 were determined according to the Cell Growth Inhibition method and are shown in Table 4 below.

TABLE 4

| Compound Label | HeLa Cells IC$_{50}$ (µM) | Jurkat Cells IC$_{50}$ (µM) |
|---|---|---|
| A | >25 | >10 |
| B | >25 | >10 |
| C | 15.2 | >10 |
| D | >25 | >10 |
| E | >25 | >10 |
| F | 12.6 | 9.8 |
| G | >25 | >10 |
| H | >25 | >10 |
| I | >25 | >10 |
| J | >25 | >10 |
| K | >25 | >10 |
| L | >25 | >10 |
| M | >25 | >10 |
| N | 4.2 | 5.4 |
| O | >25 | >10 |
| P | 18.3 | >10 |

Figure 1B:
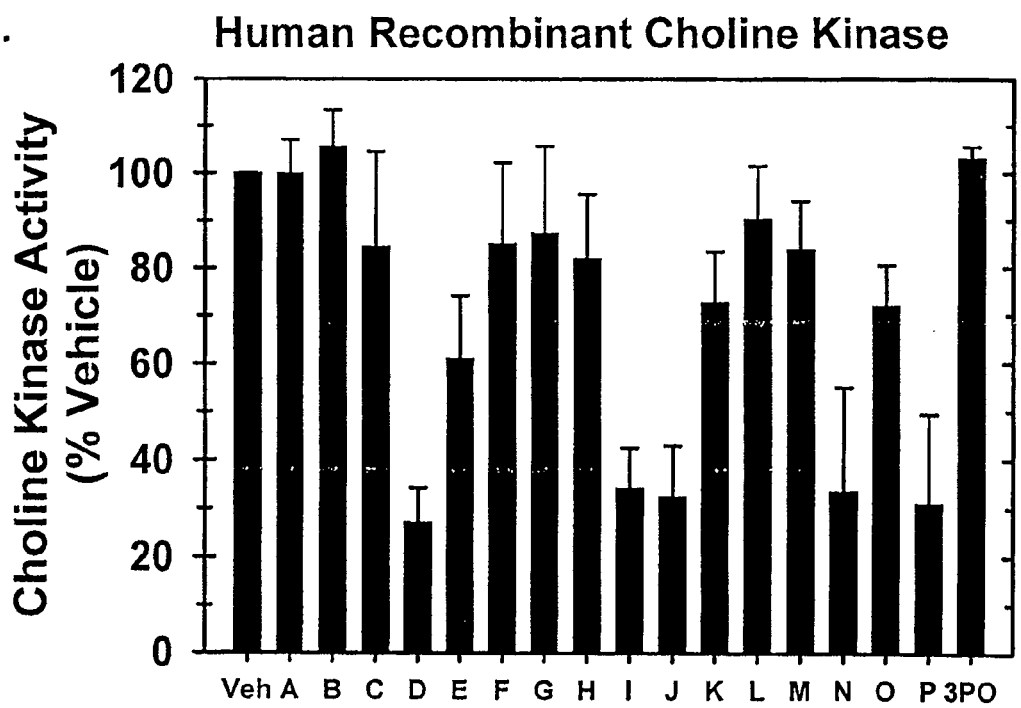
FIG. 1B. Choline kinase activity assays using human recombinant choline kinase were performed as described in the Choline Kinase Activity method. Activity assays were done in the presence of 100 µM of each compound. Data are represented as % of control activity for each compound. Mean±STD from two independent experiments. $p<0.05$.
Figure 1C:
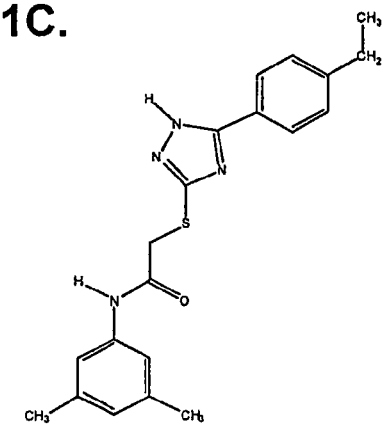
FIG. 1C. Molecular structure of CK37.
Figure 1D:
FIG. 1D. Secondary structure of choline kinase with CK37 (rod) depicted within the active site of the protein.

As shown in FIG. 1A, two compounds significantly inhibited choline kinase activity of Hela lysates. FIG. 1B shows that several compounds significantly inhibited human recombinant choline kinase activity. CK37 (FIG. 1C) exhibited the greatest suppression of all compounds tested (30.8%±2.7%), and FIG. 1D illustrates its potential interaction with the active site within choline kinase.

Example 4

CK37 Effects on Endogenous Choline Kinase Activity

Figure 2A:
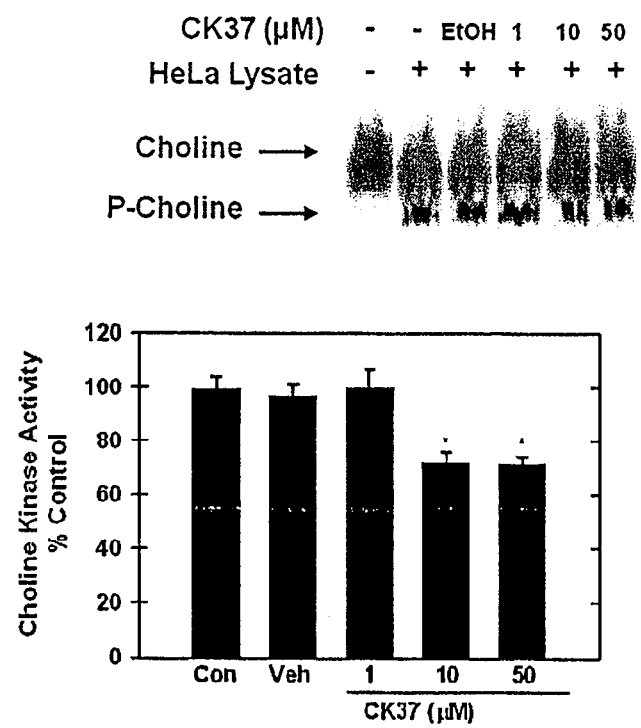
FIG. 2. Effect of CK37 on choline kinase activity assays in whole cells FIG. 2A. CK37 results in a dose-dependent decrease in endogenous choline kinase activity. Activity assays were performed as described in the Choline Kinase Activity method. Representative thin layer chromatography plate examining choline and phosphocholine levels with increasing concentrations of CK37. Data are represented as % of control activity for each CK37 concentration. Mean±STD of three independent experiments. $p<0.05$.
FIG. 2B. CK37 results in a dose-dependent decrease in endogenous choline kinase activity. Activity assays in whole cells were performed as described in the Choline Kinase Activity method. Representative thin layer chromatography plate examining choline and phosphocholine levels with increasing concentrations of CK37. Data are represented as % of control activity and mean±STD of three independent experiments. $p<0.01$.
FIG. 2C. CK37 results in a dose-dependent decrease in recombinant choline kinase activity. Activity assays were performed as described in the Choline Kinase Activity method. Representative thin layer chromatography plate examining choline and phosphocholine levels with increasing concentrations of CK37. Data are represented as % of control activity for each CK37 concentration. Mean±STD of three independent experiments. $p<0.05$.
FIG. 2D. NMR measurements of choline metabolites, including phosphocholine, as described in the NMR Measurements of Choline Metabolites method. Data are represented as % of relative to time zero for each CK37 concentration. Mean±STD of three independent experiments. $p<0.05$.
Figure 2B:
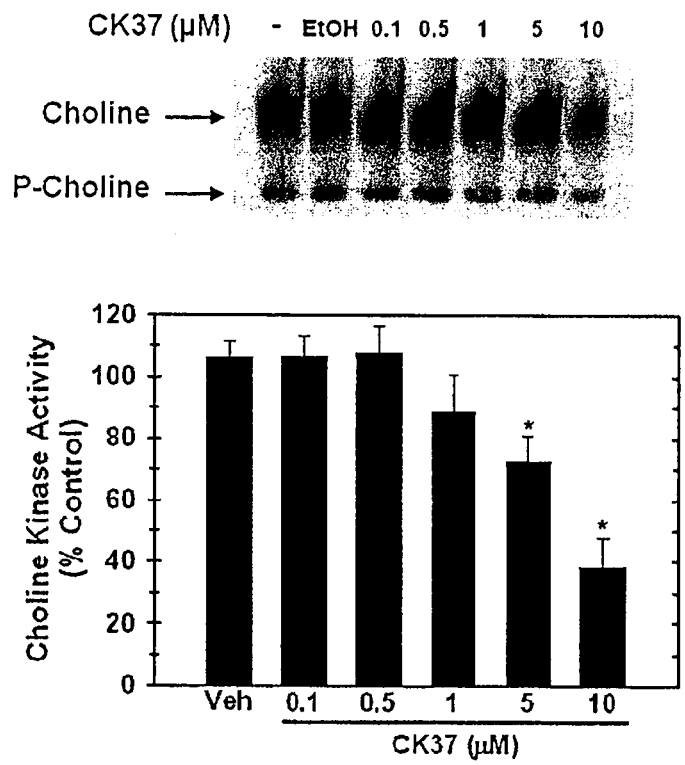
Figure 2C:
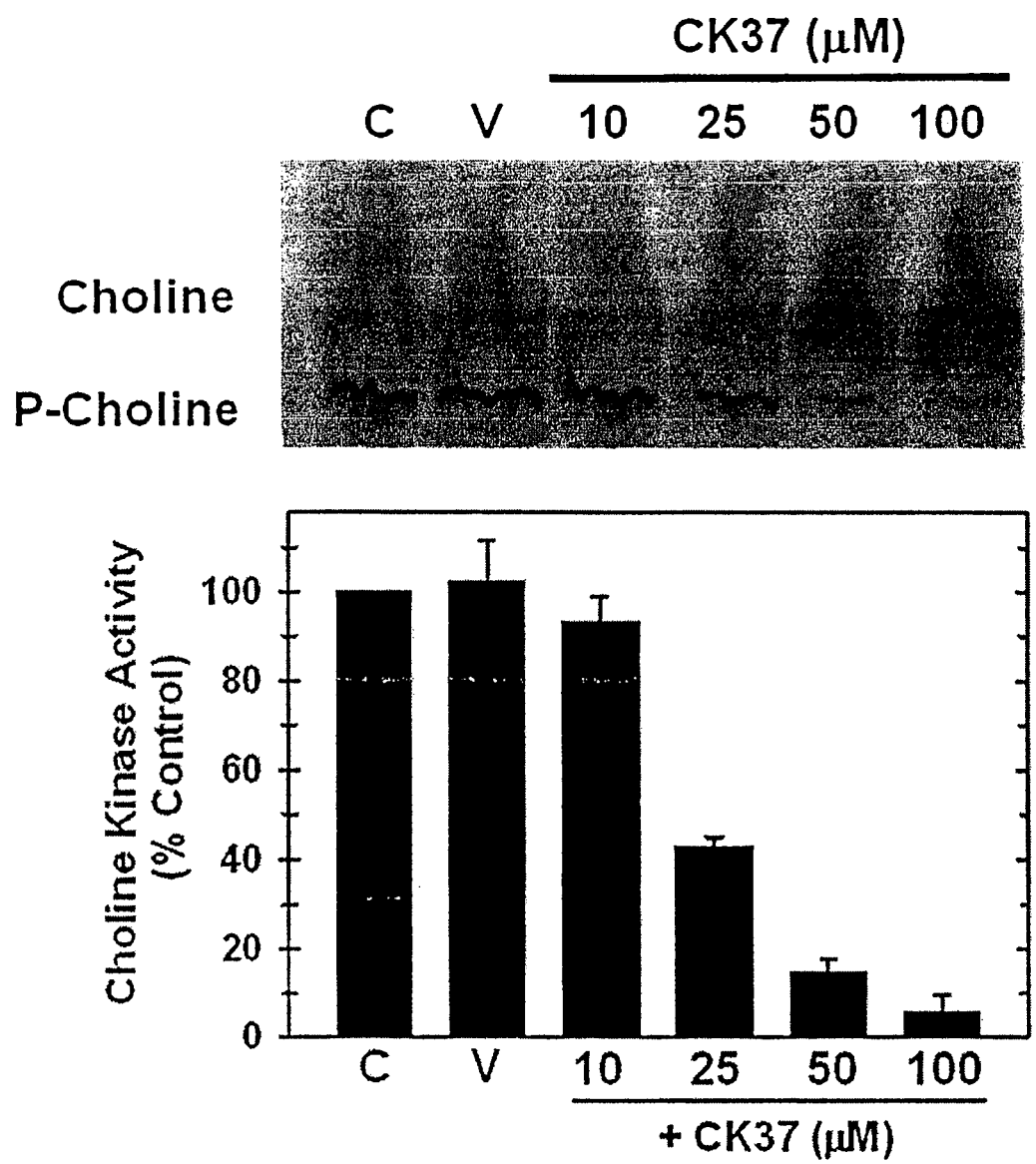
Figure 2D:
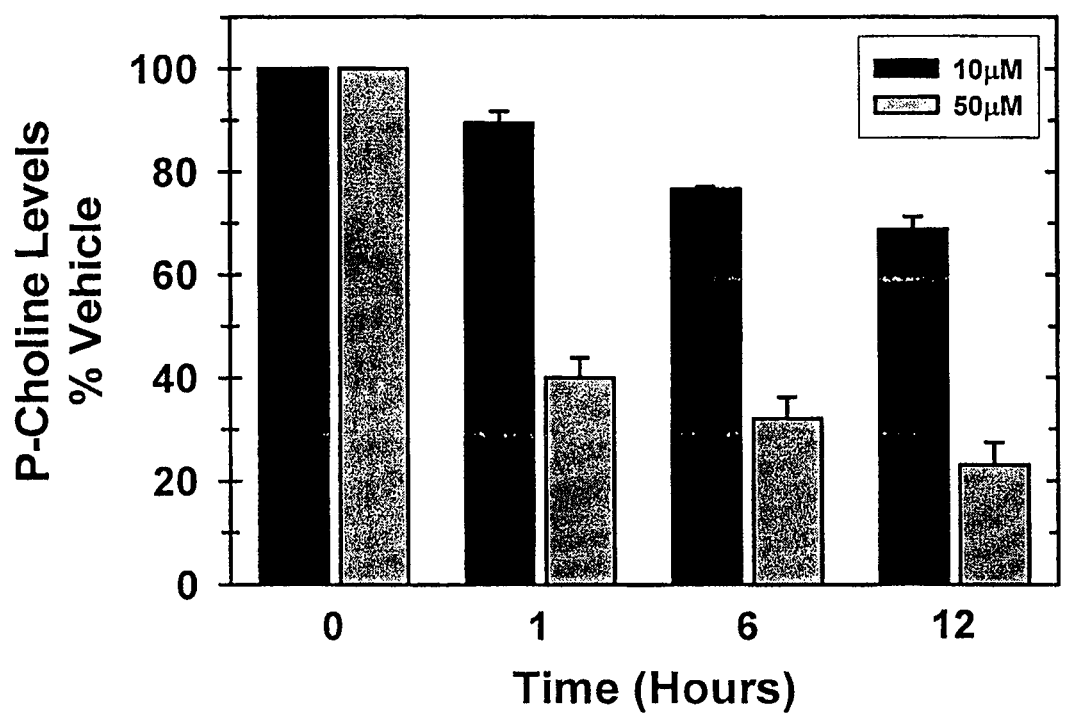

Kinase assays were performed on HeLa cell lysates for the exemplary compound set forth as "N" in Table 1 and referred to herein as CK37. Addition of CK37 resulted in a dose-dependent decrease in choline kinase activity between 1 and 10 µM (FIG. 2A, 28.2%±5.8%). We did not observe any further significant decrease in activity at higher concentrations up to 50 µM under these ex vivo conditions. To investigate CK37's ability to suppress choline kinase activity in whole cells, HeLa cells were incubated with increasing concentrations of CK37 in the presence of radiolabeled choline. As shown in FIG. 2B, CK37 inhibited endogenous choline kinase activity at 1 µM and had the greatest effect at 10 µM (61.7%±9.7%). Endogenous choline was suppressed in the presence of CK37, suggesting a possible loss of choline uptake due to a decrease in choline flux through choline kinase. FIG. 2C shows that CK37 inhibited recombinant choline kinase activity. FIG. 2D quantitates the inhibition at 10 µM and 50 µM CK37 using analysis of 1H NMR measurements.

Example 5

CK37 Cytostatic and Cytotoxic Properties

Figure 3A:
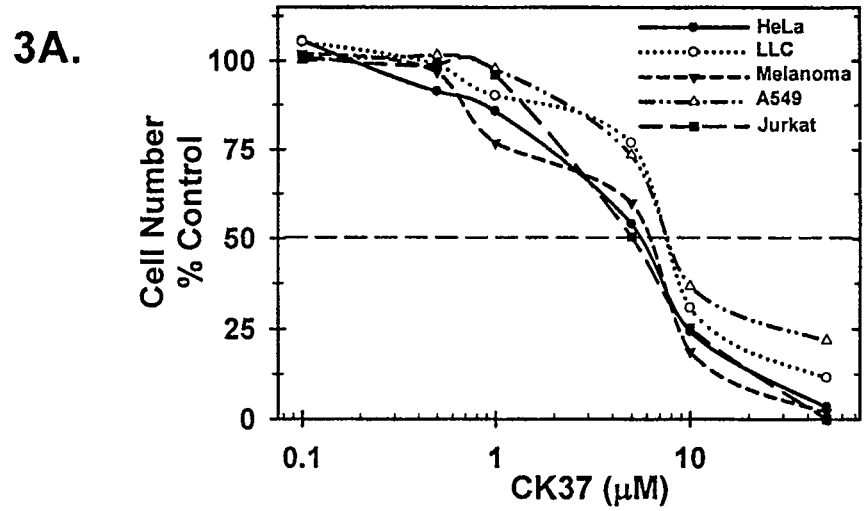
FIG. 3A. Cell proliferation assays were performed as described in the Cell Growth Inhibition method. Data are represented as % of cell growth of vehicle control as log 10 of CK37 from duplicate values from three independent experiments.

To investigate the effects of CK37 on tumor cell growth, we utilized various neoplastic cell lines from both solid and hematologic origins and found that incubation with CK37 caused a dose-dependent suppression of cell growth on all tumor cell lines investigated (FIG. 3A; IC$_{50}$ values: 5-10 µM).

Figure 3B:
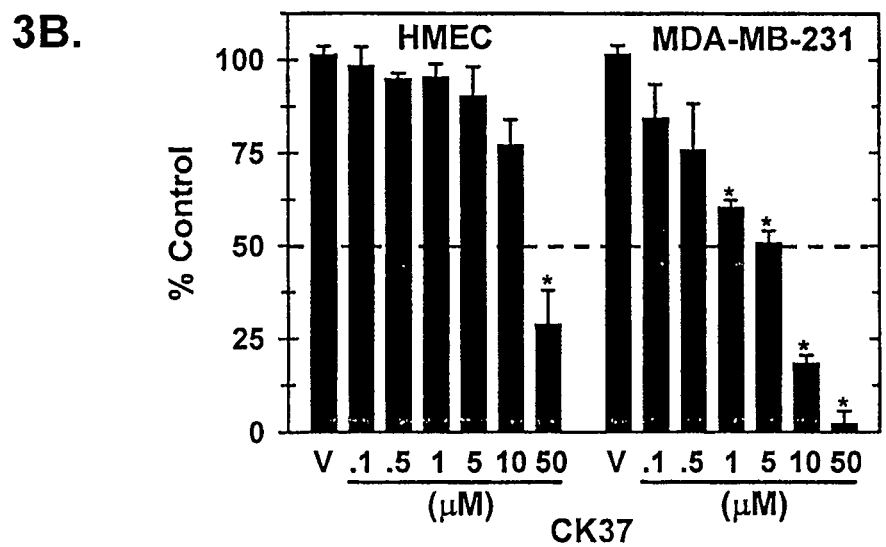
FIG. 3B. Cell proliferation assays were performed as described in the Cell Growth Inhibition method. Data are represented as % of cell growth of vehicle control for each concentration of CK37 from duplicate values from three independent experiments.

Selective inhibition for tumor cells versus normal primary cells can be helpful for the development of successful antineoplastic agents. To investigate CK37's potential for therapeutic selectivity, we incubated primary mammary epithelial cells (HMEC: Lonza) and tumorigenic MDA-MB-231 (ATCC: HTP-26) mammary carcinoma cells with several concentrations of CK37. As observed in FIG. 3B, CK37 exhibited a 20-fold difference in selectivity against neoplastic versus primary cell growth (e.g., 10 µM HMEC vs. 0.5 µM MDA-MB-231).

Choline kinase inhibition in the ex vivo versus whole cell experiments and the absence of dose limiting toxicities suggests that CK37's anti-proliferative effect may be due to its direct suppression of choline kinase and not through effects on choline transport.

Figure 3C:
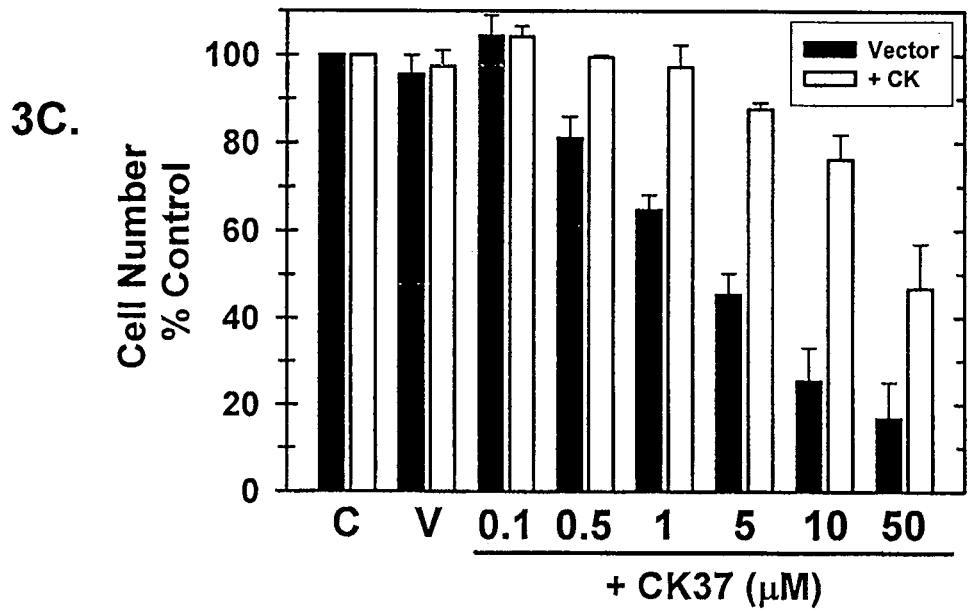
FIG. 3C. Cell proliferation is shown for Hela cells that were modified to overexpress wild type choline kinase. HeLa cells were transiently transfected with either empty vector or vector containing wild type choline kinase twenty-four hours prior to addition of increasing concentrations of CK37. Choline kinase overexpression was confirmed by Western blot. Cell proliferation assays were performed as described in the Cell Growth Inhibition method. Data are represented as % of cell growth of vehicle control for each concentration of CK37 from duplicate values from three independent experiments. Black bars in the figure are data from transient transfection of the empty vector.
Figure 3D:
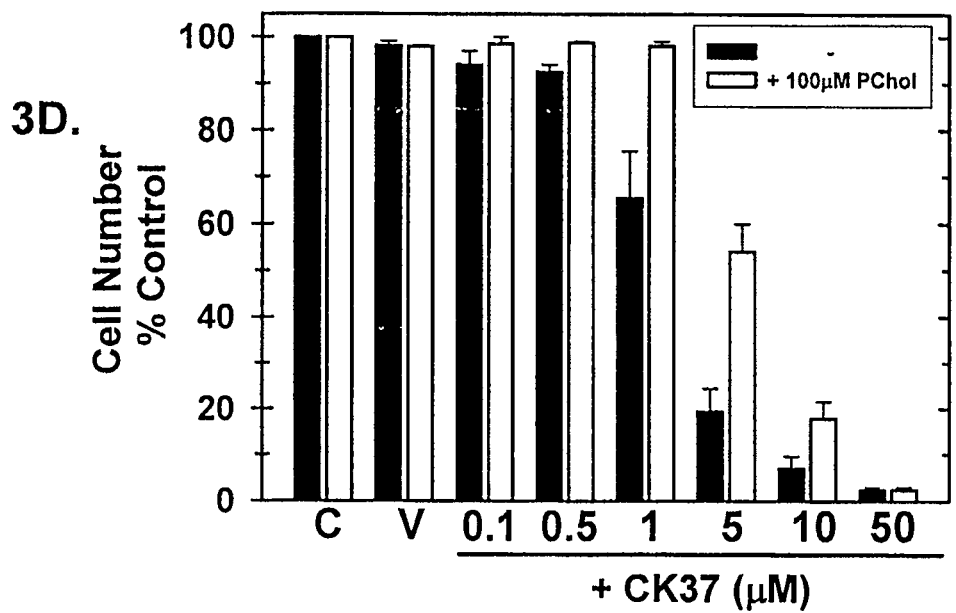
FIG. 3D. HeLa cell proliferation assays were performed in the absence or presence of 100 µM phosphocholine. Cell proliferation assays were performed as described in the Cell Growth Inhibition method. Data are represented as % of cell growth of vehicle control for each concentration of CK37 from duplicate values from three independent experiments. Black bars in the figure are data collected in the absence of the phosphocholine addition to the medium.

FIGS. 3C and 3D are also cell proliferation assays, but are performed with Hela cells that overexpress wild type choline kinase and with Hela cells in the presence of phosphocholine, respectively. These experiments appear to show on-target specific effects of CK37 against endogenous choline kinase (e.g., that CK37 is targeting endogenous choline kinase directly and not via an upstream or downstream effector/regulator). The increased choline kinase expression (FIG. 3C) and added phosphocholine (FIG. 3D) both show resistance to CK37's anti-proliferative effects; this suggests that CK37 has on-target specific effects on endogenous choline kinase.

Figure 3E:
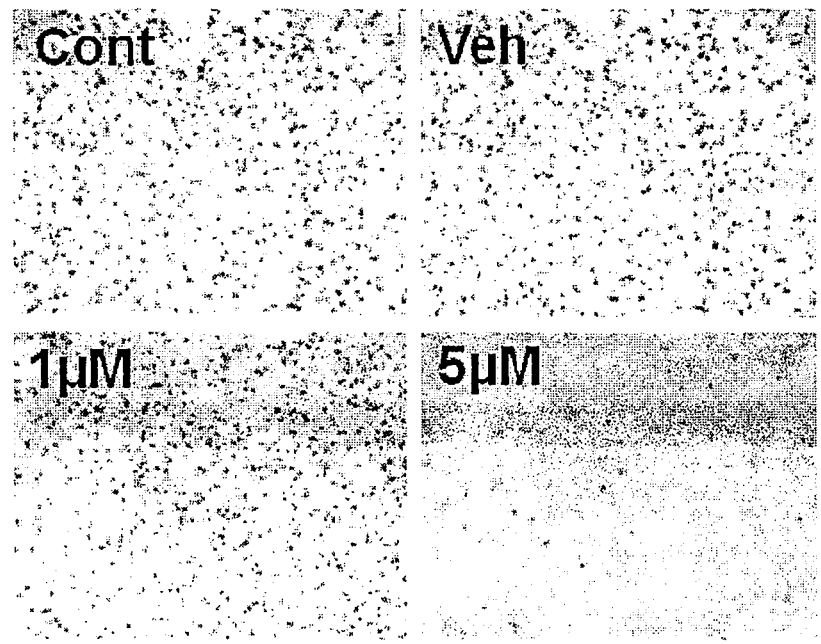
FIG. 3E. Soft agar colony formation assays were performed as described in the methods. Representative images of soft agar colony formation from control, vehicle, 1 µM, and 5 µM CK37. Data are represented as the number of colonies from duplicate measurements from two independent experiments. p<0.01.
Figure 3E:
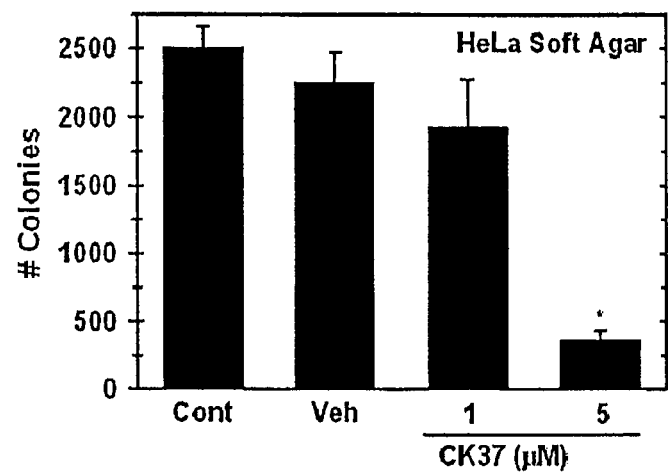

Anchorage-independent growth can be an indicator for tumorigenicity of neoplastic cells. We investigated the ability of CK37 to suppress HeLa anchorage independent growth by measuring soft agar colony formation. As evident in FIG. 3E, CK37 efficiently blocked HeLa soft agar colony formation at 5 µM (Control: 2506±158 vs. 5 µM CK37: 360±77). The concentration of CK37 to suppress soft agar colony formation was lower than that required for decreased cell proliferation. This may be due to the fact that choline metabolites directly potentiate the Ras signaling pathway, which can be helpful for anchorage-independent growth as tumors. This suggests that choline kinase inhibition is least partially partially selective for anchorage-independent growth of tumor cells.

Example 6

Effects of CK37 on MAPK/ERK Signaling, Cytoskeleton Arrangement, and Membrane Structure Phosphatidic acid is a downstream product of the Kennedy pathway, which can be initiated by the phosphorylation of choline by choline kinase. Phosphatidic acid can be helpful for the recruitment of a specific Ras guanine-nucleotide exchange factor, SOS, as well as Raf-1, to the plasma membrane. Therefore, we sought to determine if CK37 disrupts signaling through the MAPK pathway. As shown in FIG. 4A, 10 µM CK37 decreased the phosphorylation of ERK1/2, whereas total ERK1/2 levels remained unchanged. Thus, CK37 disrupted ERK1/2 phosphorylation, a downstream signaler of Ras.

Figure 4C:
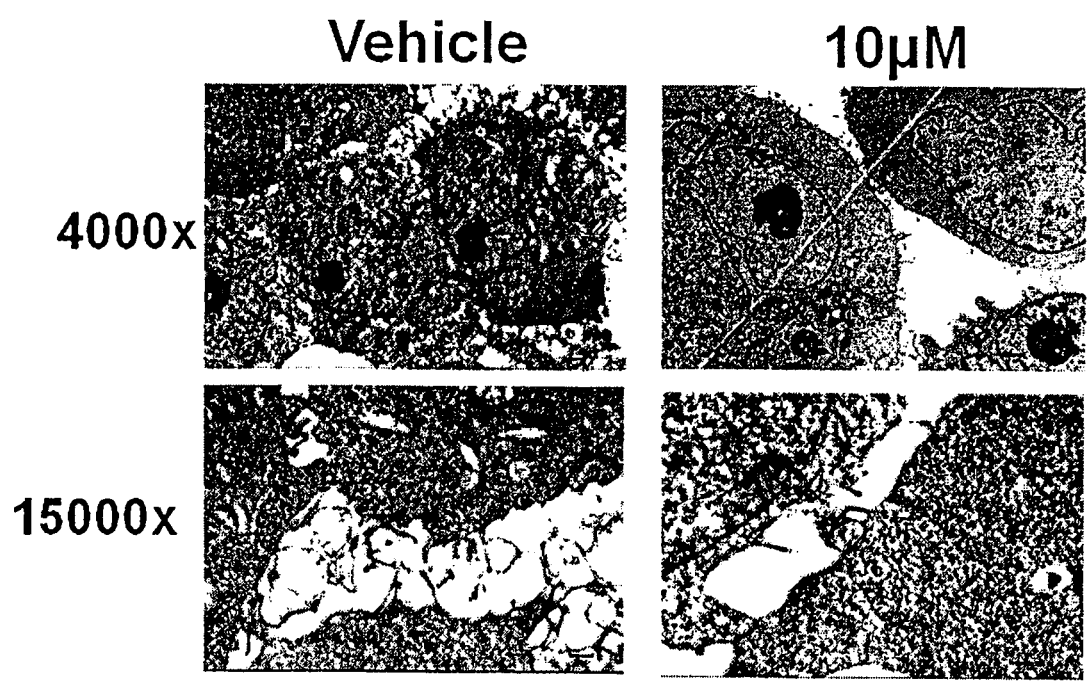
FIG. 4C. Electron microscopy was performed as described in the methods. MDA-MB-231 cell images at 4000× and 15000× magnification from vehicle or 10 µM CK37 treated samples.

Phosphatidic acid can sometimes stimulate actin polymerization, and these actin stress fibers can result in prolonged MEK activation. To investigate cytoskeletal arrangement in response to CK37 treatment, we performed immunofluorescence microscopy on HeLa cells using the small molecule phalloidin, which specifically binds to polymerized F-actin, and an antibody for the focal adhesion protein vinculin. Our results demonstrate that in the absence of CK37, HeLa cells show polymerization of F-actin which is directly anchored to the membrane at vinculin containing focal adhesion points. However, incubation with CK37 disrupted the localization of focal adhesion points as well as the appearance of stress fibers (FIG. 4B). CK37 altered the cellular cytoskeleton arrangement and another downstream product of phosphocholine, phosphatidylcholine. Because phosphatidylcholine is a major component of the lipid bilayer, we investigated the effects of CK37 on the plasma membrane. Electron microscopy revealed substantial membrane extensions in both HeLa (FIG. 4C) and MDA-MB-231 cells (data not shown). However, incubation with 10 µM CK37 attenuated these structures, as evident in FIG. 4C. Thus, CK37 treatment resulted in a loss of cytoskeletal arrangement and decreased membrane extensions, which provide another potential explanation for the loss of mitogenic signaling in response to choline kinase inhibition and loss of choline metabolites.

Phosphatidic acid appears to play a dual role in promoting Ras signaling in neoplastic cells by recruiting the Ras specific guanine-exchange factor, Sos, to the membrane and by promoting the formation of polymerized actin stress fibers necessary for prolonged MEK activation. Accordingly, it may be possible that CK37 mediated inhibition of choline kinase results in decreased choline metabolism leading to disruption of Ras signaling by affecting one or both of these mechanisms, and perhaps in conjunction with modulation of other mechanisms.

Example 7

In Vivo Tumor Growth Effects of CK37

Figure 5A:
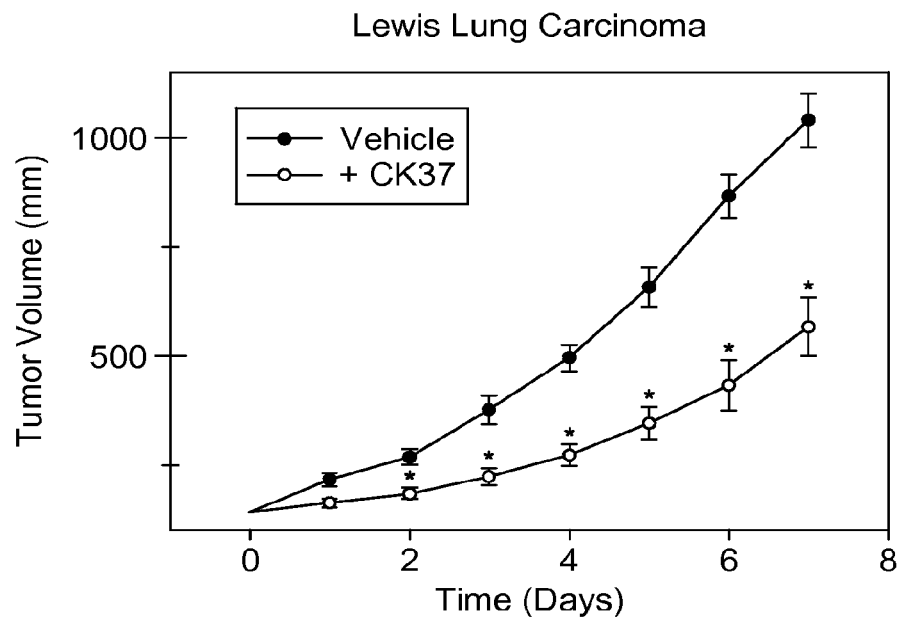
FIG. 5A. In vivo tumor growth assays were performed as described in the Mouse Tumor method. Tumors were measured daily using blunt-end Vernier calipers, and mice with established tumors were blindly randomized into either Vehicle (filled circles) or CK37 treatment (open circles) groups. Mice were administered daily intraperitoneal doses of either 50 µL DMSO (n=10) or 0.08 mg/g of CK37 (n=10) in 50 µL DMSO at the indicated time points. Data are presented as mean±STD. A significant p<0.01 was obtained at day 2 of administration.
Figure 5B:
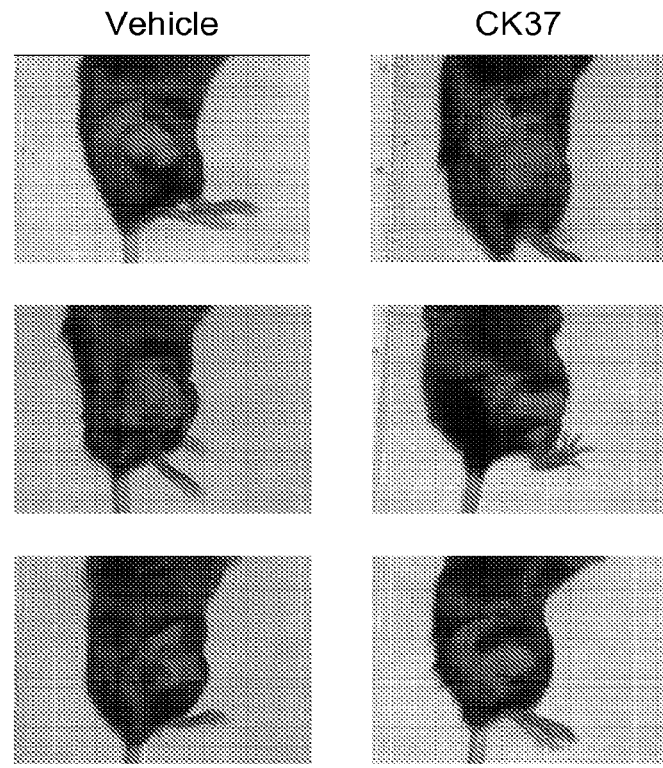
FIG. 5B. Representative tumor images from both vehicle and CK37 treated groups.
Figure 6:
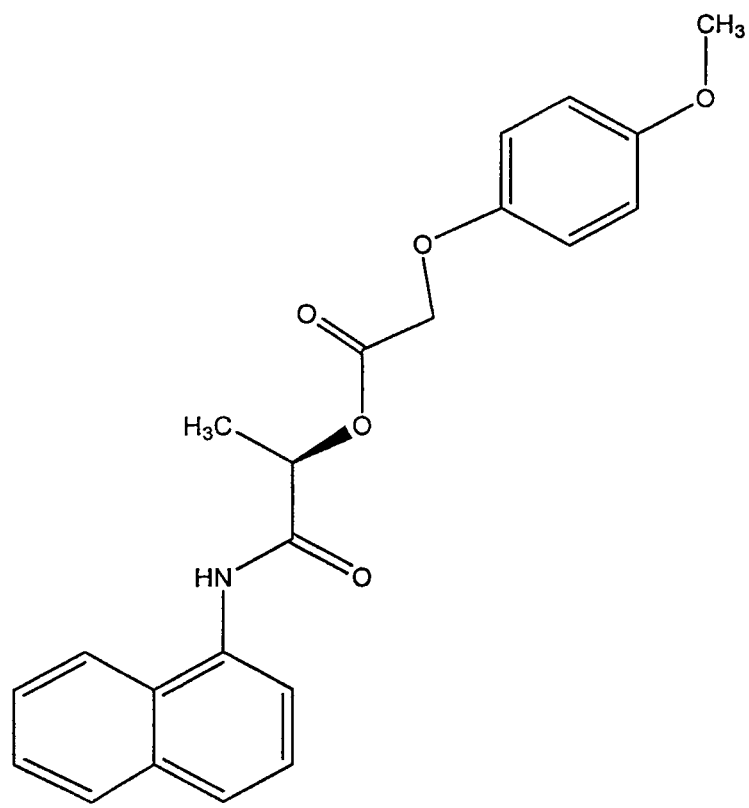
FIG. 6. Molecular structure of CP6.
Figure 7:
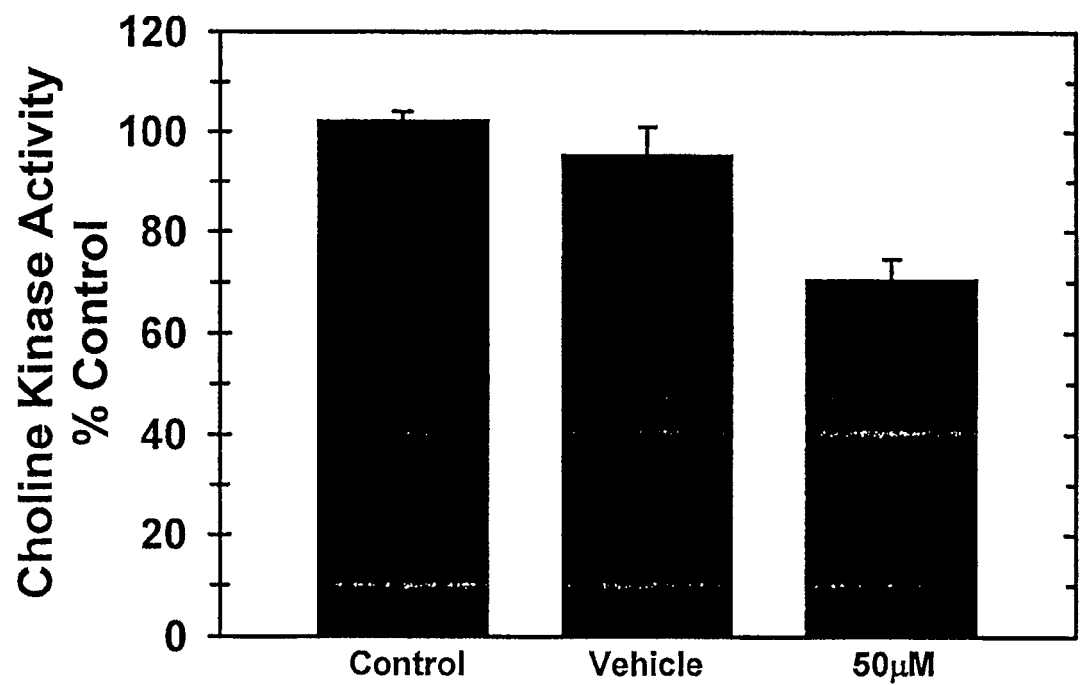
FIG. 7. CP6 results in a dose-dependent decrease in endogenous choline kinase activity. Activity assays were performed as described in the Choline Kinase Activity method using HeLa cell lysate. Data are represented as % of control activity for each CP6 concentration. Mean±STD of three independent experiments. p<0.05.
Figure 8:
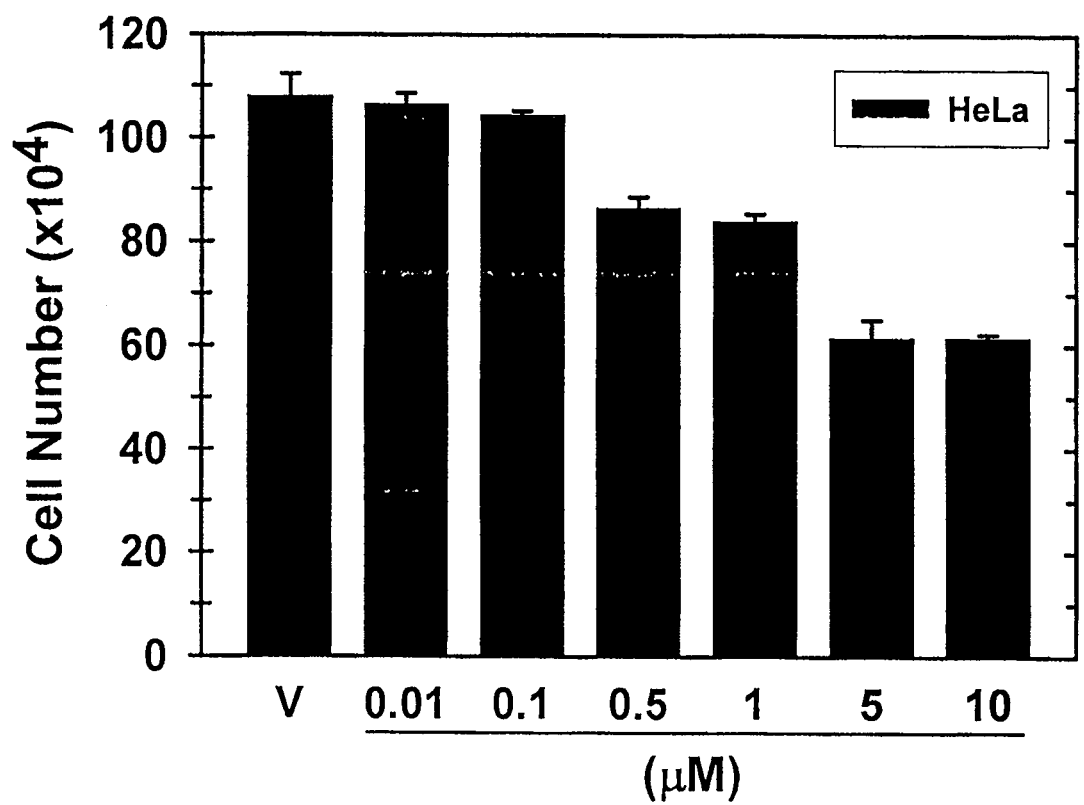
FIG. 8. CP6 selectively suppresses HeLa cell proliferation. Cell proliferation assays of Hela Cells were performed as described in the Cell Growth Inhibition method. Data are represented as % of cell growth of vehicle control for each concentration of CP6 from duplicate values from three independent experiments.
Figure 9:
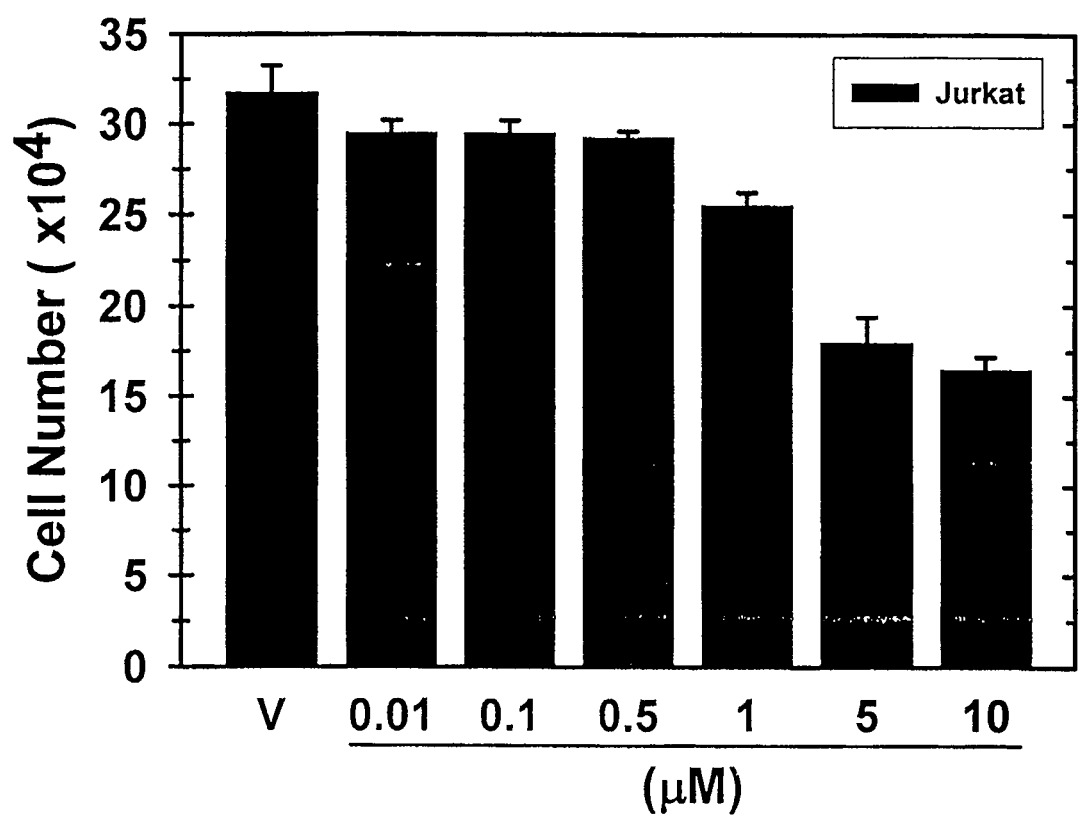
FIG. 9. CP6 selectively suppresses Jurkat cell proliferation. Cell proliferation assays of Jurkat Cells were performed as described in the Cell Growth Inhibition method. Data are represented as % of cell growth of vehicle control for each concentration of CP6 from duplicate values from three independent experiments.

In order to investigate some possible non-toxic doses of CK37 for use in vivo, we intraperitoneally injected C57B1/6 mice with 0.06, 0.07, and 0.08 mg/g of CK37. We observed no clinical signs or symptoms of distress at any of the three doses. C57B1/6 mice bearing Lewis Lung Carcinoma xenografts (mean baseline mass=143±14 mg) were given intraperitoneal injections of 0.08 mg/g CK37 daily for nine days. As shown in FIG. 5A-B, CK37 administration suppressed tumor growth by 48% compared to the vehicle control group. At the end of treatment, the wet weight of resected tumors from the CK37 group was found to be significantly less than that of the vehicle control group (CK37: 648±96 mg; Vehicle: 1109±107 mg, p<0.01).

Example 8

Comparison of CK37 with Choline Analogs

Several small molecule inhibitors of choline kinase have been synthesized and investigated for their potential anti-tumor benefits. These compounds appear to be initially designed from the choline analog, HC-3. One such derivative, designated MN58B, has been reported to suppress choline kinase and tumor growth in several xenograft mouse models with an $IC_{50}$ of 4.2 µM for choline kinase activity and an $IC_{50}$ of 0.5 µM for HT-29 human adenocarcinoma cells. In addition, MN58B reportedly caused a 75% inhibition in HeLa cell endogenous choline kinase. In our experiments that had somewhat different conditions, CK37 resulted in a 60% decrease at the about the same concentration. Also, MN58B was shown to have a dose limiting toxicity between 5-10 mg/kg, whereas CK37 did not demonstrate a dose limiting toxicity even at 80 mg/kg. Thus, CK37 exhibits at least comparable effects on choline kinase inhibition and in vivo anti-tumor growth without the toxicities observed with HC-3 derivatives.

Example 9

Illustration of in vitro anti-cancer properties exhibited by compound according to the invention.

The ability of the compounds listed in Tables 2 and 3 to inhibit the proliferation of cancer cells was investigated in five different cell lines. The results are set forth in Table 5 and demonstrate that many of the listed compound in accordance with the invention inhibit tumor cell proliferation at low micromolar concentrations and thus have good in vitro anti-cancer properties.

These cancer cell lines included K562, MDA-MB-231, U937, NCI-H82, and Calu-6. These cell lines were cultured in accordance with conditions set forth in General Methodologies. Inhibition of cell proliferation was ascertained using the MTT assay. Briefly, the tretazolium salt, 3-(4,5-dimethylthiazolyl-2)-2,5 diphenyhetrazolium bromide is reduced by metabolically active cells (producing reductive species such as NADH and NADPH). Upon reduction, MTT turns purple and the spectrophometric determination of the absorbance is proportional to the number of living and proliferating cells. The assay is used to determine cell death and thus inhibition of cell proliferation.

The five cell lines used to determine the ability of the compounds of the invention to inhibit cancer cell proliferation are well known by persons of ordinary skill in the art and include K562, a chronic myelogenous leukemia cell line, MDA-MB-231, a breast adenocarcinoma cancer cell line, U937, a lymphoma cell line, NCI-H82, a small cell lung carcinoma cell line, and Calu-6, a lung carcinoma.

Results show that many of the listed compounds inhibit cancer cell proliferation at low micromolar concentrations indicating that these compounds have good in vitro anti cancer properties.

What is claimed:

1. A method of treating a subject suffering from a disorder or disease characterized by neoplastic cell proliferation, the method comprising administering to the subject a therapeutically effective amount of a choline kinase (ChoK) inhibitor, wherein the disease or disorder is selected from breast cancer, colon cancer, lung cancer, cervical cancer, melanoma, lymphoma, leukemia, colorectal cancer, pancreatic cancer, and ovarian cancer, and the ChoK inhibitor is selected from

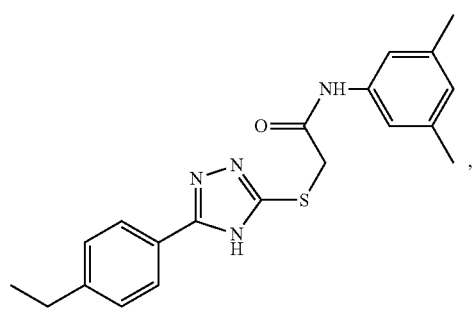

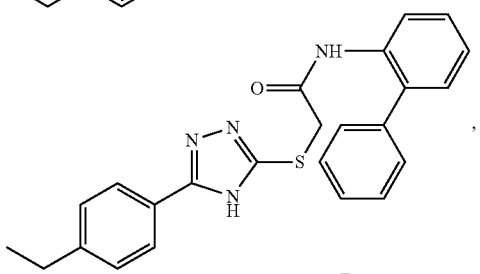

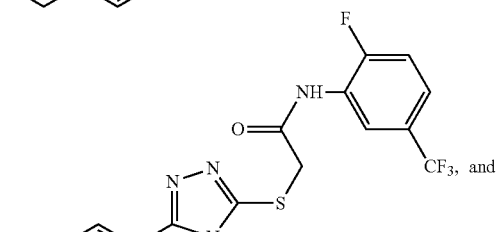

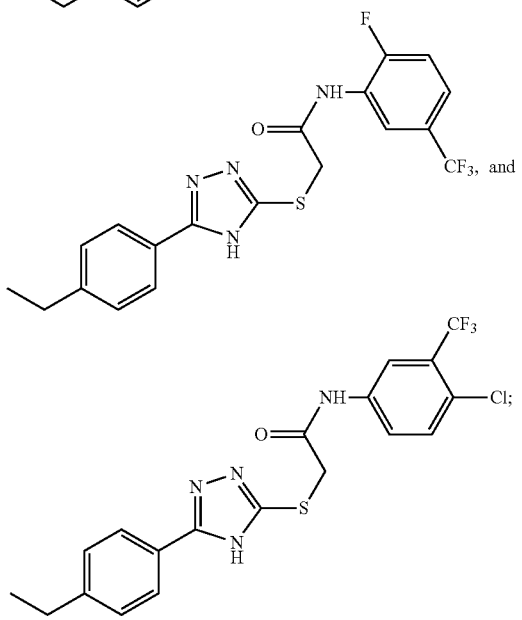

and the isomers, tautomers, and pharmaceutically acceptable salts thereof.

2. The method according to claim 1, wherein the disease comprises tumor cell proliferation.

3. The method according to claim 2, wherein the tumor is a lung, breast, colorectal, pancreatic, cervical or ovarian tumor.

4. The method according to claim 1, wherein the compound directly inhibits ChoK by interacting with a phosphocholine binding pocket of ChoK.

5. The method according to claim 1, wherein the ChoK inhibitor is selected from the group consisting of:

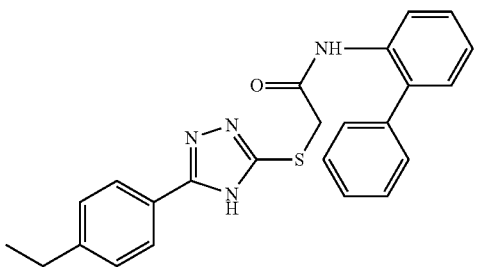 [SMILES: CCc1ccc(-c2nnc(SCC(=O)Nc3ccccc3-c3ccccc3)[nH]2)cc1]

mixtures thereof.

6. The method according to claim 2, wherein administering comprises employing a drug delivery technology capable of delivering the ChoK inhibitor to the tumor.

7. The method according to claim 1, wherein the ChoK inhibitor is administered in a dose effective to suppress cell proliferation in the substantial absence of toxic side effects.

8. The method according to claim 7, wherein the ChoK inhibitor is selected from N-(3,5-dimethylphenyl)-2-[[5-(4-ethylphenyl)-1H-1,2,4-triazol-3-yl]sulfanyl]acetamide; N-(3,5-dimethylphenyl)-2-[[5-(4-ethylphenyl)-2H-1,2,4-triazol-3-yl]sulfanyl]acetamide; N-(3,5-dimethylphenyl)-2-[[5-(4-ethylphenyl)-4H-1,2,4-triazol-3-yl]sulfanyl]acetamide; and mixtures thereof.

9. The method according to claim 1, wherein the ChoK inhibitor is selected from and the isomers, tautomers, and pharmaceutically acceptable salts thereof.

10. The method according to claim 1, wherein the ChoK inhibitor is selected from

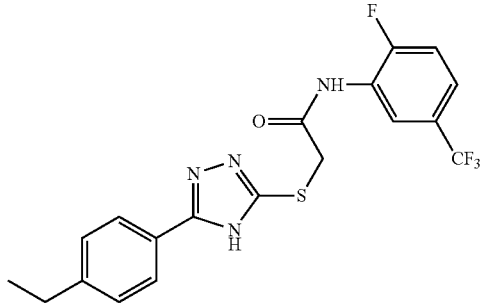 [SMILES: CCc1ccc(-c2nnc(SCC(=O)Nc3cc(C(F)(F)F)ccc3F)[nH]2)cc1]

and the isomers, tautomers, and pharmaceutically acceptable salts thereof.

11. The method according to claim 1, wherein the ChoK inhibitor is selected from

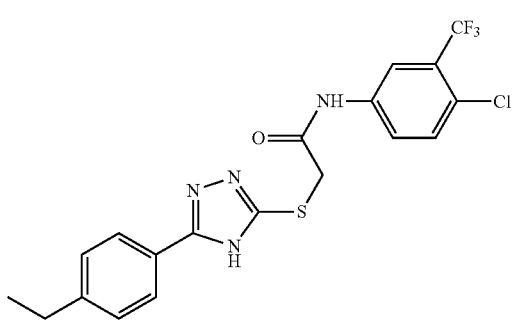 [SMILES: CCc1ccc(-c2nnc(SCC(=O)Nc3ccc(Cl)c(C(F)(F)F)c3)[nH]2)cc1]

and the isomers, tautomers, and pharmaceutically acceptable salts thereof.

12. The method according to claim 1, wherein the disease comprises tumor cell proliferation and the tumor is a lung, breast, colorectal, pancreatic, cervical or ovarian tumor, and the ChoK inhibitor is selected from

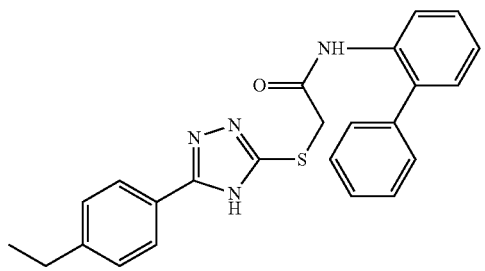 [SMILES: CCc1ccc(-c2nnc(SCC(=O)Nc3ccccc3-c3ccccc3)[nH]2)cc1]

and the isomers, tautomers, and pharmaceutically acceptable salts thereof.

13. The method according to claim 1, wherein the disease comprises tumor cell proliferation and the tumor is a lung, breast, colorectal, pancreatic, cervical or ovarian tumor, and the ChoK inhibitor is selected from

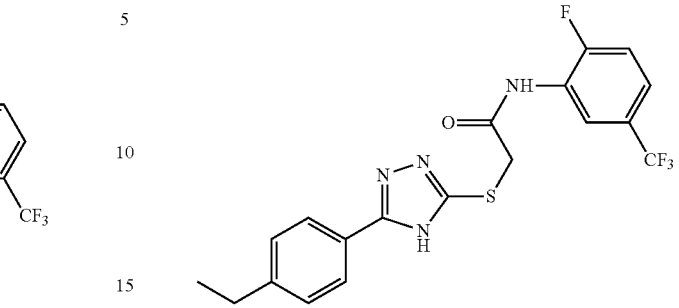

and the isomers, tautomers, and pharmaceutically acceptable salts thereof.

14. The method according to claim 1, wherein the disease comprises tumor cell proliferation and the tumor is a lung, breast, colorectal, pancreatic, cervical or ovarian tumor, and the ChoK inhibitor is selected from

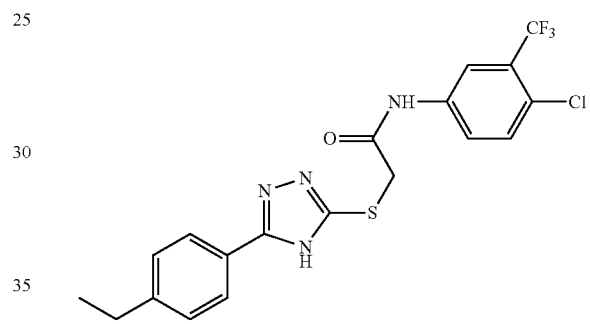

and the isomers, tautomers, and pharmaceutically acceptable salts thereof.

15. The method according to claim 1, wherein the disease comprises tumor cell proliferation and the tumor is a lung, breast, colorectal, pancreatic, cervical or ovarian tumor, and the ChoK inhibitor is selected from

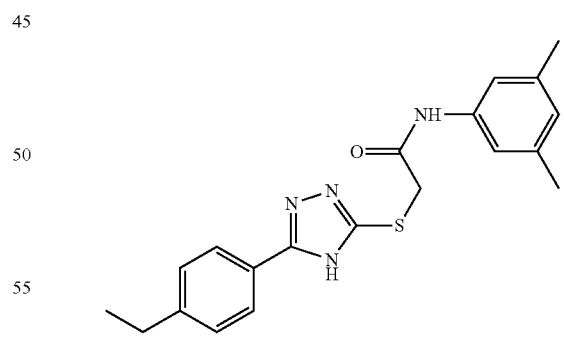

and the isomers, tautomers, and pharmaceutically acceptable salts thereof.

* * * * *

SEQUENCE LISTING

```
<160> NUMBER OF SEQ ID NOS: 1

<210> SEQ ID NO 1
<211> LENGTH: 457
<212> TYPE: PRT
<213> ORGANISM: Artificial Sequence
<220> FEATURE:
<223> OTHER INFORMATION: Can be part of choline kinase binding pocket

<400> SEQUENCE: 1

Met Lys Thr Lys Phe Cys Thr Gly Gly Glu Ala Glu Pro Ser Pro Leu
1               5                   10                  15

Gly Leu Leu Leu Ser Cys Gly Ser Gly Ser Ala Ala Pro Ala Pro Gly
            20                  25                  30
```

```
Val Gly Gln Gln Arg Asp Ala Ala Ser Asp Leu Glu Ser Lys Gln Leu
         35                  40                  45

Gly Gly Gln Gln Pro Pro Leu Ala Leu Pro Pro Pro Pro Pro Leu Pro
     50                  55                  60

Leu Pro Leu Pro Leu Pro Gln Pro Pro Pro Gln Pro Pro Pro Ala Asp
 65                  70                  75                  80

Glu Gln Pro Glu Pro Arg Thr Arg Arg Ala Tyr Leu Trp Cys Lys
                 85                  90                  95

Glu Phe Leu Pro Gly Ala Trp Arg Gly Leu Arg Glu Asp Glu Phe His
                100                 105                 110

Ile Ser Val Ile Arg Gly Gly Leu Ser Asn Met Leu Phe Gln Cys Ser
                115                 120                 125

Leu Pro Asp Thr Thr Ala Thr Leu Gly Asp Glu Pro Arg Lys Val Leu
                130                 135                 140

Leu Arg Leu Tyr Gly Ala Ile Leu Gln Met Arg Ser Cys Asn Lys Glu
145                 150                 155                 160

Gly Ser Glu Gln Ala Gln Lys Glu Asn Glu Phe Gln Gly Ala Glu Ala
                165                 170                 175

Met Val Leu Glu Ser Val Met Phe Ala Ile Leu Ala Glu Arg Ser Leu
                180                 185                 190

Gly Pro Lys Leu Tyr Gly Ile Phe Pro Gln Gly Arg Leu Glu Gln Phe
                195                 200                 205

Ile Pro Ser Arg Arg Leu Asp Thr Glu Glu Leu Ser Leu Pro Asp Ile
                210                 215                 220

Ser Ala Glu Ile Ala Glu Lys Met Ala Thr Phe His Gly Met Lys Met
225                 230                 235                 240

Pro Phe Asn Lys Glu Pro Lys Trp Leu Phe Gly Thr Met Glu Lys Tyr
                245                 250                 255

Leu Lys Glu Val Leu Arg Ile Lys Phe Thr Glu Glu Ser Arg Ile Lys
                260                 265                 270

Lys Leu His Lys Leu Leu Ser Tyr Asn Leu Pro Leu Glu Leu Glu Asn
                275                 280                 285

Leu Arg Ser Leu Leu Glu Ser Thr Pro Ser Pro Val Val Phe Cys His
                290                 295                 300

Asn Asp Cys Gln Glu Gly Asn Ile Leu Leu Leu Glu Gly Arg Glu Asn
305                 310                 315                 320

Ser Glu Lys Gln Lys Leu Met Leu Ile Asp Phe Glu Tyr Ser Ser Tyr
                325                 330                 335

Asn Tyr Arg Gly Phe Asp Ile Gly Asn His Phe Cys Glu Trp Met Tyr
                340                 345                 350

Asp Tyr Ser Tyr Glu Lys Tyr Pro Phe Phe Arg Ala Asn Ile Arg Lys
                355                 360                 365

Tyr Pro Thr Lys Lys Gln Gln Leu His Phe Ile Ser Ser Tyr Leu Pro
                370                 375                 380

Ala Phe Gln Asn Asp Phe Glu Asn Leu Ser Thr Glu Glu Lys Ser Ile
385                 390                 395                 400

Ile Lys Glu Glu Met Leu Leu Glu Val Asn Arg Phe Ala Leu Ala Ser
                405                 410                 415

His Phe Leu Trp Gly Leu Trp Ser Ile Val Gln Ala Lys Ile Ser Ser
                420                 425                 430

Ile Glu Phe Gly Tyr Met Asp Tyr Ala Gln Ala Arg Phe Asp Ala Tyr
                435                 440                 445
```

```
Phe His Gln Lys Arg Lys Leu Gly Val
    450                 455
```